(12) United States Patent
Plumridge et al.

(10) Patent No.: US 8,748,380 B2
(45) Date of Patent: Jun. 10, 2014

(54) ALBUMIN VARIANTS

(75) Inventors: Andrew Plumridge, Derbyshire (GB); Darrell Sleep, Nottingham (GB); Jason Cameron, Nottingham (GB); Inger Sandlie, Oslo (NO); Jan Terje Andersen, Oslo (NO); Esben Peter Friis, Herlev (DK)

(73) Assignee: Novozymes Biopharma DK A/S, Bagsvaerd (DK)

( * ) Notice: Subject to any disclaimer, the term of this patent is extended or adjusted under 35 U.S.C. 154(b) by 0 days.

(21) Appl. No.: 13/504,326

(22) PCT Filed: Nov. 1, 2010

(86) PCT No.: PCT/EP2010/066572
§ 371 (c)(1),
(2), (4) Date: Apr. 26, 2012

(87) PCT Pub. No.: WO2011/051489
PCT Pub. Date: May 5, 2011

(65) Prior Publication Data
US 2012/0220530 A1 Aug. 30, 2012

Related U.S. Application Data

(60) Provisional application No. 61/348,001, filed on May 25, 2010, provisional application No. 61/327,171, filed on Apr. 23, 2009.

(30) Foreign Application Priority Data

Oct. 30, 2009 (EP) .................................... 09174698
Aug. 26, 2010 (EP) .................................... 10174162

(51) Int. Cl.
| | |
|---|---|
| A61K 38/38 | (2006.01) |
| A61K 47/48 | (2006.01) |
| C07K 14/76 | (2006.01) |
| C07K 1/00 | (2006.01) |
| C07K 14/00 | (2006.01) |
| C07K 16/00 | (2006.01) |
| C07K 17/00 | (2006.01) |
| C07H 21/04 | (2006.01) |
| C12P 21/06 | (2006.01) |
| C12P 21/04 | (2006.01) |

(52) U.S. Cl.
USPC ........ 514/15.2; 530/362; 536/23.5; 536/23.4; 435/69.1; 435/69.7

(58) Field of Classification Search
None
See application file for complete search history.

(56) References Cited

U.S. PATENT DOCUMENTS

| | | | |
|---|---|---|---|
| 5,948,609 A | 9/1999 | Carter | |
| 7,253,259 B2 | 8/2007 | Otagiri | |
| 2004/0063635 A1 | 4/2004 | Yu | |
| 2006/0051859 A1* | 3/2006 | Fu et al. .................... | 435/320.1 |
| 2006/0178301 A1 | 8/2006 | Jurs | |
| 2010/0129846 A1 | 5/2010 | Goldknopf | |

FOREIGN PATENT DOCUMENTS

| | | |
|---|---|---|
| CA | 2562249 A1 * | 4/2007 |
| EP | 0286424 A1 | 10/1988 |
| EP | 0510693 A2 | 10/1992 |
| WO | 95/23857 A1 | 9/1995 |
| WO | 99/28348 A1 | 6/1999 |
| WO | 00/44772 A2 | 8/2000 |
| WO | 00/69902 A1 | 11/2000 |
| WO | 01/79271 A1 | 10/2001 |
| WO | 01/79480 A1 | 10/2001 |
| WO | 03/059934 A2 | 7/2003 |
| WO | 2004-011499 A1 | 2/2004 |
| WO | 2004/082640 A2 | 9/2004 |
| WO | 2005/003296 A2 | 1/2005 |
| WO | 2005/077042 A2 | 8/2005 |
| WO | 2006/066595 A2 | 6/2006 |
| WO | 2007/021494 A2 | 2/2007 |
| WO | 2007/112940 A2 | 10/2007 |
| WO | 2009/019314 A1 | 2/2009 |
| WO | 2009/126920 A2 | 10/2009 |
| WO | WO 2010059315 A1 * | 5/2010 |
| WO | 2010/068278 A2 | 6/2010 |
| WO | 2010/092135 A2 | 8/2010 |
| WO | 2010-118169 A2 | 10/2010 |
| WO | 2010-138814 A2 | 12/2010 |
| WO | 2011/011315 A1 | 1/2011 |
| WO | 2011/051489 A2 | 5/2011 |
| WO | 2011-103076 A1 | 8/2011 |
| WO | 2011/124718 A2 | 10/2011 |
| WO | 2011/146902 A1 | 11/2011 |
| WO | 2011/161127 A1 | 12/2011 |
| WO | 2012-059486 A1 | 5/2012 |
| WO | 2012/112188 A1 | 8/2012 |

OTHER PUBLICATIONS

Leger et al "Synthesis and in Vitro Analysis of Atrial Natriuretic Peptide-Albumin Conjugates" Bioorg and Med Chem Lett 13:3571-3575. Published Oct. 20, 2003.*
Peters et al, 1996, All About Albumin, Academic Press, iv-ix.

(Continued)

*Primary Examiner* — Maury Audet
*Assistant Examiner* — Zachary J Miknis
(74) *Attorney, Agent, or Firm* — Michael W. Krenicky

(57) ABSTRACT

The present invention relates to variants of a parent albumin having altered plasma half-life compared with the parent albumin. The present invention also relates to fusion polypeptides and conjugates comprising said variant albumin.

20 Claims, 32 Drawing Sheets

(56) References Cited

OTHER PUBLICATIONS

Peters et al, 1997, All About Albumin Review, Clin Chem 43, 2014a-2015a.
Peters, 1985, Adv Prot Chem 37, 161-245.
Prabhat et al, 2007, Proc Natl Acad Sci USA 104(14), 5889-5894.
Rice et al, 2000, Trends Genet 16, 276-277.
Roopenian et al, 2003, J Immunol 170(7), 3528-3533.
Roopenian et al, 2007, Nat Rev Immunol 7, 715-525.
Roopenian et al, 2010, Methods Mol Biol 602, 93-104.
Sheffield et al, 2000, Thrombosis Research 99(6), 613-621.
Sijmons et al, 1990, Biotech 8, 217-221.
Simard et al, 2005, Proc Natl Acad Sci USA 102(50), 17958-17963.
Sleep et al, 1990, Biotechnology 8, 42-46.
Sleep et al, 1991, Nature Biotechnol 9(2), 183-187.
Sleep et al, 2001, Yeast, 18(5), 403-421.
Stehle et al, 1997, Crit Rev Oncol Hematol 26(2), 77-100.
Sugio et al, 1999, Prot Eng 12(6), 439-446.
Takahashi et al, 1987, Proc Natl Acad Sci USA 84, 4413-4417.
Wani et al, 2006, Proc Natl Acad Sci USA 103(13), 5084-5089.
Ward et al, 2009, Adv Immunol 103, 77-115.
Werle et al, 2006, Amino Acids 30(4), 351-367.
West et al, 2000, Biochemistry 39(32), 9698-9708.
Zalevsky et al, 2010, Nat Biotech 28(2), 157-159.
Andersen et al, 2006, Eur J Immunol 36, 3044-3051.
Andersen et al, 2007, Clinic Chem 53(12), 2216.
Andersen et al, 2008, FEBS J 275(16), 4097-4110.
Andersen et al, 2010, Clinical Biochem 43, 367-372.
Andersen et al, 2010, J Biol Chem 285(7), 4826-4836.
Andersen et al, 2012, Nature 3(610), 1-9.
Anderson et al, 2006, Trends Immunol 27(7), 343-348.
Barash et al, 1993, Trans Res 2, 266-276.
Burmeister et al, 1994, Nature 372(6504), 336-343.
Burmeister et al, 1994, Nature 372(6504), 379-383.
Carlson et al, 1992, Proc Natl Acad Sci USA 89, 8225-8229.
Chaudhury et al, 2003, J Exp Med 197(3), 315-322.
Chaudhury et al, 2006, Biochemistry 45(15),4983-4990.
Chen et al, 2003, Protein 52, 80-87.
Curry et al, 1998, Nat Stuct Biol 5(9), 827-835.
Elble, 1992, Biotechniques 13(1), 18-20.
Farran et al, 2002, Trans Res 11, 337-346.
Fleer et al, 1991, Biotech 9, 968-975.
Galliano et al, 1993, Biochim Biophys Acta 1225(1), 27-32—Ab.
Hansen et al, 2005, Biochim Biophys Acta 1747(1), 81-88.
Hillier et al, 2007, Nature 434, 724-731—Uniprot, Access No. A6NBZ8.
Ishima et al, 2007, J Pharma Exp Therapeutics 320(3), 969-977.
Ito et al, 1983, J Bacteriol 153(1), 163-168.
Iwao et al, 2007, Biochim Biophys Acta 1774, 1582-1590.
Kenanova et al, 2005, Cancer Res 65(2), 622-631.
Kenanova et al, 2007, Cancer Res 67(2), 718-726.
Kenanova et al, 2009, J Nucl Med 50(2), 1582.
Kenanova et al, 2009, J Nucl Med 50, 1582—Ab.
Kenanova et al, 2010, Prot Eng Des 23, 789-798.
Kobayashi et al, 1998, Thera Apheresis 2, 257-262.
Kratz, 2008, J Controlled Release 132, 171-183.
Kuo et al, 2010, J Clin Immunol 30(6), 777-789.
Kurtzhals et al, 1995, Biochem J 312, 725-731.
Li et al, 2001, Intl Immunol 13(12), 1515-1523.
McGregor, 2008, Curr Opin Pharmacol 8(5), 616-619.
Mezo et al, 2010. J Biol Chem 285(36), 27694-27701.
Minchiotti et al, 1987, Biochim Biophys Acta 916, 411-418.
Minchiotti et al, 2008, Human Mutation 29(8), 1007-1016.
Montoyo et al, 2009, Proc Natl Acad Sci USA 106(8), 2788-2793.
NCBI Access No. 103600—Albumin (Sep. 2011).
NCP Web Catalog, 2005, 1-36.
Needleman et al, 1970, J Mol Biol 48, 443-453.
Ober et al, 2001, Int Immunol 13, 1551-1559.
Ober et al, 2004, J Immunol 172(4), 2021-2029.
Ober et al, 2004, Proc Natl Acad Sci USA 101(30), 11076-11081.
Olafsen et al, 2006, Nature Protocol 1(4), 2048-2060.
Otagiri et al, 2009, Biol Pharm Bull 32(4), 527-534.
Peach et al, 1991, Biochim Biophys Acta 1097, 49-54.
Peters et al, 1996, All About Albumin, 245-246.
Andersen et al, 2009, Drug Metab Pharmacokinet 24(4), 318-332.
Peters, 1996, All About Albumin, Biochem 10.
Bar-Or et al, 2006, Clin Chim Acta 365(1-2), 346-349.
Brennan et al, 2000, Biochim Biophys Acta 1481(2), 337-343.
Cronican et al, 2010—Geneseq, Access No. AXS56687.
Dagnino et al, 2010, Clinic Chimica Acta 411, 1711-1715.
Iwao et al, 2009, Biochem Biophys Acta 1794(4), 634-641.
Iwao et al, 2006, Biochim Biophys Acta 1764(4), 743-749.

\* cited by examiner

A.

B.

A.

B.

C.

D.

E.

F.

A

B

SEQUENCE LISTING

<160> NUMBER OF SEQ ID NOS: 55

<210> SEQ ID NO 1
<211> LENGTH: 1758
<212> TYPE: DNA
<213> ORGANISM: Homo sapiens
<220> FEATURE:
<221> NAME/KEY: CDS
<222> LOCATION: (1)..(1758)
<223> OTHER INFORMATION: Human serum albumin (mature protein)

<400> SEQUENCE: 1

```
gat gca cac aag agt gag gtt gct cat cgg ttt aaa gat ttg gga gaa         48
Asp Ala His Lys Ser Glu Val Ala His Arg Phe Lys Asp Leu Gly Glu
1               5                   10                  15 gaa aat ttc aaa gcc ttg gtg ttg att gcc ttt gct cag tat ctt cag         96
Glu Asn Phe Lys Ala Leu Val Leu Ile Ala Phe Ala Gln Tyr Leu Gln
                20                  25                  30 cag tgt cca ttt gaa gat cat gta aaa tta gtg aat gaa gta act gaa        144
Gln Cys Pro Phe Glu Asp His Val Lys Leu Val Asn Glu Val Thr Glu
            35                  40                  45 ttt gca aaa aca tgt gtt gct gat gag tca gct gaa aat tgt gac aaa        192
Phe Ala Lys Thr Cys Val Ala Asp Glu Ser Ala Glu Asn Cys Asp Lys
        50                  55                  60 tca ctt cat acc ctt ttt gga gac aaa tta tgc aca gtt gca act ctt        240
Ser Leu His Thr Leu Phe Gly Asp Lys Leu Cys Thr Val Ala Thr Leu
65                  70                  75                  80 cgt gaa acc tat ggt gaa atg gct gac tgc tgt gca aaa caa gaa cct        288
Arg Glu Thr Tyr Gly Glu Met Ala Asp Cys Cys Ala Lys Gln Glu Pro
                85                  90                  95 gag aga aat gaa tgc ttc ttg caa cac aaa gat gac aac cca aac ctc        336
Glu Arg Asn Glu Cys Phe Leu Gln His Lys Asp Asp Asn Pro Asn Leu
                100                 105                 110 ccc cga ttg gtg aga cca gag gtt gat gtg atg tgc act gct ttt cat        384
Pro Arg Leu Val Arg Pro Glu Val Asp Val Met Cys Thr Ala Phe His
            115                 120                 125 gac aat gaa gag aca ttt ttg aaa aaa tac tta tat gaa att gcc aga        432
Asp Asn Glu Glu Thr Phe Leu Lys Lys Tyr Leu Tyr Glu Ile Ala Arg
        130                 135                 140 aga cat cct tac ttt tat gcc ccg gaa ctc ctt ttc ttt gct aaa agg        480
Arg His Pro Tyr Phe Tyr Ala Pro Glu Leu Leu Phe Phe Ala Lys Arg
145                 150                 155                 160 tat aaa gct gct ttt aca gaa tgt tgc caa gct gct gat aaa gct gcc        528
Tyr Lys Ala Ala Phe Thr Glu Cys Cys Gln Ala Ala Asp Lys Ala Ala
                165                 170                 175 tgc ctg ttg cca aag ctc gat gaa ctt cgg gat gaa ggg aag gct tcg        576
Cys Leu Leu Pro Lys Leu Asp Glu Leu Arg Asp Glu Gly Lys Ala Ser
                180                 185                 190 tct gcc aaa cag aga ctc aag tgt gcc agt ctc caa aaa ttt gga gaa        624
Ser Ala Lys Gln Arg Leu Lys Cys Ala Ser Leu Gln Lys Phe Gly Glu
            195                 200                 205 aga gct ttc aaa gca tgg gca gta gct cgc ctg agc cag aga ttt ccc        672
Arg Ala Phe Lys Ala Trp Ala Val Ala Arg Leu Ser Gln Arg Phe Pro
        210                 215                 220 aaa gct gag ttt gca gaa gtt tcc aag tta gtg aca gat ctt acc aaa        720
Lys Ala Glu Phe Ala Glu Val Ser Lys Leu Val Thr Asp Leu Thr Lys
225                 230                 235                 240 gtc cac acg gaa tgc tgc cat gga gat ctg ctt gaa tgt gct gat gac        768
Val His Thr Glu Cys Cys His Gly Asp Leu Leu Glu Cys Ala Asp Asp
                245                 250                 255
```

```
agg gcg gac ctt gcc aag tat atc tgt gaa aat caa gat tcg atc tcc      816
Arg Ala Asp Leu Ala Lys Tyr Ile Cys Glu Asn Gln Asp Ser Ile Ser
        260                 265                 270 agt aaa ctg aag gaa tgc tgt gaa aaa cct ctg ttg gaa aaa tcc cac      864
Ser Lys Leu Lys Glu Cys Cys Glu Lys Pro Leu Leu Glu Lys Ser His
    275                 280                 285 tgc att gcc gaa gtg gaa aat gat gag atg cct gct gac ttg cct tca      912
Cys Ile Ala Glu Val Glu Asn Asp Glu Met Pro Ala Asp Leu Pro Ser
290                 295                 300 tta gct gct gat ttt gtt gaa agt aag gat gtt tgc aaa aac tat gct      960
Leu Ala Ala Asp Phe Val Glu Ser Lys Asp Val Cys Lys Asn Tyr Ala
305                 310                 315                 320 gag gca aag gat gtc ttc ctg ggc atg ttt ttg tat gaa tat gca aga     1008
Glu Ala Lys Asp Val Phe Leu Gly Met Phe Leu Tyr Glu Tyr Ala Arg
            325                 330                 335 agg cat cct gat tac tct gtc gtg ctg ctg ctg aga ctt gcc aag aca     1056
Arg His Pro Asp Tyr Ser Val Val Leu Leu Leu Arg Leu Ala Lys Thr
        340                 345                 350 tat gaa acc act cta gag aag tgc tgt gcc gct gca gat cct cat gaa     1104
Tyr Glu Thr Thr Leu Glu Lys Cys Cys Ala Ala Ala Asp Pro His Glu
    355                 360                 365 tgc tat gcc aaa gtg ttc gat gaa ttt aaa cct ctt gtg gaa gag cct     1152
Cys Tyr Ala Lys Val Phe Asp Glu Phe Lys Pro Leu Val Glu Glu Pro
370                 375                 380 cag aat tta atc aaa caa aat tgt gag ctt ttt gag cag ctt gga gag     1200
Gln Asn Leu Ile Lys Gln Asn Cys Glu Leu Phe Glu Gln Leu Gly Glu
385                 390                 395                 400 tac aaa ttc cag aat gcg cta tta gtt cgt tac acc aag aaa gta ccc     1248
Tyr Lys Phe Gln Asn Ala Leu Leu Val Arg Tyr Thr Lys Lys Val Pro
            405                 410                 415 caa gtg tca act cca act ctt gta gag gtc tca aga aac cta gga aaa     1296
Gln Val Ser Thr Pro Thr Leu Val Glu Val Ser Arg Asn Leu Gly Lys
        420                 425                 430 gtg ggc agc aaa tgt tgt aaa cat cct gaa gca aaa aga atg ccc tgt     1344
Val Gly Ser Lys Cys Cys Lys His Pro Glu Ala Lys Arg Met Pro Cys
    435                 440                 445 gca gaa gac tat cta tcc gtg gtc ctg aac cag tta tgt gtg ttg cat     1392
Ala Glu Asp Tyr Leu Ser Val Val Leu Asn Gln Leu Cys Val Leu His
450                 455                 460 gag aaa acg cca gta agt gac aga gtc acc aaa tgc tgc aca gaa tcc     1440
Glu Lys Thr Pro Val Ser Asp Arg Val Thr Lys Cys Cys Thr Glu Ser
465                 470                 475                 480 ttg gtg aac agg cga cca tgc ttt tca gct ctg gaa gtc gat gaa aca     1488
Leu Val Asn Arg Arg Pro Cys Phe Ser Ala Leu Glu Val Asp Glu Thr
            485                 490                 495 tac gtt ccc aaa gag ttt aat gct gaa aca ttc acc ttc cat gca gat     1536
Tyr Val Pro Lys Glu Phe Asn Ala Glu Thr Phe Thr Phe His Ala Asp
        500                 505                 510 ata tgc aca ctt tct gag aag gag aga caa atc aag aaa caa act gca     1584
Ile Cys Thr Leu Ser Glu Lys Glu Arg Gln Ile Lys Lys Gln Thr Ala
    515                 520                 525 ctt gtt gag ctc gtg aaa cac aag ccc aag gca aca aaa gag caa ctg     1632
Leu Val Glu Leu Val Lys His Lys Pro Lys Ala Thr Lys Glu Gln Leu
530                 535                 540 aaa gct gtt atg gat gat ttc gca gct ttt gta gag aag tgc tgc aag     1680
Lys Ala Val Met Asp Asp Phe Ala Ala Phe Val Glu Lys Cys Cys Lys
545                 550                 555                 560 gct gac gat aag gag acc tgc ttt gcc gag gag ggt aaa aaa ctt gtt     1728
Ala Asp Asp Lys Glu Thr Cys Phe Ala Glu Glu Gly Lys Lys Leu Val
            565                 570                 575
```

```
gct gca agt caa gct gcc tta ggc tta taa                                  1758
Ala Ala Ser Gln Ala Ala Leu Gly Leu
            580                 585

<210> SEQ ID NO 2
<211> LENGTH: 585
<212> TYPE: PRT
<213> ORGANISM: Homo sapiens

<400> SEQUENCE: 2

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

Cys Tyr Ala Lys Val Phe Asp Glu Phe Lys Pro Leu Val Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 3
<211> LENGTH: 290
<212> TYPE: PRT
<213> ORGANISM: Homo sapiens

<400> SEQUENCE: 3

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

```
Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu
    290

<210> SEQ ID NO 4
<211> LENGTH: 125
<212> TYPE: PRT
<213> ORGANISM: Homo sapiens

<400> SEQUENCE: 4

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met His His His His His
        115                 120                 125

<210> SEQ ID NO 5
<211> LENGTH: 55
<212> TYPE: DNA
<213> ORGANISM: Artificial
<220> FEATURE:
<223> OTHER INFORMATION: Primer xAP094

<400> SEQUENCE: 5
ccatgctttt cagctctgga agtcaatcaa gcttacgttc ccaaagagtt taatg        55

<210> SEQ ID NO 6
<211> LENGTH: 55
<212> TYPE: DNA
<213> ORGANISM: Artificial
<220> FEATURE:
<223> OTHER INFORMATION: Primer xAP095
```

-continued

```
<400> SEQUENCE: 6
cattaaactc tttgggaacg taagcttgat tgacttccag agctgaaaag catgg         55

<210> SEQ ID NO 7
<211> LENGTH: 51
<212> TYPE: DNA
<213> ORGANISM: Artificial
<220> FEATURE:
<223> OTHER INFORMATION: Primer xAP096

<400> SEQUENCE: 7
gcttttcagc tctggaagtc gatcaagctt acgttcccaa agagtttaat g             51

<210> SEQ ID NO 8
<211> LENGTH: 51
<212> TYPE: DNA
<213> ORGANISM: Artificial
<220> FEATURE:
<223> OTHER INFORMATION: Primer xAP097

<400> SEQUENCE: 8
cattaaactc tttgggaacg taagcttgat cgacttccag agctgaaaag c             51

<210> SEQ ID NO 9
<211> LENGTH: 13
<212> TYPE: PRT
<213> ORGANISM: Homo sapeins

<400> SEQUENCE: 9

Lys Lys Leu Val Ala Ala Ser Gln Ala Ala Leu Gly Leu
1               5                   10

<210> SEQ ID NO 10
<211> LENGTH: 12
<212> TYPE: PRT
<213> ORGANISM: Artificial
<220> FEATURE:
<223> OTHER INFORMATION: macaque albumin fragment

<400> SEQUENCE: 10

Pro Lys Phe Val Ala Ala Ser Gln Ala Ala Leu Ala
1               5                   10

<210> SEQ ID NO 11
<211> LENGTH: 12
<212> TYPE: PRT
<213> ORGANISM: Artificial
<220> FEATURE:
<223> OTHER INFORMATION: Mouse albumin fragment

<400> SEQUENCE: 11

Pro Asn Leu Val Thr Arg Cys Lys Asp Ala Leu Ala
1               5                   10

<210> SEQ ID NO 12
<211> LENGTH: 12
<212> TYPE: PRT
<213> ORGANISM: Artificial
<220> FEATURE:
<223> OTHER INFORMATION: rabbit albumin fragment

<400> SEQUENCE: 12

Pro Lys Leu Val Glu Ser Ser Lys Ala Thr Leu Gly
1               5                   10

<210> SEQ ID NO 13
```

<211> LENGTH: 12
<212> TYPE: PRT
<213> ORGANISM: Artificial
<220> FEATURE:
<223> OTHER INFORMATION: sheep albumin fragment

<400> SEQUENCE: 13

Pro Lys Leu Val Ala Ser Thr Gln Ala Ala Leu Ala
1               5                   10

<210> SEQ ID NO 14
<211> LENGTH: 45
<212> TYPE: DNA
<213> ORGANISM: Artificial
<220> FEATURE:
<223> OTHER INFORMATION: Primer xAP216

<400> SEQUENCE: 14
ctttggaagt cgacgaaact tacgttccag gtgaattcaa cgctg          45

<210> SEQ ID NO 15
<211> LENGTH: 45
<212> TYPE: DNA
<213> ORGANISM: Artificial
<220> FEATURE:
<223> OTHER INFORMATION: Primer xAP217

<400> SEQUENCE: 15
ctttggaagt cgacgaaact tacgttccag aagaattcaa cgctg          45

<210> SEQ ID NO 16
<211> LENGTH: 45
<212> TYPE: DNA
<213> ORGANISM: Artificial
<220> FEATURE:
<223> OTHER INFORMATION: Primer xAP218

<400> SEQUENCE: 16
ctttggaagt cgacgaaact tacgttccag acgaattcaa cgctg          45

<210> SEQ ID NO 17
<211> LENGTH: 45
<212> TYPE: DNA
<213> ORGANISM: Artificial
<220> FEATURE:
<223> OTHER INFORMATION: Primer xAP219

<400> SEQUENCE: 17
ctttggaagt cgacgaaact tacgttccag ttgaattcaa cgctg          45

<210> SEQ ID NO 18
<211> LENGTH: 45
<212> TYPE: DNA
<213> ORGANISM: Artificial
<220> FEATURE:
<223> OTHER INFORMATION: Primer xAP220

<400> SEQUENCE: 18
ctttggaagt cgacgaaact tacgttccaa gagaattcaa cgctg          45

<210> SEQ ID NO 19
<211> LENGTH: 45
<212> TYPE: DNA
<213> ORGANISM: Artificial
<220> FEATURE:
<223> OTHER INFORMATION: Primer xAP221

<400> SEQUENCE: 19
ctttggaagt cgacgaaact tacgttccaa acgaattcaa cgctg       45

<210> SEQ ID NO 20
<211> LENGTH: 45
<212> TYPE: DNA
<213> ORGANISM: Artificial
<220> FEATURE:
<223> OTHER INFORMATION: Primer xAP220

<400> SEQUENCE: 20
ctttggaagt cgacgaaact tacgttccaa tggaattcaa cgctg       45

<210> SEQ ID NO 21
<211> LENGTH: 45
<212> TYPE: DNA
<213> ORGANISM: Artificial
<220> FEATURE:
<223> OTHER INFORMATION: Primer xAP223

<400> SEQUENCE: 21
ctttggaagt cgacgaaact tacgttccaa ttgaattcaa cgctg       45

<210> SEQ ID NO 22
<211> LENGTH: 45
<212> TYPE: DNA
<213> ORGANISM: Artificial
<220> FEATURE:
<223> OTHER INFORMATION: Primer xAP224

<400> SEQUENCE: 22
ctttggaagt cgacgaaact tacgttccaa ccgaattcaa cgctg       45

<210> SEQ ID NO 23
<211> LENGTH: 45
<212> TYPE: DNA
<213> ORGANISM: Artificial
<220> FEATURE:
<223> OTHER INFORMATION: Primer xAP225

<400> SEQUENCE: 23
ctttggaagt cgacgaaact tacgttccat gggaattcaa cgctg       45

<210> SEQ ID NO 24
<211> LENGTH: 45
<212> TYPE: DNA
<213> ORGANISM: Artificial
<220> FEATURE:
<223> OTHER INFORMATION: Primer xAP226

<400> SEQUENCE: 24
ctttggaagt cgacgaaact tacgttccat gtgaattcaa cgctg       45

<210> SEQ ID NO 25
<211> LENGTH: 45
<212> TYPE: DNA
<213> ORGANISM: Artificial
<220> FEATURE:
<223> OTHER INFORMATION: Primer xAP227

<400> SEQUENCE: 25
ctttggaagt cgacgaaact tacgttccat acgaattcaa cgctg       45

<210> SEQ ID NO 26
<211> LENGTH: 45
<212> TYPE: DNA
<213> ORGANISM: Artificial

<220> FEATURE:
<223> OTHER INFORMATION: Primer xAP229

<400> SEQUENCE: 26
ctttggaagt cgacgaaact tacgttccat tggaattcaa cgctg        45

<210> SEQ ID NO 27
<211> LENGTH: 45
<212> TYPE: DNA
<213> ORGANISM: Artificial
<220> FEATURE:
<223> OTHER INFORMATION: Primer xAP229

<400> SEQUENCE: 27
ctttggaagt cgacgaaact tacgttccat tcgaattcaa cgctg        45

<210> SEQ ID NO 28
<211> LENGTH: 45
<212> TYPE: DNA
<213> ORGANISM: Artificial
<220> FEATURE:
<223> OTHER INFORMATION: Primer xAP230

<400> SEQUENCE: 28
ctttggaagt cgacgaaact tacgttccat ctgaattcaa cgctg        45

<210> SEQ ID NO 29
<211> LENGTH: 45
<212> TYPE: DNA
<213> ORGANISM: Artificial
<220> FEATURE:
<223> OTHER INFORMATION: Primer xAP231

<400> SEQUENCE: 29
ctttggaagt cgacgaaact tacgttccac aagaattcaa cgctg        45

<210> SEQ ID NO 30
<211> LENGTH: 45
<212> TYPE: DNA
<213> ORGANISM: Artificial
<220> FEATURE:
<223> OTHER INFORMATION: Primer xAP232

<400> SEQUENCE: 30
ctttggaagt cgacgaaact tacgttccac acgaattcaa cgctg        45

<210> SEQ ID NO 31
<211> LENGTH: 45
<212> TYPE: DNA
<213> ORGANISM: Artificial
<220> FEATURE:
<223> OTHER INFORMATION: Primer xAP233

<400> SEQUENCE: 31
ctttggaagt cgacgaaact tacgttccac cagaattcaa cgctg        45

<210> SEQ ID NO 32
<211> LENGTH: 45
<212> TYPE: DNA
<213> ORGANISM: Artificial
<220> FEATURE:
<223> OTHER INFORMATION: Primer xAP234

<400> SEQUENCE: 32
ctttggaagt cgacgaaact tacgttccat aagaattcaa cgctg        45

<210> SEQ ID NO 33
<211> LENGTH: 39
<212> TYPE: DNA
<213> ORGANISM: Artificial
<220> FEATURE:
<223> OTHER INFORMATION: Primer xAP235

<400> SEQUENCE: 33
gaattaagct tattacaaac ccaaagcagc ttgggaagc					39

<210> SEQ ID NO 34
<211> LENGTH: 50
<212> TYPE: DNA
<213> ORGANISM: Artificial
<220> FEATURE:
<223> OTHER INFORMATION: Primer xAP187

<400> SEQUENCE: 34
ataagcctaa ggcagcttga cttgcagcaa caagtttacc accctcctcg					50

<210> SEQ ID NO 35
<211> LENGTH: 50
<212> TYPE: DNA
<213> ORGANISM: Artificial
<220> FEATURE:
<223> OTHER INFORMATION: Primer xAP188

<400> SEQUENCE: 35
ataagcctaa ggcagcttga cttgcagcaa caagtttttc accctcctcg					50

<210> SEQ ID NO 36
<211> LENGTH: 50
<212> TYPE: DNA
<213> ORGANISM: Artificial
<220> FEATURE:
<223> OTHER INFORMATION: Primer xAP189

<400> SEQUENCE: 36
ataagcctaa ggcagcttga cttgcagcaa caagtttatc accctcctcg					50

<210> SEQ ID NO 37
<211> LENGTH: 50
<212> TYPE: DNA
<213> ORGANISM: Artificial
<220> FEATURE:
<223> OTHER INFORMATION: Priner xAP190

<400> SEQUENCE: 37
ataagcctaa ggcagcttga cttgcagcaa caagtttaac accctcctcg					50

<210> SEQ ID NO 38
<211> LENGTH: 50
<212> TYPE: DNA
<213> ORGANISM: Artificial
<220> FEATURE:
<223> OTHER INFORMATION: Primer xAP191

<400> SEQUENCE: 38
ataagcctaa ggcagcttga cttgcagcaa caagttttct accctcctcg					50

<210> SEQ ID NO 39
<211> LENGTH: 50
<212> TYPE: DNA
<213> ORGANISM: Artificial
<220> FEATURE:
<223> OTHER INFORMATION: Primer xAP192

<400> SEQUENCE: 39
ataagcctaa ggcagcttga cttgcagcaa caagtttatt accctcctcg          50

<210> SEQ ID NO 40
<211> LENGTH: 50
<212> TYPE: DNA
<213> ORGANISM: Artificial
<220> FEATURE:
<223> OTHER INFORMATION: Primer xAP193

<400> SEQUENCE: 40
ataagcctaa ggcagcttga cttgcagcaa caagtttcat accctcctcg          50

<210> SEQ ID NO 41
<211> LENGTH: 50
<212> TYPE: DNA
<213> ORGANISM: Artificial
<220> FEATURE:
<223> OTHER INFORMATION: Primer xAP194

<400> SEQUENCE: 41
ataagcctaa ggcagcttga cttgcagcaa caagtttaat accctcctcg          50

<210> SEQ ID NO 42
<211> LENGTH: 50
<212> TYPE: DNA
<213> ORGANISM: Artificial
<220> FEATURE:
<223> OTHER INFORMATION: Primer xAP195

<400> SEQUENCE: 42
ataagcctaa ggcagcttga cttgcagcaa caagtttagt accctcctcg          50

<210> SEQ ID NO 43
<211> LENGTH: 50
<212> TYPE: DNA
<213> ORGANISM: Artificial
<220> FEATURE:
<223> OTHER INFORMATION: Primer xAP196

<400> SEQUENCE: 43
ataagcctaa ggcagcttga cttgcagcaa caagtttcca accctcctcg          50

<210> SEQ ID NO 44
<211> LENGTH: 50
<212> TYPE: DNA
<213> ORGANISM: Artificial
<220> FEATURE:
<223> OTHER INFORMATION: Primer xAP197

<400> SEQUENCE: 44
ataagcctaa ggcagcttga cttgcagcaa caagtttaca accctcctcg          50

<210> SEQ ID NO 45
<211> LENGTH: 50
<212> TYPE: DNA
<213> ORGANISM: Artificial
<220> FEATURE:
<223> OTHER INFORMATION: Primer xAP198

<400> SEQUENCE: 45
ataagcctaa ggcagcttga cttgcagcaa caagtttata accctcctcg          50

<210> SEQ ID NO 46
<211> LENGTH: 50
<212> TYPE: DNA
<213> ORGANISM: Artificial

-continued

```
<220> FEATURE:
<223> OTHER INFORMATION: Primer xAP199

<400> SEQUENCE: 46
ataagcctaa ggcagcttga cttgcagcaa caagtttcaa accctcctcg                 50

<210> SEQ ID NO 47
<211> LENGTH: 50
<212> TYPE: DNA
<213> ORGANISM: Artificial
<220> FEATURE:
<223> OTHER INFORMATION: Primer xAP200

<400> SEQUENCE: 47
ataagcctaa ggcagcttga cttgcagcaa caagtttaaa accctcctcg                 50

<210> SEQ ID NO 48
<211> LENGTH: 50
<212> TYPE: DNA
<213> ORGANISM: Artificial
<220> FEATURE:
<223> OTHER INFORMATION: Primer xAP201

<400> SEQUENCE: 48
ataagcctaa ggcagcttga cttgcagcaa caagtttaga accctcctcg                 50

<210> SEQ ID NO 49
<211> LENGTH: 50
<212> TYPE: DNA
<213> ORGANISM: Artificial
<220> FEATURE:
<223> OTHER INFORMATION: Primer xAP202

<400> SEQUENCE: 49
ataagcctaa ggcagcttga cttgcagcaa caagttttg accctcctcg                  50

<210> SEQ ID NO 50
<211> LENGTH: 50
<212> TYPE: DNA
<213> ORGANISM: Artificial
<220> FEATURE:
<223> OTHER INFORMATION: Primer xAP203

<400> SEQUENCE: 50
ataagcctaa ggcagcttga cttgcagcaa caagtttatg accctcctcg                 50

<210> SEQ ID NO 51
<211> LENGTH: 50
<212> TYPE: DNA
<213> ORGANISM: Artificial
<220> FEATURE:
<223> OTHER INFORMATION: Primer xAP204

<400> SEQUENCE: 51
ataagcctaa ggcagcttga cttgcagcaa caagttttta accctcctcg                 50

<210> SEQ ID NO 52
<211> LENGTH: 36
<212> TYPE: DNA
<213> ORGANISM: Artificial
<220> FEATURE:
<223> OTHER INFORMATION: Primer xAP205

<400> SEQUENCE: 52
aatgctgcca tggagatctg cttgaatgtg ctgatg                                36
```

```
<210> SEQ ID NO 53
<211> LENGTH: 67
<212> TYPE: DNA
<213> ORGANISM: Artificial
<220> FEATURE:
<223> OTHER INFORMATION: Primer xAP238

<400> SEQUENCE: 53
gaattaagct tattacaaac ctaaggcagc ttgggaagca gcgaccaact tagcaccttc    60
ttcagcg                                                              67

<210> SEQ ID NO 54
<211> LENGTH: 33
<212> TYPE: DNA
<213> ORGANISM: Artificial
<220> FEATURE:
<223> OTHER INFORMATION: Primer xAP239

<400> SEQUENCE: 54
gtttctctgc tttggaagtc gacgaaactt acg                                 33

<210> SEQ ID NO 55
<211> LENGTH: 708
<212> TYPE: DNA
<213> ORGANISM: Artificial
<220> FEATURE:
<223> OTHER INFORMATION: synthetic IL-1RA

<400> SEQUENCE: 55
ccttaggctt aggtggttct ggtggttccg gtggttctgg tggatccggt ggtcgaccct    60
ctgggagaaa atccagcaag atgcaagcct tcagaatctg ggatgttaac cagaagacct   120
tctatctgag gaacaaccaa ctagttgctg atacttgca aggaccaaat gtcaatttag    180
aagaaaagat agatgtggta cccattgagc ctcatgctct gttcttggga atccatggag   240
ggaagatgtg cctgtcctgt gtcaagtctg gtgatgagac cagactccag ctggaggcag   300
ttcaaatcac tgacctgagc gagaacagaa agcaggacaa gcgcttcgcc ttcatccgct   360
cagacagcgg ccccaccacc agttttgagt ctgccgcctg ccccggttgg ttcctctgca   420
cagcgatgga agctgaccag cccgtcagcc tcaccaatat gcctgacgaa ggcgtcatgg   480
tcaccaaatt ctacttccag gaggacgagt aataagctta attcttatga tttatgattt   540
ttattattaa ataagttata aaaaaaataa gtgtatacaa attttaaagt gactcttagg   600
ttttaaaacg aaaattctta ttcttgagta actctttcct gtaggtcagg ttgctttctc   660
aggtatagca tgaggtcgct cttattgacc acacctctac cggcatgc               708
```

ALBUMIN VARIANTS

CROSS-REFERENCE TO RELATED APPLICATIONS

This application is a 35 U.S.C. 371 national application of PCT/EP2010/066572 filed Nov. 1, 2010, which claims priority or the benefit under 35 U.S.C. 119 of European application nos. 10174162.7 and 09174698.2 filed Aug. 26, 2010 and Oct. 30, 2009, respectively, and U.S. provisional application Nos. 61/348,001 and 61/327,171 filed May 25, 2010 and Apr. 23, 2010, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to variants of albumin or fragments thereof or fusion polypeptides comprising variant albumin or fragments thereof having a change in half-life compared to the albumin, fragment thereof or fusion polypeptide comprising albumin or a fragment thereof.

2. Description of the Related Art

Albumin is a protein naturally found in the blood plasma of mammals where it is the most abundant protein. It has important roles in maintaining the desired osmotic pressure of the blood and also in transport of various substances in the blood stream.

Albumins have been characterized from many species including human, pig, mouse, rat, rabbit and goat and they share a high degree of sequence and structural homology.

Albumin binds in vivo to its receptor, the neonatal Fc receptor (FcRn) "Brambell" and this interaction is known to be important for the plasma half-life of albumin. FcRn is a membrane bound protein, expressed in many cell and tissue types. FcRn has been found to salvage albumin from intracellular degradation (Roopenian D. C. and Akilesh, S. (2007), *Nat. Rev. Immunol* 7, 715-725.). FcRn is a bifunctional molecule that contributes to maintaining a high level of IgGs and albumin in serum in mammals such as human beings.

Whilst the FcRn-immunoglobulin (IgG) interaction has been characterized in the prior art, the FcRn-albumin interaction is less well characterized. The major FcRn binding site is localized within DIII (381-585). Andersen et al (2010). Clinical Biochemistry 43, 367-372. Data indicates that IgG and albumin bind non-cooperatively to distinct sites on FcRn (Andersen et al. (2006), *Eur. J. Immunol* 36, 3044-3051; Chaudhury et al. (2006), *Biochemistry* 45, 4983-4990.).

It is known that mouse FcRn binds IgG from mice and humans whereas human FcRn appears to be more discriminating (Ober et al. (2001) *Int. Immunol* 13, 1551-1559). Andersen et al. (2010). Journal of Biological Chemistry 285 (7):4826-36, describes the affinity of human and mouse FcRn for each mouse and human albumin (all possible combinations). No binding of albumin from either species was observed at physiological pH to either receptor. At acidic pH, a 100-fold difference in binding affinity was observed. In all cases, binding of albumin and IgG from either species to both receptors were additive.

Human serum albumin (HSA) has been well characterized as a polypeptide of 585 amino acids, the sequence of which can be found in Peters, T., Jr. (1996) *All about Albumin: Biochemistry, Genetics and Medical, Applications* pp 10, Academic Press, Inc., Orlando (ISBN 0-12-552110-3). It has a characteristic binding to its receptor FcRn, where it binds at pH 6.0 but not at pH 7.4.

The plasma half-life of HSA has been found to be approximately 19 days. A natural variant having lower plasma half-life has been identified (Peach, R. J. and Brennan, S. 0., (1991) *Biochim Biophys Acta.* 1097:49-54) having the substitution D494N. This substitution generated an N-glycosylation site in this variant, which is not present in the wild-type albumin. It is not known whether the glycosylation or the amino acid change is responsible for the change in plasma half-life.

Albumin has a long plasma half-life and because of this property it has been suggested for use in drug delivery. Albumin has been conjugated to pharmaceutically beneficial compounds (WO 2000/69902A), and it was found that the conjugate—maintained the long plasma half-life of albumin. The resulting plasma half-life of the conjugate was generally considerably longer than the plasma half-life of the beneficial therapeutic compound alone.

Further, albumin has been fused to therapeutically beneficial peptides (WO 2001/79271 A and WO 2003/59934 A) with the typical result that the fusion has the activity of the therapeutically beneficial peptide and a considerably longer plasma half-life than the plasma half-life of the therapeutically beneficial peptides alone.

Otagiri et al (2009), Biol. Pharm, Bull. 32(4), 527-534, discloses that 77 albumin variant are know, of these 25 are found in domain III. A natural variant lacking the last 175 amino acids at the carboxy termini has been shown to have reduced half-life (Andersen et al (2010), Clinical Biochemistry 43, 367-372). Iwao et al. (2007) studied the half-life of naturally accuring human albumin variants using a mouse model, and found that K541E and K560E had reduced half-life, E501K and E570K had increased half-life and K573E had almost no effect on half-life (Iwao, et. al. (2007) B.B.A. Proteins and Proteomics 1774, 1582-1590).

Galliano et al (1993) Biochim. Biophys. Acta 1225, 27-32 discloses a natural variant E505K. Minchiotti et al. (1990) discloses a natural variant K536E. Minchiotti et al (1987) Biochim. Biophys. Acta 916, 411-418 discloses a natural variant K574N. Takahashi et al (1987) Proc. Natl. Acad. Sci. USA 84, 4413-4417, discloses a natural variant D550G. Carlson et al (1992). Proc. Nat. Acad. Sci. USA 89, 8225-8229, discloses a natural variant D550A.

Albumin has the ability to bind a number of ligands and these become associated (associates) with albumin. This property has been utilized to extend the plasma half-life of drugs having the ability to noncovalently bind to albumin. This can also be achieved by binding a pharmaceutical beneficial compound, which has little or no albumin binding properties, to a moiety having albumin binding properties. See review article and reference therein, Kratz (2008). Journal of Controlled Release 132, 171-183.

Albumin is used in preparations of pharmaceutically beneficial compounds, in which such a preparation maybe for example, but not limited to, a nano particle or micro particle of albumin. In these examples the delivery of a pharmaceutically beneficial compound or mixture of compounds may benefit from alteration in the albumins affinity to its receptor where the beneficial compound has been shown to associate with albumin for the means of delivery.

It is not clear what determines the plasma half-life of the formed associates (for example but not limited to Levemir®, Kurtzhals P et al. Biochem. J. 1995; 312:725-731) conjugates or fusion polypeptides but it appears to be a result of the combination of the albumin and the selected pharmaceutically beneficial compound/polypeptide. It would be desirable to be able to control the plasma half-life of given albumin conjugates, associates or albumin fusion polypeptides so that a longer or shorter plasma half-life can be achieved than given by the components of the association, conjugation or fusion, in order to be able to design a particular drug according to the particulars of the indication intended to be treated.

Albumin is known to accumulate and be catabolised in tumours, it has also been shown to accumulate in inflamed joints of rheumatoid arthritis sufferers. See review article and reference therein, Kratz (2008). Journal of Controlled Release 132, 171-183. It is envisaged that HSA variants with increased affinity for FcRn would be advantageous for the delivery of pharmaceutically beneficial compounds.

It may even be desirable to have variants of albumin that have little or no binding to FcRn in order to provide shorter half-lives or controlled serum pharmacokinetics as described by Kenanova et al (2009) *J. Nucl. Med.;* 50 (Supplement 2):1582).

SUMMARY OF THE INVENTION

The present invention provides variants of a parent albumin with improved properties compared to its parent. In particular the invention provides variants of a parent albumin having altered plasma half-life compare to its parent.

The present invention relates to isolated variants of albumin or fragments thereof, or fusion polypeptides comprising variant albumin or fragments thereof, of a parent albumin, comprising an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of the mature polypeptide of SEQ ID NO: 2, wherein the variant is not the variant consisting of SEQ ID NO: 2 with the substitution D494N, E501K, K541E, D550G,A, K573E or K574N.

The alteration at one or more position may independently be selected among substitutions, insertions and deletions, where substitution are preferred.

The present invention also relates to isolated polynucleotides encoding the variants; nucleic acid constructs, vectors, and host cells comprising the polynucleotides; and methods of producing the variants.

The present invention also relates to conjugates or associates comprising the variant albumin or fragment thereof according to the invention and a beneficial therapeutic moiety or to a fusion polypeptide comprising a variant albumin or fragment thereof of the invention and a fusion partner polypeptide.

The invention further relates to compositions comprising the variant albumin, fragment thereof, fusion polypeptide comprising variant albumin or fragment thereof or conjugates comprising the variant albumin or fragment thereof, according to the invention or associates comprising the variant albumin or fragment thereof, according to the invention. The compositions are preferably pharmaceutical compositions.

The invention further relates to a pharmaceutical composition comprising a variant albumin, fragment thereof, fusion polypeptide comprising variant albumin or fragment thereof or conjugates comprising the variant albumin or fragment thereof, or associates comprising the variant albumin or fragment thereof, wherein said variant albumin, fragment thereof, fusion polypeptide comprising variant albumin or fragment thereof or conjugates comprising the variant albumin or fragment or associates of variant albumin or fragment thereof has altered plasma half-life compared to the corresponding plasma half-life of the HSA or fragment thereof, fusion polypeptide comprising HSA or fragment thereof or conjugates or associates of HSA or, fragment thereof, comprising HSA or fragment thereof.

WT and K573E, (C) WT and K573H, (D) WT and K573I and (E) WT and K573N and (F) WT and K573P, (G) WT and K573S, (H) WT and K573* and (I) WT and K573W and (J) WT and K573Y injected over immobilized shFcRn at pH 5.5 and pH7.4. Injections were performed at 25° C. at a flow rate of 80 µl/min.

Figure 14:
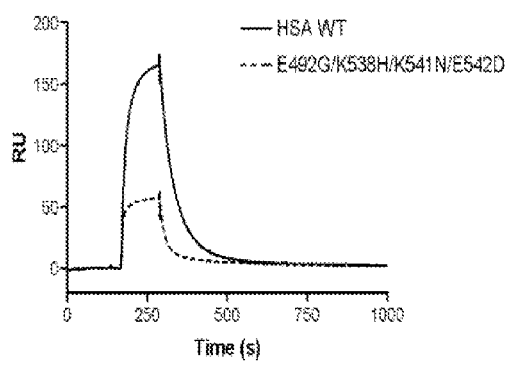
Figure 14:
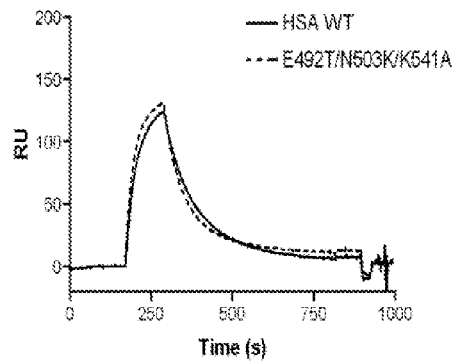
Figure 14:
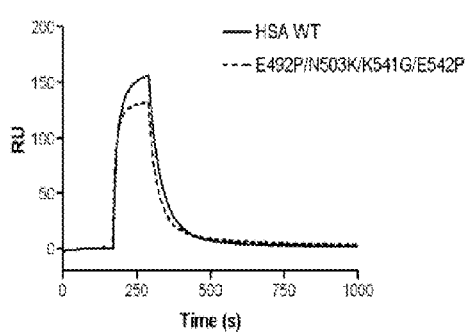
Figure 14:
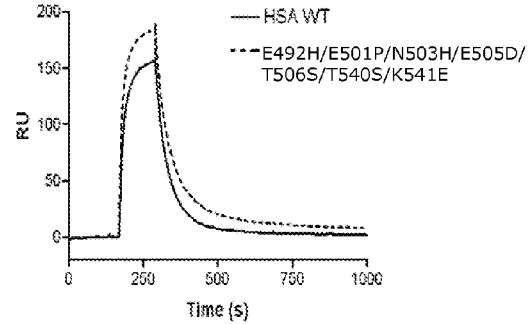
Figure 14:
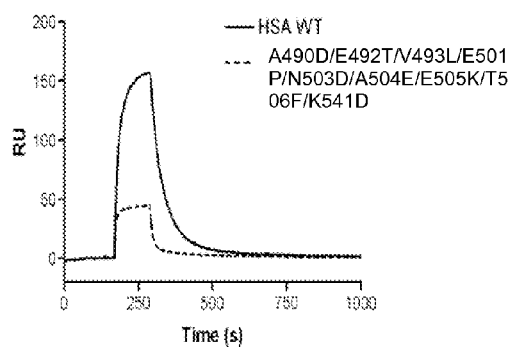
Figure 14:
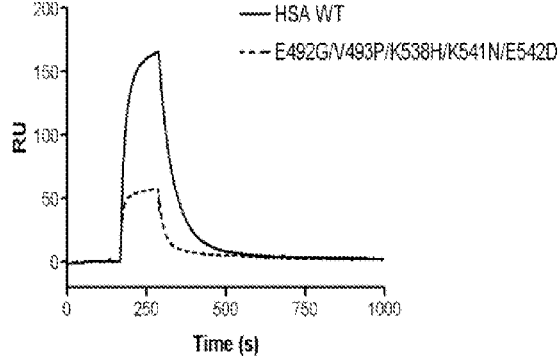

FIG. 14 shows SPR sensorgrams of HSA mutants compared with wild-type HSA. 20 µM of (A) WT and E492G+K538H+K541N+E542D (B) WT and E492T+N503K+K541A, (C) WT and E492P+N503K+K541G+E542P, (D) WT and E492H+E501P+N503H+E505D+T506S+T540S+K541E and (E) WT and A490D+E492T+V493L+E501P+N503D+A504E+E505K+T506F+K541D and (F) WT and E492G+V493P+K538H+K541N+E542D injected over immobilized shFcRn at pH 6.0. Injections were performed at 25° C. at a flow rate of 80 µl/min.

Figure 15:
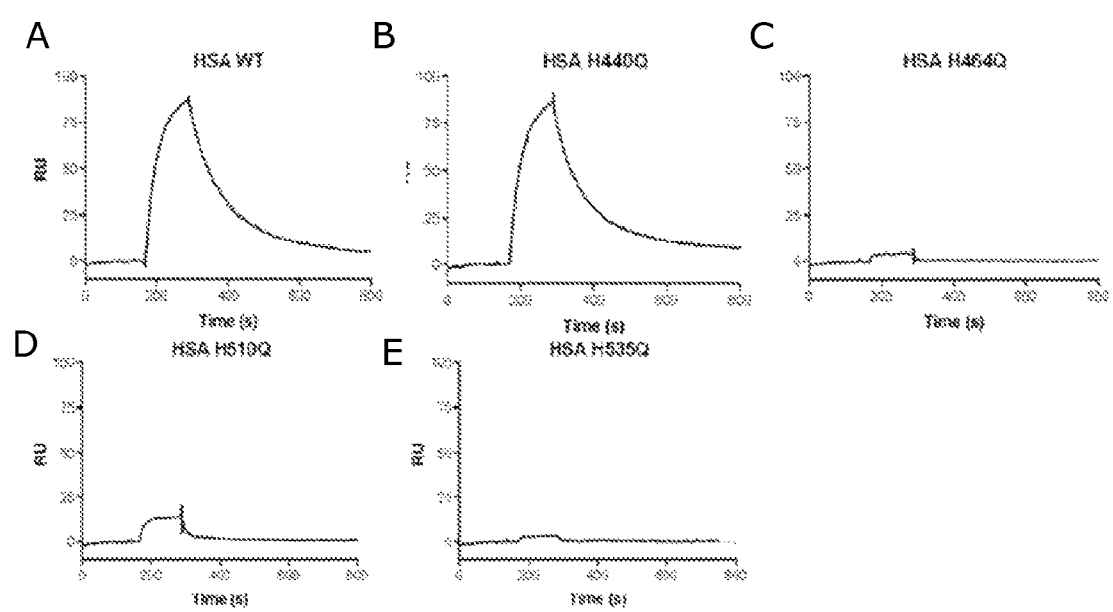

FIG. 15 shows SPR sensorgrams of HSA mutants compared with wild-type HSA. Twenty µM of (A) WT, (B) H440Q, (C) H464Q and (D) H535Q injected over immobilized shFcRn at pH 6.0. Injections were performed at 25° C. at a flow rate of 80 µl/min.

Figure 16:
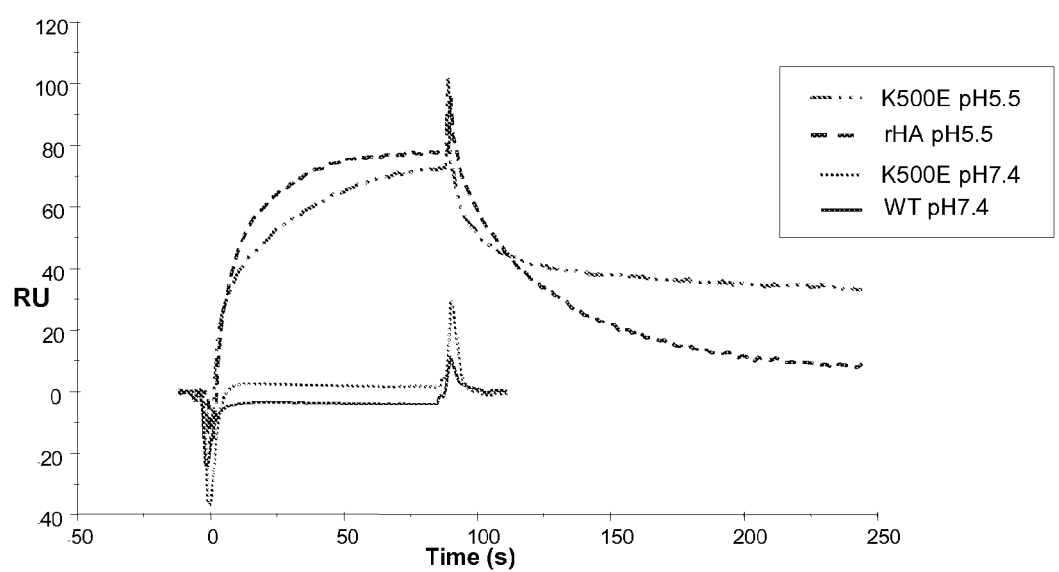

FIG. 16 shows SPR sensorgrams of HSA mutant K500E compared with wild-type HSA. Ten µM of HSA mutant K500E injected over immobilized shFcRn at pH 5.75. Injections were performed at 25° C. at a flow rate of 30 µl/min.

Figure 17:
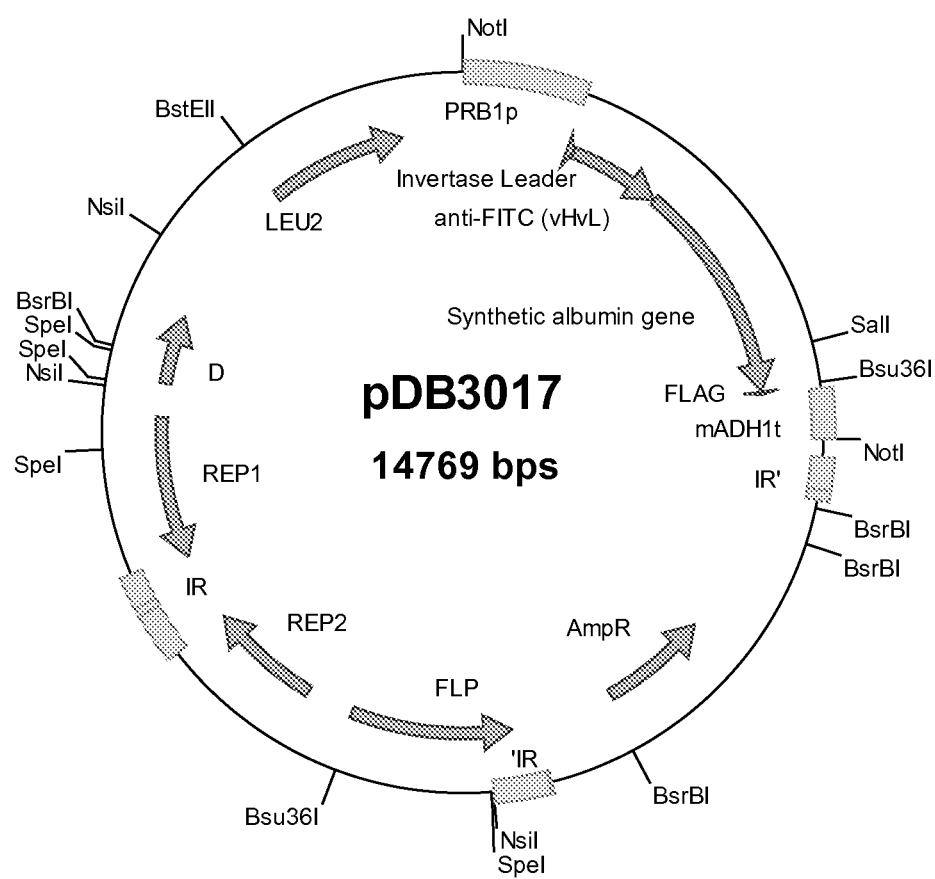

FIG. 17 shows a restriction map of the expression plasmid pDB3017

Figure 18:
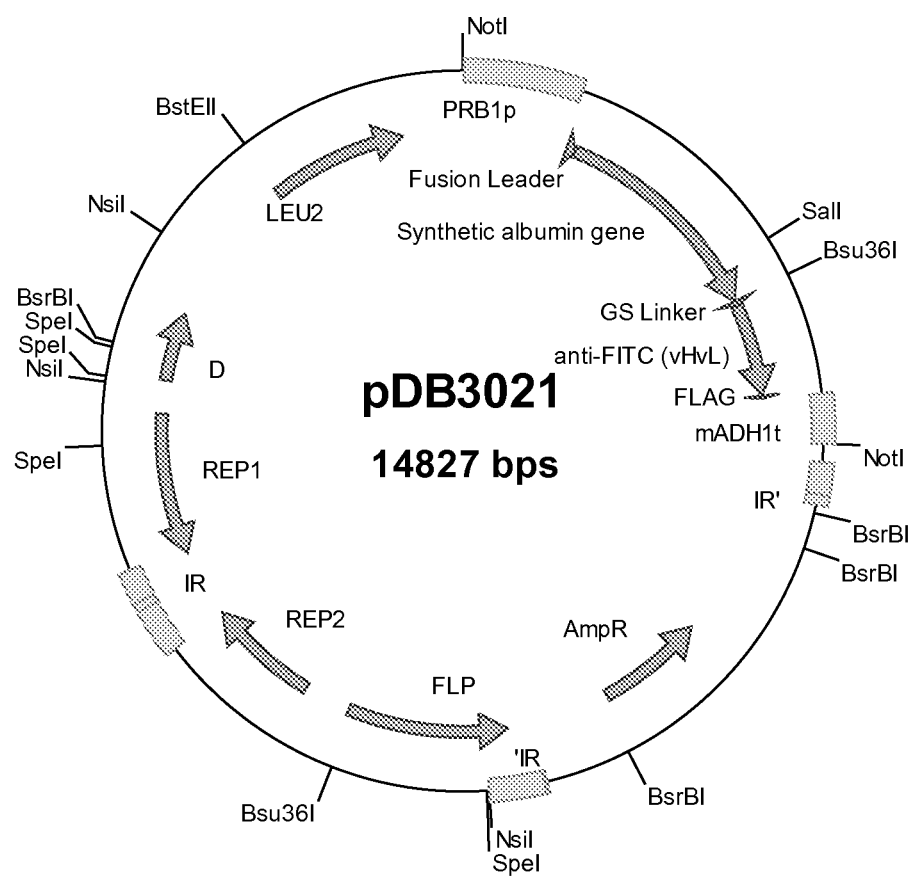

FIG. 18 shows a restriction map of the expression plasmid pDB3021

Figure 19:
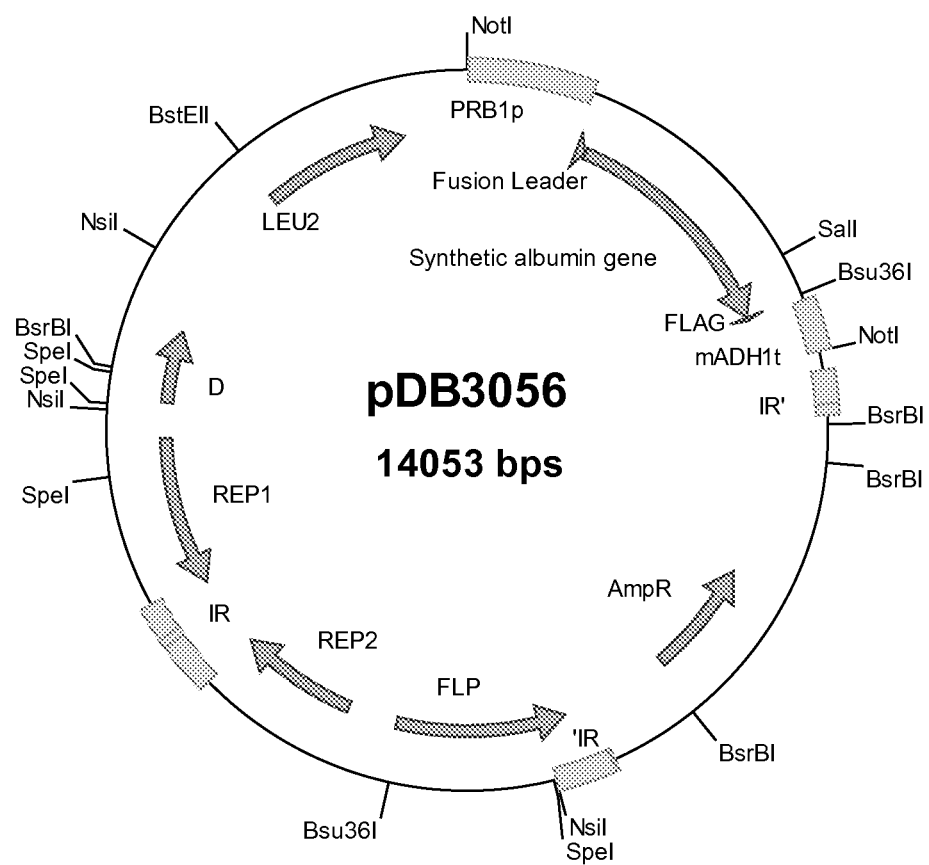

FIG. 19 shows a restriction map of the expression plasmid pDB3056

Figure 20:
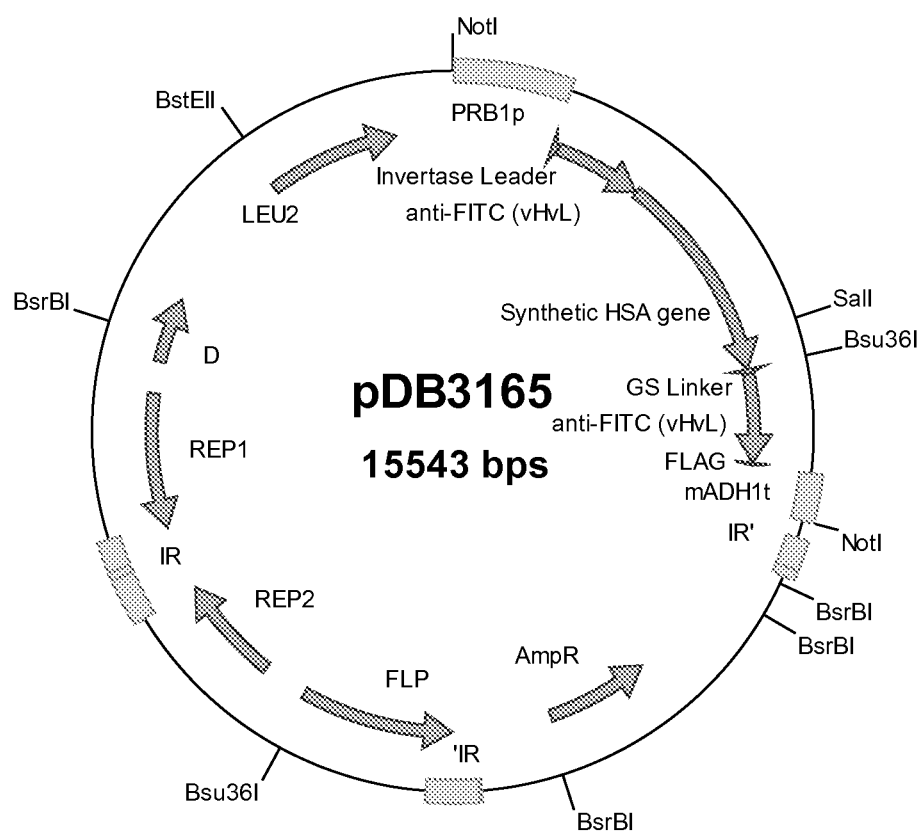

FIG. 20 shows a restriction map of the expression plasmid pDB3165

Figure 21:
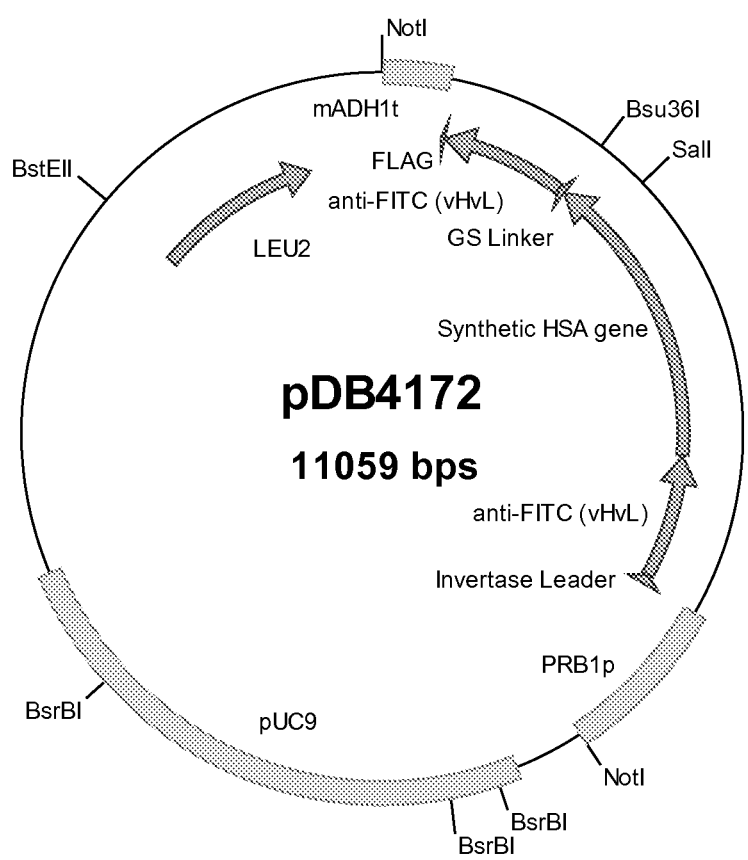

FIG. 21 shows a restriction map of the expression plasmid pDB4172

Figure 22:
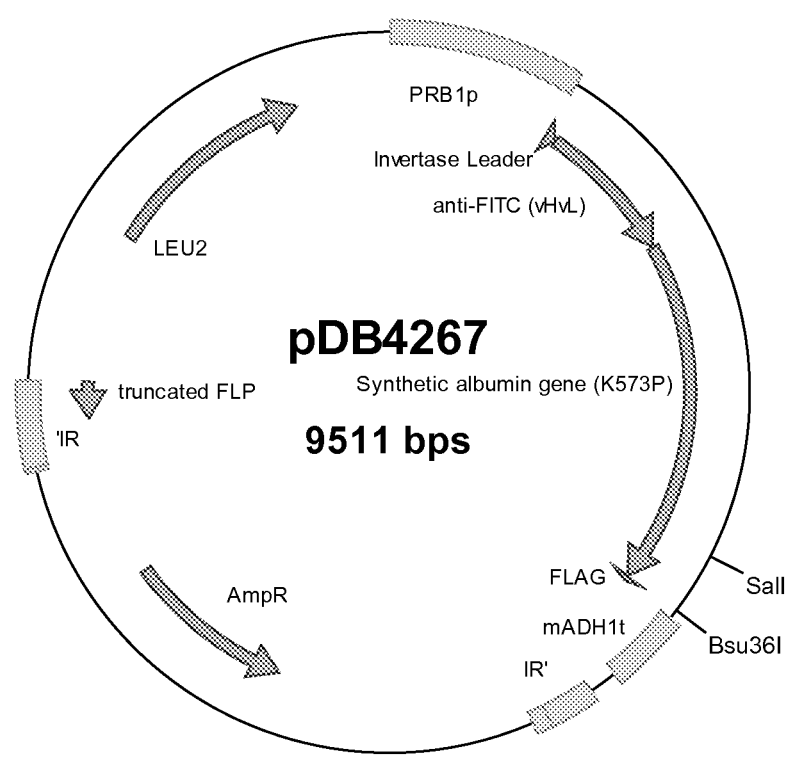

FIG. 22 shows a restriction map of the expression plasmid pDB4267

Figure 23:
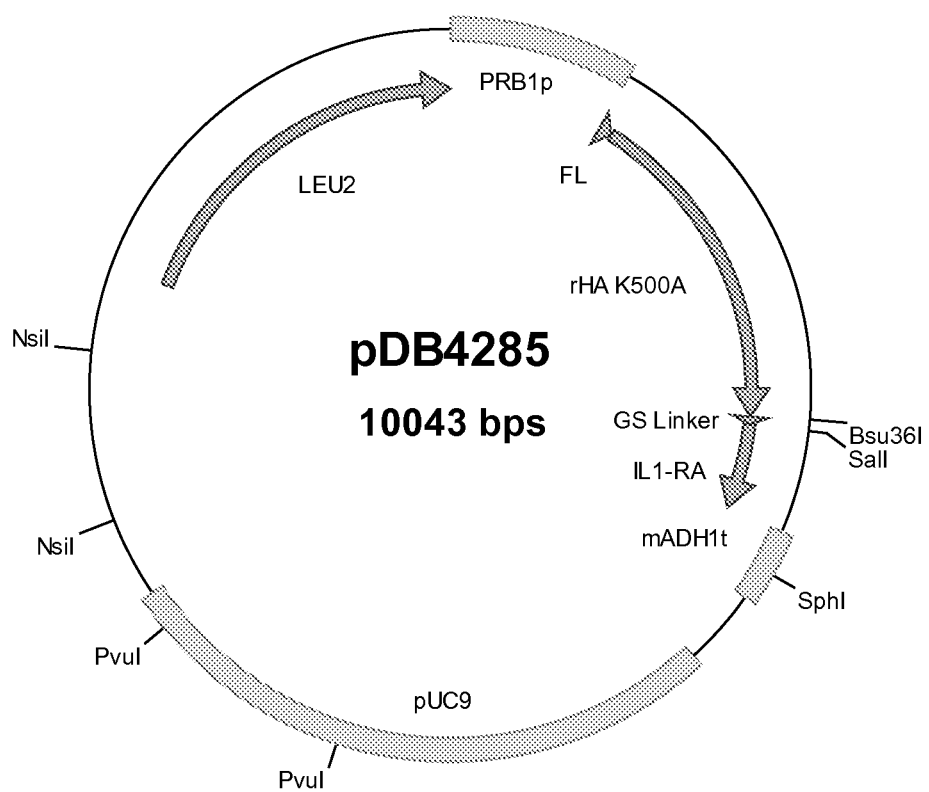

FIG. 23 shows a restriction map of the expression plasmid pDB4285

Figure 24A:
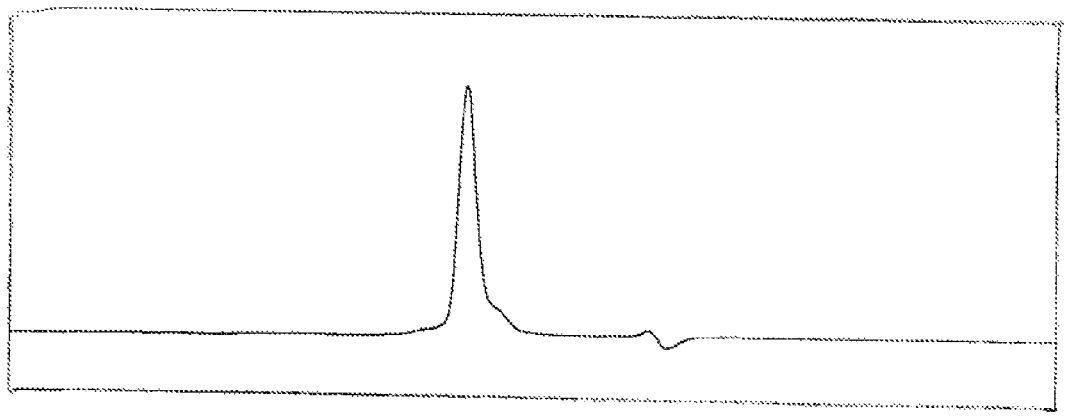
Figure 24B:
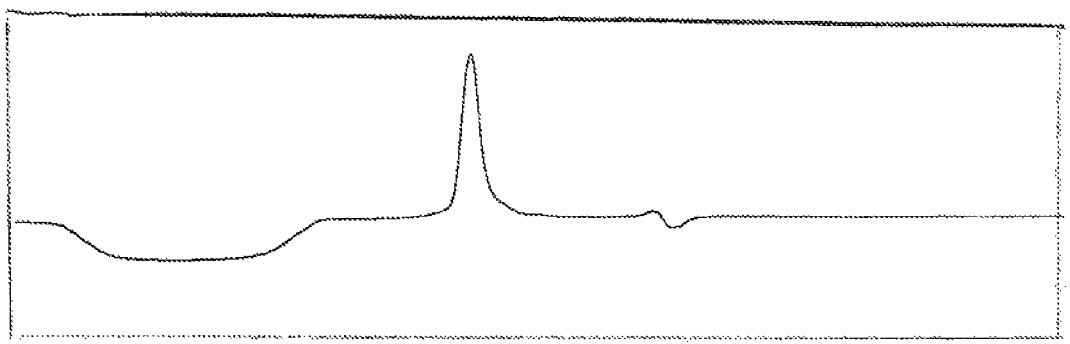

FIG. 24(a) and FIG. 24(b) show, respectively, a GP-HPLC chromatogram of WT HSA and mutant K573P HRP conjugates for shFcRn analysis. Injections of 25 µL were made onto a TSK G3000SWXL column (Tosoh Bioscience) as described in materials and methods.

Figure 25:
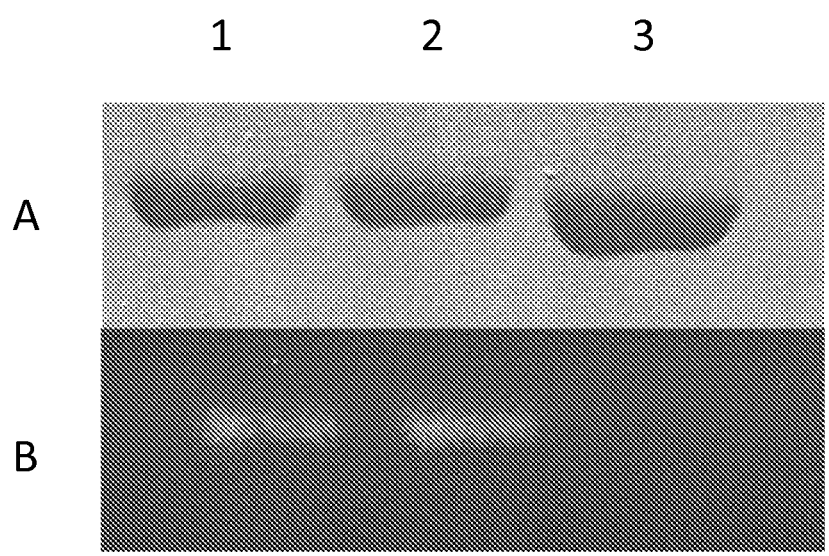

FIG. 25 shows SDS PAGE separation followed by both visual (A) and ultraviolet (B) detection of the Fluorescein conjugated albumin. HSA::F5M (Lane 1), K573P::F5M (Lane 2) and rHA standard (Lane 3).

Figure 26:
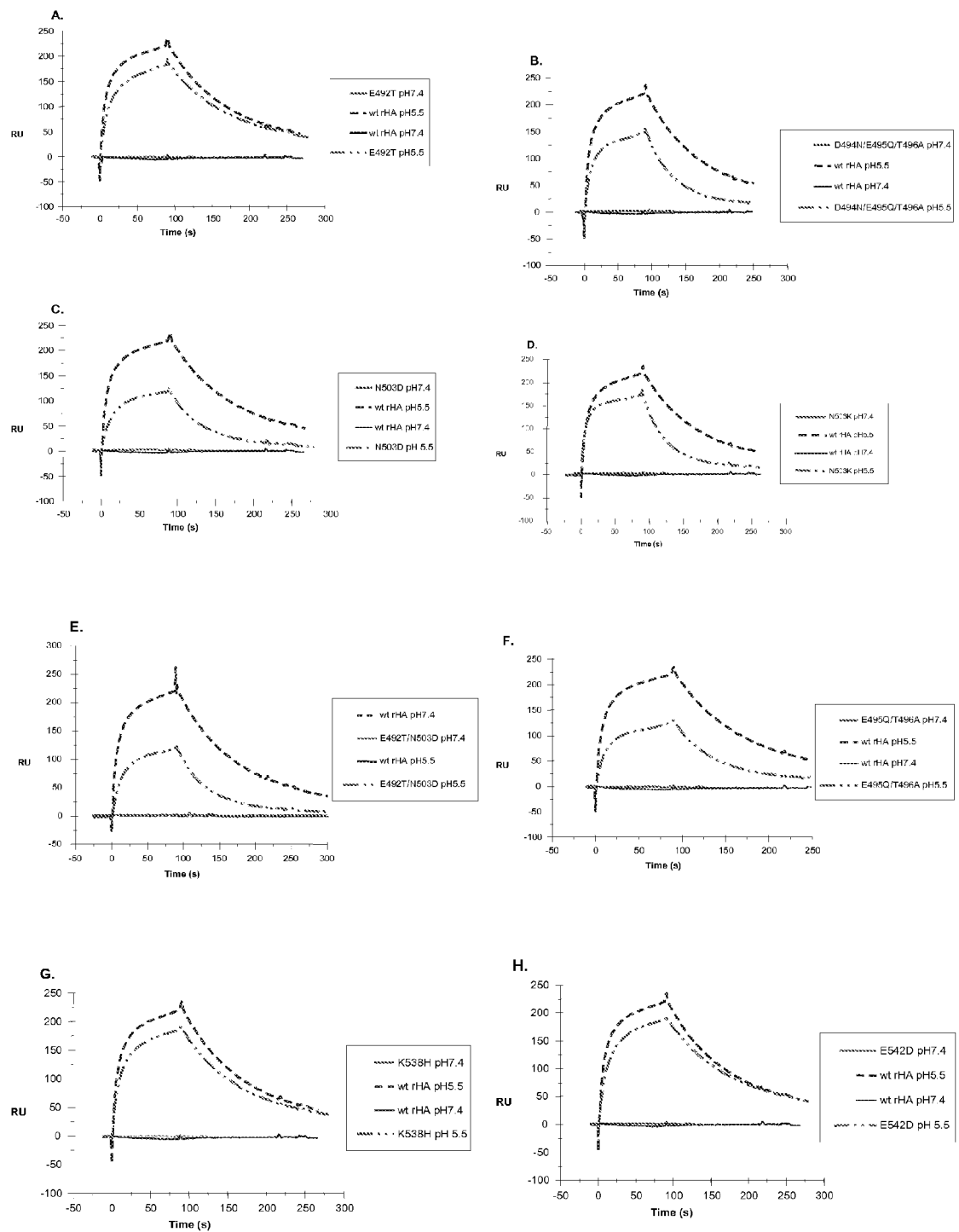

FIG. 26 shows shFcRn binding properties of HSA variants. 10 µM of WT rHA and E492T(A), WT rHA and D494N/E495Q/T496A(B), WT rHA and N503D(C), WT rHA and N503K(D), WT rHA and E492T/N503D(E), WT rHA and E495Q/T496A(F), WT rHA and K538H(G), WT rHA and E492D(H) injected over immobilised shFcRn at pH 5.5.

Figure 27:
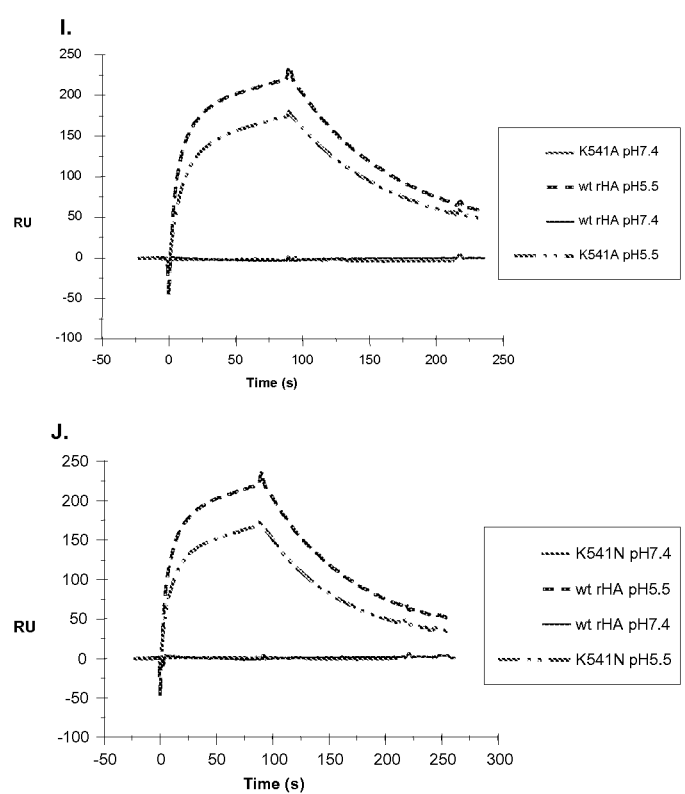

FIG. 27 shows shFcRn binding properties of HSA variants. 10 µM of WT rHA and K541A(I) and WT rHA and K541N(J) were injected over immobilised shFcRn at pH 5.5.

Figure 28:
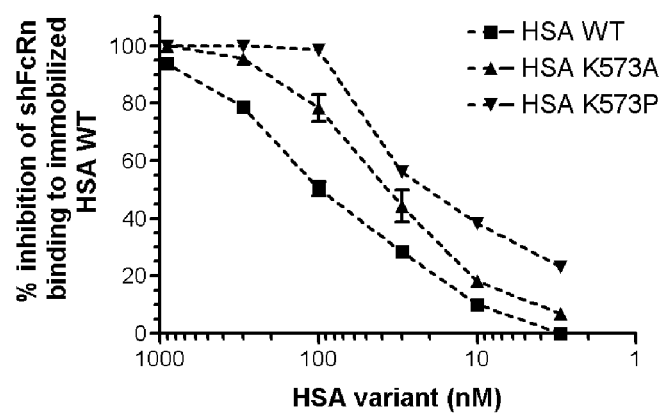

FIG. 28 shows competitive binding of K573A and K573P measured by injecting shFcRn (100 nM) alone or pre-incubated with different amounts of HSA K573A and K573P over immobilized HSA (~2500 RU) at pH 6.0.

Figure 29:
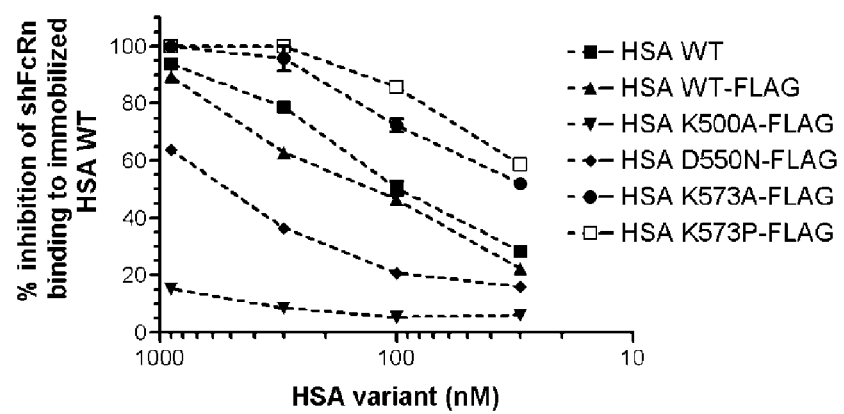

FIG. 29 shows competitive binding of HSA-FLAG variants measured by injecting shFcRn (100 nM) alone or together with different amounts of HSA-FLAG variants over immobilized HSA (~2500 RU) at pH 6.0.

Figure 30:
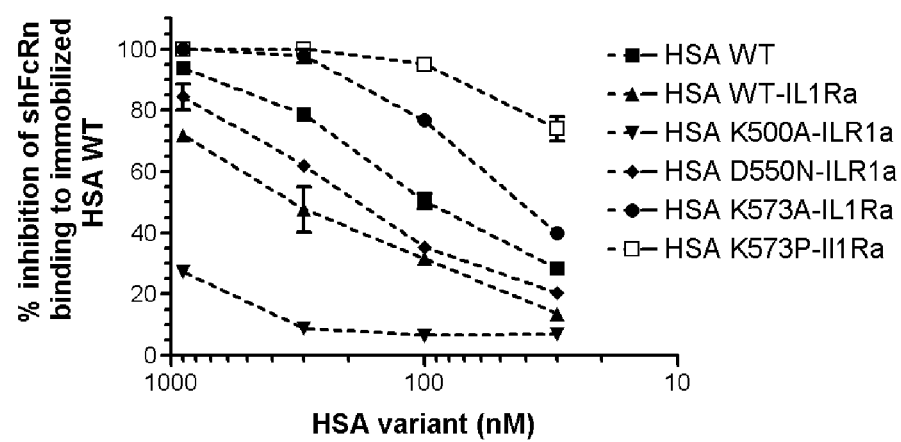

FIG. 30 shows competitive binding of HSA-IL1Ra variants measured by injecting shFcRn (100 nM) alone or together with different amounts of HSA-IL1Ra variants over immobilized HSA (~2500 RU) at pH 6.0.

Figure 31:
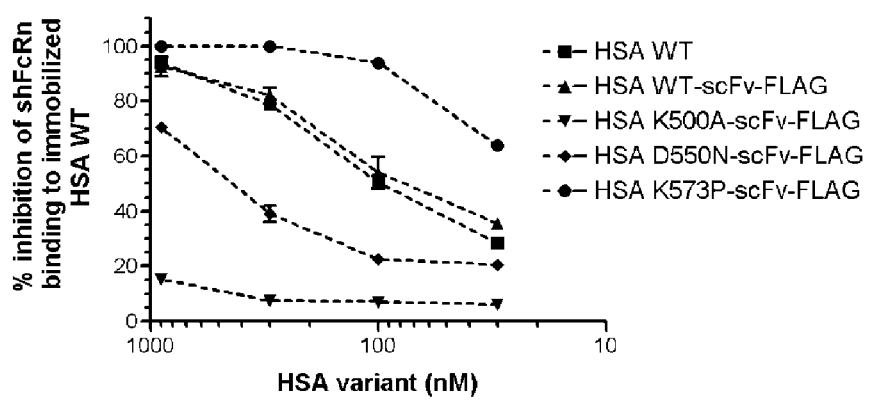
Figure 31:
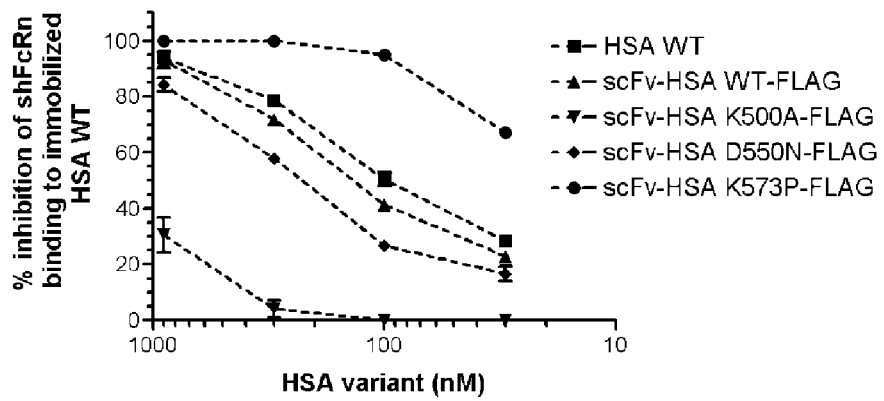

FIG. 31 shows competitive binding of scFv-fused HSA variants measured by injecting shFcRn (100 nM) alone or together with different amounts of (A) scFv-HSA-FLAG variants or (B) HSA-scFv-FLAG variants over immobilized HSA (~2500 RU) at pH 6.0.

Figure 32:
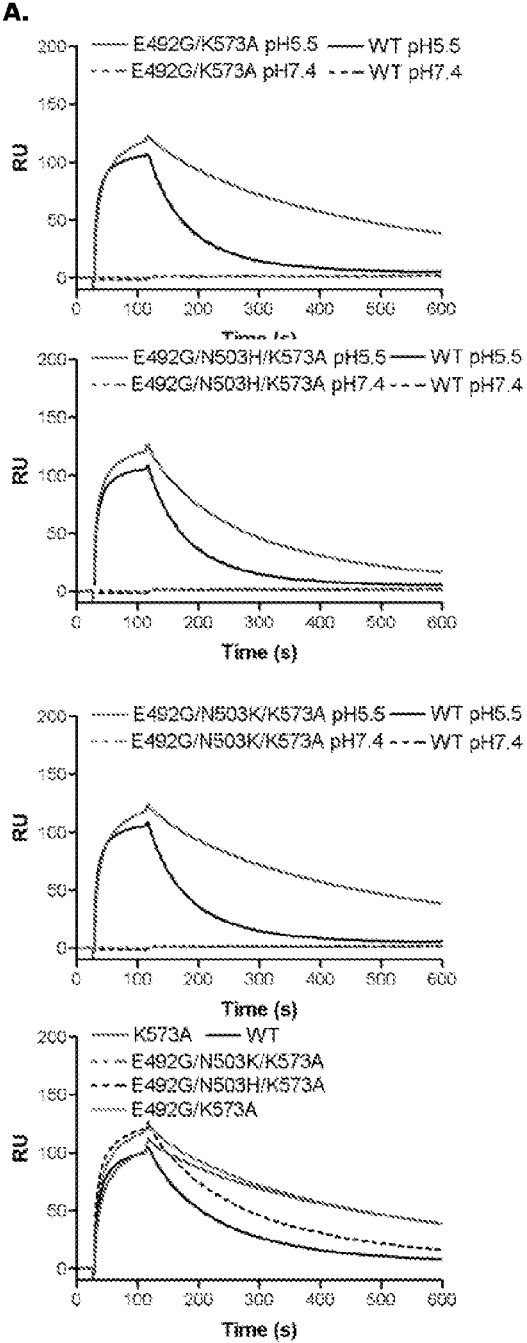
Figure 32:
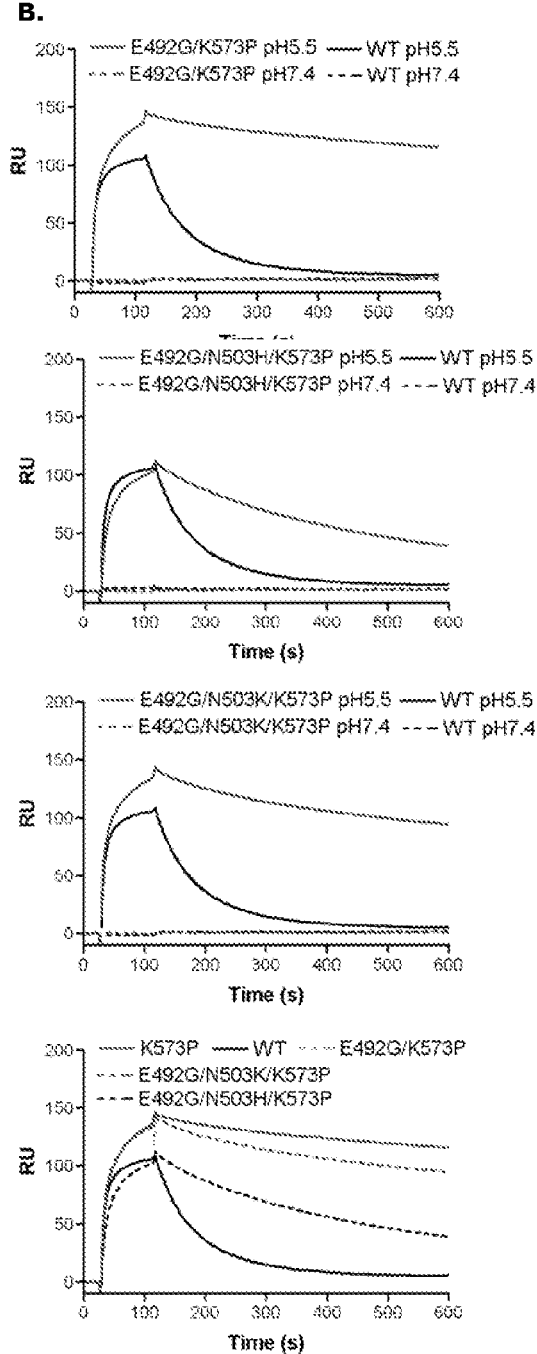

FIG. 32 shows binding of HSA, single, double and triple mutant variants to shFcRn. Samples of 10 µM of each HSA variant were injected over immobilized shFcRn at pH 5.5 or pH 7.4.

DETAILED DESCRIPTION OF THE INVENTION

The present invention relates to isolated variants of albumin or fragments thereof, or fusion polypeptides comprising variant albumin or fragments thereof, of a parent albumin, comprising an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of the mature polypeptide of SEQ ID NO: 2, wherein the variant is not the variant consisting of SEQ ID NO: 2 with the substitution D494N, E501K, K541E, D550G,A, K573E or K574N.

The alteration at one or more position may independently be selected among substitutions, insertions and deletions, where substitution are preferred.

DEFINITIONS

Variant: The term "variant" means a polypeptide derived from a parent albumin by one or more alteration(s), i.e., a substitution, insertion, and/or deletion, at one or more (several) positions. A substitution means a replacement of an amino acid occupying a position with a different amino acid; a deletion means removal of an amino acid occupying a position; and an insertion means adding 1 or more, preferably 1-3 amino acids immediately adjacent to an amino acid occupying a position.

Mutant: The term "mutant" means a polynucleotide encoding a variant.

Wild-Type Albumin: The term "wild-type" (WT) albumin means albumin having the same amino acid sequence as naturally found in an animal or in a human being.

Parent or Parent albumin The term "parent" or "parent albumin" means an albumin to which an alteration is made by the hand of man to produce the albumin variants of the present invention. The parent may be a naturally occurring (wild-type) polypeptide or an allele thereof, or even a variant thereof.

FcRn and shFcRn: The term "FcRn" means the human neonatal Fc receptor (FcRn). shFcRn is a soluble recombinant form of FcRn.

smFcRn: The term "smFcRn" is a soluble recombinant form of the mouse neonatal Fc Receptor.

Isolated variant: The term "isolated variant" means a variant that is modified by the hand of man and separated completely or partially from at least one component with which it naturally occurs. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE or GP-HPLC.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well known recombinant methods and by purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 585 of SEQ ID NO: 2, with the inclusion of any post-translational modifications.

Mature polypeptide coding sequence: The term "mature polypeptide coding sequence" means a polynucleotide that encodes a mature albumin polypeptide. In one aspect, the mature polypeptide coding sequence is nucleotides 1 to 1758 of SEQ ID NO: 1.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labelled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of an albumin and/or an internal region of albumin that has retained the ability to bind to FcRn. Fragments may consist of one uninterrupted sequence derived from HSA or it may comprise two or more sequences derived from HSA. The fragments according to the invention have a size of more than approximately 20 amino acid residues, preferably more than 30 amino acid residues, more preferred more than 40 amino acid residues, more preferred more than 50 amino acid residues, more preferred more than 75 amino acid residues, more preferred more than 100 amino acid residues, more preferred more than 200 amino acid residues, more preferred more than 300 amino acid residues, even more preferred more than 400 amino acid residues and most preferred more than 500 amino acid residues.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of its translated polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences within the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Plasma half-life: Plasma half-life is ideally determined in vivo in suitable individuals. However, since it is time consuming and expensive and there inevitable are ethical concerns connected with doing experiments in animals or man it is desirable to use an in vitro assay for determining whether plasma half-life is extended or reduced. It is known that the binding of albumin to its receptor FcRn is important for plasma half-life and the correlation between receptor binding and plasma half-life is that a higher affinity of albumin to its receptor leads to longer plasma half-life. Thus for the present invention a higher affinity of albumin to FcRn is considered indicative of an increased plasma half-life and a lower affinity of albumin to its receptor is considered indicative of a reduced plasma half-life.

In this application and claims the binding of albumin to its receptor FcRn is described using the term affinity and the expressions "stronger" or "weaker". Thus, it should be understood that a molecule having a higher affinity to FcRn than HSA is considered to bind stronger to FcRn than HSA and a molecule having a lower affinity to FcRn than HSA is considered to bind weaker to FcRn than HSA.

The terms "longer plasma half-life" or "shorter plasma half-life" and similar expressions are understood to be in relationship to the corresponding parent albumin molecule. Thus, a longer plasma half-life with respect to a variant albumin of the invention means that the variant has longer plasma half-life than the corresponding albumin having the same sequences except for the alteration(s) in positions corresponding to 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2.

Conventions for Designation of Variants

For purposes of the present invention, the mature polypeptide disclosed in SEQ ID NO: 2 is used to determine the corresponding amino acid residue in another albumin. The amino acid sequence of another albumin is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another albumin can be confirmed by an alignment of multiple polypeptide sequences using "ClustalW" (Larkin et al., 2007, *Bioinformatics* 23: 2947-2948).

When the other polypeptide (or protein) has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as inputs to a neural network that predicts the structural fold for a query sequence. Similarly, the method of Gough et al., 2000, *J. Mol. Biol.* 313: 903-919, can be used to align a sequence of unknown structure within the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the albumin variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, for example the substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. The Figures also use ("/"), e.g., "E492T/N503D" this should be viewed as interchangeable with ("+").

Deletions.

For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" represents a substitution of arginine with tyrosine or glutamic acid at position 170. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Parent Albumin

Albumins are proteins and constitute the most abundant protein in plasma in mammals and albumins from a long number of mammals have been characterized by biochemical methods and/or by sequence information. Several albumins, e.g., human serum albumin (HSA), have also been characterized crystallographically and the structure determined.

HSA is a preferred albumin according to the invention and is a protein consisting of 585 amino acid residues and has a molecular weight of 67 kDa. In its natural form it is not glycosylated. The amino acid sequence of HSA is shown in SEQ ID NO: 2. The skilled person will appreciate that natural alleles may exist having essentially the same properties as HSA but having one or more amino acid changes compared to SEQ ID NO: 2, and the inventors also contemplate the use of such natural alleles as parent albumin according to the invention.

Albumins have generally a long plasma half-life of approximately 20 days or longer, e.g., HSA has a plasma half-life of 19 days. It is known that the long plasma half-life of HSA is mediated via interaction with its receptor FcRn, however, an understanding or knowledge of the exact mechanism behind the long half-life of HSA is not essential for the present invention.

According to the invention the term "albumin" means a protein having the same, or very similar three dimensional structure as HSA and having a long plasma half-life. As examples of albumin proteins according to the invention can be mentioned human serum albumin, primate serum albumin, (such as chimpanzee serum albumin, gorilla serum albumin), rodent serum albumin (such as hamster serum albumin, guinea pig serum albumin, mouse albumin and rat serum albumin), bovine serum albumin, equine serum albumin, donkey serum albumin, rabbit serum albumin, goat serum albumin, sheep serum albumin, dog serum albumin, chicken serum albumin and pig serum albumin. HSA as disclosed in SEQ ID NO: 2 or any naturally occurring allele thereof, is the preferred albumin according to the invention.

The parent albumin, a fragment thereof, or albumin part of a fusion polypeptide comprising albumin or a fragment thereof according to the invention has generally a sequence identity to the sequence of HSA shown in SEQ ID NO: 2 of at least 60%, preferably at least 70%, preferably at least 80%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, more preferred at least 96%, more preferred at least 97%, more preferred at least 98% and most preferred at least 99%.

The parent preferably comprises or consists of the amino acid sequence of SEQ ID NO: 2. In another aspect, the parent comprises or consists of the mature polypeptide of SEQ ID NO: 2.

In another embodiment, the parent is an allelic variant of the mature polypeptide of SEQ ID NO: 2.

In a second aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the mature polypeptide coding sequence of SEQ ID NO: 1, or (iii) the full-length complementary strand of (i) or (ii) (J. Sambrook, E. F. Fritsch, and T. Maniatis, 1989, *Molecular Cloning, A Laboratory Manual,* 2d edition, Cold Spring Harbor, N.Y.).

The polynucleotide of SEQ ID NO: 1 or a subsequence thereof, as well as the amino acid sequence of SEQ ID NO: 2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labelled for detecting the corresponding gene (for example, with $^{32}$P, $^{3}$H, $^{35}$S, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is used in a Southern blot.

For purposes of the present invention, hybridization indicates that the polynucleotide hybridizes to a labelled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 1 to 1785 of SEQ ID NO: 1. In another aspect, the nucleic acid probe is a polynucleotide that encodes the polypeptide of SEQ ID NO: 2 or a fragment thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the parent is encoded by a polynucleotide with a sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%, which encodes a polypeptide which is able to function as an albumin. In an embodiment, the parent is encoded by a polynucleotide comprising or consisting of SEQ ID NO: 1.

Preparation of Variants

In a further aspect the invention relates to a method for preparing a variant albumin, fragment thereof, or fusion polypeptide comprising variant albumin or a fragment thereof comprising the steps of:
  a. Identifying one or more amino acid residue positions being important for the binding of albumin to FcRn, in an albumin or a fragment thereof or the albumin part of a fusion polypeptide comprising albumin or a fragment thereof;
  b. Providing a nucleic acid encoding said albumin, the fragment thereof or the albumin part of a fusion polypeptide comprising albumin or the fragment thereof;
  c. Modifying the nucleic acid provided in b., so that the one or more (several) amino acid residue located at the positions identified in a., are deleted or substituted or inserted with a different amino acid;
  d. Expressing the modified nucleic acid in a suitable host cell; and
  e. Recovering the variant albumin, the fragment thereof or the fusion polypeptide comprising variant albumin or the fragment thereof.

The identification of one or more amino acid residue positions being important for the binding of albumin to FcRn, in albumin, fragment thereof or the albumin part of a fusion polypeptide can be done in several ways including, but not limited to, random mutagenesis followed by analysis of the generated mutants and comparison with the non-mutated parent molecule, and identification based on structural considerations optionally followed by generation of variants having the identified alterations and comparison with the non-mutated patent molecule.

A preferred method for identification of one or more amino acid residue positions to be changed to in order to prepare a variant HSA having an altered binding to FcRn compared with natural HSA, comprises the following steps:
  i) Identifying a non-human albumin having a different binding property to FcRn;
  ii) Identifying the amino acid residues of the human serum albumin interacting with FcRn;
  iii) Comparing the primary and/or the tertiary structure of the identified non-human albumin and human serum albumin with respect to the amino acid residues identified in step ii) and identifying the amino acid residues that differ between said non-human albumin and human serum albumin as being responsible for the observed binding difference; and
  iv) Optionally preparing variants of HSA at the positions identified in step iii) and confirming that the prepared variants have altered binding to FcRn compared with HSA.

Step i) above may be done using the SPR assay described below. However, the skilled person will appreciate that other methods may be used to identify non-human albumins having different binding properties to FcRn than HSA, and that the method is not dependent on how the non-human albumin, having different binding properties to FcRn, has been identified.

In one preferred embodiment the identified non-human albumin has a stronger binding to FcRn than HSA. Examples of non-human albumins having stronger binding to FcRn than HSA include donkey serum albumin, rabbit serum albumin, dog serum albumin, hamster serum albumin, guinea pig serum albumin, mouse serum albumin and rat serum albumin. Step ii) may be accomplished by considering the structure of FcRn, HSA and the binding complex of these two. In the absence of an available structure of the binding complex it is possible to use a model where the HSA structure is docked into the structure of the FcRn structure and thereby identify amino acid residues of HSA interacting with FcRn.

In another preferred embodiment the identified non-human albumin has a weaker binding to FcRn than HSA. Examples of non-human albumins having weaker binding to FcRn than HSA include bovine serum albumin, goat serum albumin, sheep serum albumin and chicken serum albumin. Step ii) may be accomplished by considering the structure of FcRn, HSA and the binding complex of these two. In absence of an available structure of the binding complex it is possible to use a model where the HSA structure is docked into the structure of the FcRn structure and thereby identify residues of HSA interacting with FcRn.

In this invention and claims, an amino acid residues of HSA interacting with FcRn is considered any amino acid residues of HSA being located less than 10 Å from an amino acid in the FcRn or any amino acid residue that is involved in a hydrogen bond, a salt bridge or a polar or nonpolar interaction with an amino acid residue that is located less than 10 Å from an amino acid in the FcRn. Preferably the amino acid in HSA residues are located less than 10 Å from amino acids in the FcRn, more preferred less than 6 Å from amino acids in the FcRn and most preferred less than 3 Å from amino acids in the FcRn.

Step iii) and iv) can be done using techniques well known to the skilled person.

The present invention also relates to methods for obtaining a variant albumin or fragments thereof, or fusion polypeptides comprising the variant albumin or fragments thereof, or associates of variant albumin or fragment thereof comprising: (a) introducing into a parent albumin or fragments thereof, or fusion polypeptides comprising the parent albumin or fragments thereof an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of the mature polypeptide of SEQ ID NO: 2; and (b) recovering the variant albumin or fragments thereof, or fusion polypeptides comprising the variant albumin or fragments thereof.

The variants can be prepared by those skilled persons using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting ligation of the plasmid and insert to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide sub sequences may then be shuffled.

Variants

The present invention also provides variant albumins or fragments thereof, or fusion polypeptides comprising the variant albumin or fragments thereof, of a parent albumin, comprising an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2, wherein each alteration is independently a substitution, insertion or deletion with the provision that the and the variant is not SEQ ID NO: 2 having the substitution D494N, E501K, K541E, D550G,A, K573E or K574N.

The variant albumin, a fragment thereof, or albumin part of a fusion polypeptide comprising variant albumin or a fragment thereof according to the invention has generally a sequence identity the sequence of HSA shown in SEQ ID NO: 2 of at least 60%, preferably at least 70%, preferably at least 80%, preferably at least 85%, preferably at least 90%, more preferred at least 95%, more preferred at least 96%, more preferred at least 97%, more preferred at least 98% and most preferred at least 99%.

In one aspect, the number of alterations in the variants of the present invention is 1-20, e.g., 1-10 and 1-5, such as 1, 2, 3, 4, 5, 6, 7, 8, 9 or 10 alterations.

The variant albumin, a fragment thereof or fusion polypeptide comprising the variant albumin or fragment thereof has altered plasma half-life compared with the corresponding parent albumin, fragment thereof, or fusion polypeptide comprising the variant albumin or fragment thereof.

In a particular preferred embodiment the parent albumin is HSA and the variant albumin, a fragment thereof or fusion polypeptide comprising the variant albumin or fragment thereof has altered plasma half-life compared with the HSA, the corresponding fragment or fusion polypeptide comprising HSA or fragment thereof.

The correlation between binding of albumin to its receptor and plasma half-life has been realized by the present inventors based on the natural occurring allele of HSA D494N. The inventors have analyzed this allele and found that it has a lower affinity to its receptor FcRn.

Further, it has been disclosed that a transgenic mouse having the natural mouse FcRn replaced with human FcRn has a higher serum albumin level than normal mouse; see (J Exp Med. (2003) 197(3):315-22). The inventors have discovered that human FcRn has a higher affinity to mouse serum albumin than mouse FcRn has to mouse serum albumin and, therefore, the observed increase in serum albumin in the transgenic mice corresponds with a higher affinity between serum albumin and its receptor, confirming the correlation between albumin binding to FcRn and plasma half-life. In addition, variants of albumin that have little or no binding to FcRn have been shown to have reduced half-life in a mouse model, Kenanova et al (2009) J. Nucl. Med.; 50 (Supplement 2):1582).

One way to determine whether the affinity of a variant albumin to FcRn is higher or lower than the parent albumin is to use the Surface Plasmon Resonance assay (SPR) as described below. The skilled person will understand that other methods might be useful to determine whether the affinity of a variant albumin to FcRn is higher or lower than the affinity of the parent albumin to FcRn, e.g., determination and comparison of the binding constants KD. Thus, according to the invention variant albumins having a KD that is lower than the KD for natural HSA is considered to have a higher plasma half-life than HSA and variant albumins having a KD that is higher than the KD for natural HSA is considered to have a lower plasma half-life than HSA.

The variants of albumin or fragments thereof or fusion polypeptides comprising albumin or fragments thereof comprise one or more alterations, such as substitutions, deletions or insertions at one or more (several) positions corresponding to the positions in HSA selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584. The substitution may be any substitution where the amino acid in the natural albumin sequence is substituted with a different amino acid selected among the remaining 19 natural occurring amino acids.

In one aspect, a variant comprises an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2. In another aspect, a variant comprises an alteration at two positions corresponding to any of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2. In another aspect, a variant comprises an alteration at three positions corresponding to any of positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2. In another aspect, a variant comprises an alteration at each position corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2.

In another aspect, the variant comprises the substitution Q417A,H of the mature polypeptide of SEQ ID NO: 2. In another aspect, the variant comprises the substitution H440Q of the mature polypeptide of SEQ ID NO: 2. In another aspect, the variant comprises the substitution H464Q of the mature polypeptide of SEQ ID NO: 2. In another aspect, the variant comprises the substitution A490D of the mature polypeptide of SEQ ID NO: 2. In another aspect, the variant comprises the substitution E492G, T,P,H of the mature polypeptide of SEQ ID NO: 2. In another aspect, the variant comprises the substitution V493P,L of the mature polypeptide of SEQ ID NO: 2. In another aspect, the variant comprises the substitution D494N,Q,A,E,P of the mature polypeptide of SEQ ID NO: 2. In another aspect, the variant comprises the substitution E495Q,A of the mature polypeptide of SEQ ID NO: 2. In another aspect, the variant comprises the substitution T496A of the mature polypeptide of SEQ ID NO: 2. In another aspect, the variant comprises the substitution P499A of the mature polypeptide of SEQ ID NO: 2. In another aspect, the variant comprises the substitution K500E,G,D,A,S,C,P,H,F,N,W,T,M,Y,V,Q,L,I,R of the mature polypeptide of SEQ ID NO: 2. In another aspect, the variant comprises the substitution E501A,P,Q of the mature polypeptide of SEQ ID NO: 2. In another aspect, the variant comprises the substitution N503K,D,H of the mature polypeptide of SEQ ID NO: 2. In another aspect, the variant comprises the substitution A504E of the mature polypeptide of SEQ ID NO: 2. In another aspect, the variant comprises the substitution E505K, D of the mature polypeptide of SEQ ID NO: 2. In another aspect, the variant comprises the substitution T506F, S of the mature polypeptide of SEQ ID NO: 2. In another aspect, the variant comprises the substitution H510Q of the mature polypeptide of SEQ ID NO: 2. In another aspect, the variant comprises the substitution H535Q of the mature polypeptide of SEQ ID NO: 2. In another aspect, the variant comprises the substitution K536A of the mature polypeptide of SEQ ID NO: 2. In another aspect, the variant comprises the substitution P537A of the mature polypeptide of SEQ ID NO: 2. In another aspect, the variant comprises the substitution K538A,H of the mature polypeptide of SEQ ID NO: 2. In another aspect, the variant comprises the substitution T540S of the mature polypeptide of SEQ ID NO: 2. In another aspect, the variant comprises the substitution K541A, D,G,N,E of the mature polypeptide of SEQ ID NO: 2. In another aspect, the variant comprises the substitution E542P,D of the mature polypeptide of SEQ ID NO: 2. In another aspect, the variant comprises the substitution D550N of the mature polypeptide of SEQ ID NO: 2. In another aspect, the variant comprises the substitution K573Y,W,P,H, F,V,I,T,N,S,G,M,C,A,E,Q,R,L,D of the mature polypeptide of SEQ ID NO: 2. In another aspect, the variant comprises the substitution K574N of the mature polypeptide of SEQ ID NO: 2. In another aspect, the variant comprises the substitution Q580K of the mature polypeptide of SEQ ID NO: 2. In another aspect, the variant comprises the substitution L575F of the mature polypeptide of SEQ ID NO: 2. In another aspect, the variant comprises the substitution A577T,E of the mature polypeptide of SEQ ID NO: 2. In another aspect, the variant comprises the substitution A578R,S of the mature polypeptide of SEQ ID NO: 2. In another aspect, the variant comprises the substitution S579C,T of the mature polypeptide of SEQ ID NO: 2. In another aspect, the variant comprises the substitution Q580K of the mature polypeptide of SEQ ID NO: 2. In another aspect, the variant comprises the substitution A581D of the mature polypeptide of SEQ ID NO: 2. In another aspect, the variant comprises the substitution A582T of the mature polypeptide of SEQ ID NO: 2. In another aspect, the variant comprises the substitution G584A of the mature polypeptide of SEQ ID NO: 2.

In one aspect, the variant comprises an alteration at a position corresponding to position 417. In another aspect, the amino acid at a position corresponding to position 417 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or His. In another aspect, the variant comprises the substitution Q417A, H of the mature polypeptide of SEQ ID NO: 2.

In another aspect, the variant comprises an alteration at a position corresponding to position 440. In another aspect, the amino acid at a position corresponding to position 440 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution H440Q of the mature polypeptide of SEQ ID NO: 2.

In another aspect, the variant comprises an alteration at a position corresponding to position 464. In another aspect, the amino acid at a position corresponding to position 464 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution H464Q of the mature polypeptide of SEQ ID NO: 2.

In another aspect, the variant comprises an alteration at a position corresponding to position 490 In another aspect, the amino acid at a position corresponding to position 490 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises the substitution A490G of the mature polypeptide of SEQ ID NO: 2.

In another aspect, the variant comprises an alteration at a position corresponding to position 492. In another aspect, the amino acid at a position corresponding to position 492 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another aspect, the variant comprises the substitution E492G of the mature polypeptide of SEQ ID NO: 2.

In another aspect, the variant comprises an alteration at a position corresponding to position 493. In another aspect, the amino acid at a position corresponding to position 493 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises the substitution V493P of the mature polypeptide of SEQ ID NO: 2.

In another aspect, the variant comprises an alteration at a position corresponding to position 494. In another aspect, the amino acid at a position corresponding to position 494 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Gln or Ala. In another aspect, the variant comprises the substitution D494N,Q, A of the mature polypeptide of SEQ ID NO: 2.

In another aspect, the variant comprises an alteration at a position corresponding to position 495. In another aspect, the amino acid at a position corresponding to position 495 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln or Ala. In another aspect, the variant comprises the substitution E495Q or A of the mature polypeptide of SEQ ID NO: 2.

In another aspect, the variant comprises an alteration at a position corresponding to position 496. In another aspect, the amino acid at a position corresponding to position 496 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution T496A of the mature polypeptide of SEQ ID NO: 2.

In another aspect, the variant comprises an alteration at a position corresponding to position 499. In another aspect, the amino acid at a position corresponding to position 499 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution P499A of the mature polypeptide of SEQ ID NO: 2.

In another aspect, the variant comprises an alteration at a position corresponding to position 500. In another aspect, the amino acid at a position corresponding to position 500 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution K500E,G,D,A,S,C,P,H,F,N,W,T,M,Y,V,Q,L,I,R of the mature polypeptide of SEQ ID NO: 2.

In another aspect, the variant comprises an alteration at a position corresponding to position 501. In another aspect, the amino acid at a position corresponding to position 501 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or Gln to reduce affinity and Pro to increase affinity. In another aspect, the variant comprises the substitution E501A, Q, P of the mature polypeptide of SEQ ID NO: 2.

In another aspect, the variant comprises an alteration at a position corresponding to position 503. In another aspect, the amino acid at a position corresponding to position 503 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp or Lys or His. In another aspect, the variant comprises the substitution N503D, K, H of the mature polypeptide of SEQ ID NO: 2.

In another aspect, the variant comprises an alteration at a position corresponding to position 504. In another aspect, the amino acid at a position corresponding to position 504 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises the substitution A504 of the mature polypeptide of SEQ ID NO: 2.

In another aspect, the variant comprises an alteration at a position corresponding to position 505. In another aspect, the amino acid at a position corresponding to position 505 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises the substitution E505D of the mature polypeptide of SEQ ID NO: 2.

In another aspect, the variant comprises an alteration at a position corresponding to position 506. In another aspect, the amino acid at a position corresponding to position 506 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises the substitution T506S,F of the mature polypeptide of SEQ ID NO: 2.

In another aspect, the variant comprises an alteration at a position corresponding to position 510. In another aspect, the amino acid at a position corresponding to position 510 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant comprises the substitution H510Q of the mature polypeptide of SEQ ID NO: 2.

In another aspect, the variant comprises an alteration at a position corresponding to position 535. In another aspect, the amino acid at a position corresponding to position 535 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant comprises the substitution H535Q of the mature polypeptide of SEQ ID NO: 2.

In another aspect, the variant comprises an alteration at a position corresponding to position 536. In another aspect, the amino acid at a position corresponding to position 536 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution K536A of the mature polypeptide of SEQ ID NO: 2.

In another aspect, the variant comprises an alteration at a position corresponding to position 537. In another aspect, the amino acid at a position corresponding to position 537 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution P537A of the mature polypeptide of SEQ ID NO: 2.

In another aspect, the variant comprises an alteration at a position corresponding to position 538. In another aspect, the amino acid at a position corresponding to position 538 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution K538H, A of the mature polypeptide of SEQ ID NO: 2.

In another aspect, the variant comprises an alteration at a position corresponding to position 540. In another aspect, the amino acid at a position corresponding to position 540 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises the substitution T540S of the mature polypeptide of SEQ ID NO: 2.

In another aspect, the variant comprises an alteration at a position corresponding to position 541. In another aspect, the amino acid at a position corresponding to position 541 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly, Asp or Ala. In another aspect, the variant comprises the substitution K541G, D A, N of the mature polypeptide of SEQ ID NO: 2.

In another aspect, the variant comprises an alteration at a position corresponding to position 542. In another aspect, the amino acid at a position corresponding to position 542 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp or Pro. In another aspect, the variant comprises the substitution E542D, P of the mature polypeptide of SEQ ID NO: 2.

In another aspect, the variant comprises an alteration at a position corresponding to position 550. In another aspect, the amino acid at a position corresponding to position 550 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn to reduce affinity, preferably with Glu to increase affinity.

In another aspect, the variant comprises an alteration at a position corresponding to position 573. In another aspect, the amino acid at a position corresponding to position 573 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr, Trp, Pro, His. Phe, Val, Ile, Thr, Asn, Ser, Gly, Met, Cys, Ala, Glu, Gln, Arg, Leu, Asp. In another aspect, the variant comprises the substitution K573Y,W,P,H,F,V,I,T,N,S, G,M,C,A,E,Q,R,L,D of the mature polypeptide of SEQ ID NO: 2.

In another aspect, the variant comprises an alteration at a position corresponding to position 574. In another aspect, the amino acid at a position corresponding to position 574 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the variant comprises the substitution K574N of the mature polypeptide of SEQ ID NO: 2.

In another aspect, the variant comprises an alteration at a position corresponding to position 575. In another aspect, the amino acid at a position corresponding to position 575 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant comprises the substitution L575F of the mature polypeptide of SEQ ID NO: 2.

In another aspect, the variant comprises an alteration at a position corresponding to position 577. In another aspect, the amino acid at a position corresponding to position 577 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr or Glu. In another aspect, the variant comprises the substitution A577TE of the mature polypeptide of SEQ ID NO: 2.

In another aspect, the variant comprises an alteration at a position corresponding to position 578. In another aspect, the amino acid at a position corresponding to position 578 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg or Ser. In another aspect, the variant comprises the substitution A578R,S of the mature polypeptide of SEQ ID NO: 2.

In another aspect, the variant comprises an alteration at a position corresponding to position 579. In another aspect, the amino acid at a position corresponding to position 579 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys or Thr. In another aspect, the variant comprises the substitution S579C,T of the mature polypeptide of SEQ ID NO: 2.

In another aspect, the variant comprises an alteration at a position corresponding to position 580. In another aspect, the amino acid at a position corresponding to position 580 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another aspect, the variant comprises the substitution Q580K of the mature polypeptide of SEQ ID NO: 2.

In another aspect, the variant comprises an alteration at a position corresponding to position 581. In another aspect, the amino acid at a position corresponding to position 581 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises the substitution A581D of the mature polypeptide of SEQ ID NO: 2.

In another aspect, the variant comprises an alteration at a position corresponding to position 582. In another aspect, the amino acid at a position corresponding to position 582 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises the substitution A582T of the mature polypeptide of SEQ ID NO: 2.

In another aspect, the variant comprises an alteration at a position corresponding to position 584. In another aspect, the amino acid at a position corresponding to position 584 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution G584A of the mature polypeptide of SEQ ID NO: 2.

In another aspect, the variant comprises an alteration at positions corresponding to positions 494 and 496 in SEQ ID NO: 2, such as those described above.

In another aspect, the variant comprises alterations at positions corresponding to positions 492 and 493 in SEQ ID NO: 2, such as those described above.

In another aspect, the variant comprises alterations at positions corresponding to positions 494 and 417 in SEQ ID NO: 2, such as those described above.

In another aspect, the variant comprises alterations at positions corresponding to positions 492 and 503 in SEQ ID NO: 2, such as those described above.

In another aspect, the variant comprises alterations at positions corresponding to positions 492 and 573 in SEQ ID NO: 2, such as those described above.

In another aspect, the variant comprises alterations at positions corresponding to positions 492, 503, and 573 in SEQ ID NO: 2, such as those described above.

In one embodiment the variant albumin or fragments thereof, or fusion polypeptides comprising the variant albumin or fragments thereof according to the invention contains one substitution at a position corresponding to a position in HSA selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 2 provided that the variant albumin is not the variant consisting of SEQ ID NO: 2 with the substitution D494N, E501K, K541E, D550G,A, K573E or K574N. The variant albumin, fragment thereof or fusion polypeptides comprising variant albumin or a fragment thereof according to the invention may comprise additional substitutions, insertions or deletions at one or more (several) positions corresponding to other positions in HSA.

In another embodiment the variant albumin or fragments thereof, or fusion polypeptides comprising variant albumin or fragments thereof according to the invention contains two, three, four, five, six, seven, eight, nine, ten, eleven, twelve, thirteen, fourteen, fifteen, sixteen, seventeen, eighteen, nineteen, twenty or even more substitutions at positions corresponding to positions in HSA selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of SEQ ID NO: 2. The variant albumin or fragments thereof, or fusion polypeptides comprising variant albumin or fragments thereof according to the invention may comprise additional substitutions, insertions or deletions at positions corresponding to other positions in HSA.

In a further embodiment the variants of albumin or fragments thereof, or fusion polypeptides comprising variant albumin or a fragment thereof according to the invention have a plasma half-life that is longer than the plasma half-life of the parent albumin fragment thereof or fusion polypeptide comprising the parent albumin or a fragment thereof. Examples according to this embodiment include variants of albumin or fragments thereof, or fusion polypeptides comprising variant albumin or a fragment thereof comprising a substitution in the position corresponding to 492, 503, 542, 550, 573, 574, 580, 581, 582 or 584 in SEQ ID NO: 2. Preferred substitutions according to this embodiment of the invention include the substitution of the amino acid residue in the position corresponding to 492 in SEQ ID NO: 2 with a G residue, substitution of the amino acid residue in the position corresponding to 503 in SEQ ID NO: 2 with a H or a K residue, substitution of the amino acid residue in the position corresponding to 550 in SEQ ID NO: 2 with an E residue, the substitution of the amino acid residue in a position corresponding to 573 in SEQ ID NO: 2 with an Y,W,P,H,F,V,I,T,N,S,G,M,C,A,E,Q,R,L or a D, the substitution of the amino acid residue in a position corresponding to 574 in SEQ ID NO: 2 with an N residue, or the substitution of the amino acid residue in the position corresponding to 580 in SEQ ID NO: 2 with an K residue. Other preferred variants have a substitution in the position corresponding to 492 in SEQ ID NO: 2 with a G residue and a substitution in the position corresponding to 573 in SEQ ID NO: 2 with an A or a P residue. Other preferred variant has a number of substitutions corresponding to position 492 in SEQ ID NO: 2 with an H residue in position 503 in SEQ ID NO: 2.

Other preferred variants have a substitution in the position corresponding to 492 in SEQ ID NO: 2 with a G residue and a substitution in the position corresponding to position 503 in SEQ ID NO: 2 corresponding to a H or a K and a substitution in position 573 in SEQ ID NO: 2 with an A or a P residue.

In a further embodiment the variants of albumin or fragments thereof, or fusion polypeptides comprising variant albumin or fragments thereof according to the invention have a plasma half-life that is shorter than the plasma half-life of the parent albumin fragment thereof or fusion polypeptide comprising the parent albumin or a fragment thereof. Examples according to this embodiment include variants of albumin or fragments thereof, or fusion polypeptides comprising variant albumin or a fragment thereof comprising a substitution in the position corresponding to 417, 440, 494, 495, 496, 499, 500, 501, 536, 537, 538, 541, 494+496 or 492+493 in SEQ ID NO: 2. Preferred substitutions include the substitutions corresponding to Q417A, H440Q, D494E+Q417H, D494N,Q,A, E495Q,A, T496A, D494N+T496A or, P499A, K500A, E501A, E501Q, K536A, P537A, K538A, K541G, K541A K541D or D550N in SEQ ID NO: 2.

In another embodiment of the invention the variants of albumin or fragments thereof, or fusion polypeptides comprising variant albumin or a fragment thereof according to the invention have lost their ability to bind FcRn. In this connection variants of albumin or fragments thereof, or fusion polypeptides comprising variant albumin or fragments thereof is considered to have lost the ability to bind FcRn if the measured resonance units for the variant in the SPR assay described below is less than 10% of the measured resonance units for the corresponding parent albumin or fragment thereof. Examples according to this embodiment include variants of albumin or fragments thereof, or fusion polypeptides comprising variant albumin or fragments thereof comprising a substitution at a position corresponding to 464, 500, 510 or 535 in SEQ ID NO: 2. Preferred substitutions include the substitutions corresponding to H464Q, K500A,P,C,S,A, D.G H510Q or H535Q in SEQ ID NO: 2.

In addition to the one or more substitutions at one or more positions corresponding to positions 417, 464, 490, 492, 493, 494, 495, 496, 499, 500, 501, 503, 504, 505, 506, 510, 535, 536, 537, 538, 540, 541, 542, 550, 573, 574, 580 581, 582 and 584 in SEQ ID NO: 2 the variant albumin or fragments thereof, or fusion polypeptides comprising variant albumin or fragments thereof according to the invention may contain additional substitutions, deletions or insertions in other positions of the molecules. Such additional substitutions, deletions or insertions may be useful in order to alter other properties of the molecules such as but not limited to altered glycosylation; introduction of reactive groups of the surface such a thiol groups, removing/generating a carbamoylation site; etc.

Residues that might be altered in order to provide reactive residues on the surface and which advantageously could be applied to the present invention has been disclosed in the unpublished patent application WO 2010/092135 (Included by reference). Particular preferred residues include the positions corresponding to positions in SEQ ID NO: 2.

As examples of alterations that can be made in SEQ ID NO: 2 or in corresponding positions in other albumins in order to provide a reactive thiol group on the surface includes alterations corresponding to following alterations in SEQ ID NO: 2: L585C, D1C, A2C, D562C, A364C, A504C, E505C, T79C, E86C, D129C, D549C, A581C, D121C, E82C, S270C, A578C, L595LC, D1DC, A2AC, D562DC, A364AC, A504AC, E505EC, T79TC, E86EC, D129DC, D549DC, A581AC, A581AC, D121DC, E82EC, S270SC, A579AC, C360*, C316*, C75*, 0168*, C558*, C361*, C91*, C124*, C169* and C567*. Alternatively a cysteine residue may be added to the N or C terminal of albumin.

Polynucleotides

The present invention also relates to isolated polynucleotides that encode any of the variants of the present invention.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

In a yeast host, useful promoters are obtained from the genes for *Saccharomyces cerevisiae* enolase (ENO-1), *Saccharomyces cerevisiae* protease A (PRA1), *Saccharomyces cerevisiae* protease B (PRB1), *Saccharomyces cerevisiae* translation elongation factor (TEF1), *Saccharomyces cerevisiae* translation elongation factor (TEF2), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for yeast host cells are obtained from the genes for *Saccharomyces cerevisiae* enolase, *Saccharomyces cerevisiae* cytochrome C (CYC1), *Saccharomyces cerevisiae* alcohol dehydrogenase (ADH1) and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

Where both signal peptide and propeptide regions are present at the N-terminus of a variant, the propeptide region is positioned next to the N-terminus of the variant and the signal peptide region is positioned next to the N-terminus of the propeptide region.

Methods of Production

The variants of the present invention can be prepared using techniques well known to the skilled person. One convenient way is by cloning nucleic acid encoding the parent albumin or a fragment thereof or fusion polypeptide comprising albumin or a fragment thereof, modifying said nucleic acid to introduce the desired substitution(s) at one or more (several) positions corresponding to positions 417, 464, 490, 492, 493, 494, 495, 496, 499, 500, 501, 503, 504, 505, 506, 510, 535, 536, 537, 538, 540, 541, 542, 550, 573, 574 and 580 in SEQ ID NO: 2, where the variant is not the variant consisting of SEQ ID NO:2 with the substitution D494N, E501K, K541E, D550G,A, K573E or K574N, preparing a suitable genetic construct where the modified nucleic acid is placed in operative connection with suitable regulatory genetic elements, such as promoter, terminator, activation sites, ribosome binding sites etc., introducing the genetic construct into a suitable host organism, culturing the transformed host organism under conditions leading to expression of the variant and recovering the variant. All these techniques are known in the art and it is within the skills of the average practitioner to design a suitable method for preparing a particular variant according to the invention.

The variant polypeptide of the invention may also be connected to a signal sequence in order to have the variant polypeptide secreted into the growth medium during culturing of the transformed host organism. It is generally advantageous to have the variant polypeptide secreted into the growth medium in order to ease recovery and purification.

Techniques for preparing variant polypeptides have also been disclosed in WO 2009019314 (included by reference) and these techniques may also be applied to the present invention.

Albumins have been successfully expressed as recombinant proteins in a range of hosts including fungi (including but not limited to *Aspergillus* (WO06066595), *Kluyveromyces* (Fleer 1991, *Bio/technology* 9, 968-975), *Pichia* (Kobayashi 1998 *Therapeutic Apheresis* 2, 257-262) and *Saccharomyces* (Sleep 1990, *Bio/technology* 8, 42-46)), bacteria (Pandjaitab 2000, *J. Allergy Clin. Immunol.* 105, 279-285)), animals (Barash 1993, *Transgenic Research* 2, 266-276) and plants (including but not limited to potato and tobacco (Sijmons 1990, *Bio/technology* 8, 217 and Farran 2002, *Transgenic Research* 11, 337-346). The variant polypeptide of the invention is preferably produced recombinantly in a suitable host cell. In principle any host cell capable of producing a polypeptide in suitable amounts may be used and it is within the skills of the average practitioner to select a suitable host cell according to the invention. A preferred host organism is yeast, preferably selected among Saccharomycacae, more preferred *Saccharomyces cerevisiae*.

The variant polypeptides of the invention may be recovered and purified from the growth medium using a combination of known separation techniques such as filtration, centrifugation, chromatography, and affinity separation techniques etc. It is within the skills of the average practitioner to purify the variants of the invention using a particular combination of such known separation steps. As an example of purification techniques that may be applied to the variants of the present invention can be mentioned the teaching of WO0044772.

The variant polypeptides of the invention may be used for delivering a therapeutically beneficial compound to an animal or a human individual in need thereof. Such therapeutically beneficial compounds include, but are not limited, to labels and readily detectable compounds for use in diagnostics, such as various imaging techniques; pharmaceutical active compounds such as drugs, or specifically binding moieties such as antibodies. The variants of the invention may even be connected to two or more different therapeutically beneficial compounds, e.g., an antibody and a drug, which gives the combined molecule the ability to bind specifically to a desired target and thereby provide a high concentration of the connected drug at that particular target.

Fusion Polypeptides

The variants of albumin or fragments thereof according to the invention may also be fused with a non-albumin polypeptide fusion partner. The fusion partner may in principle be any polypeptide but generally it is preferred that the fusion partner is a polypeptide having therapeutic or diagnostic properties. Fusion polypeptides comprising albumin or fragments thereof are known in the art. It has been found that such fusion polypeptide comprising albumin or a fragment thereof and a fusion partner polypeptide have a longer plasma half-life compared to the unfused fusion partner polypeptide. According to the invention it is possible to alter the plasma half-life of the fusion polypeptides according to the invention compared to the corresponding fusion polypeptides of the prior art.

One or more therapeutic polypeptides may be fused to the N-terminus, the C-terminus of albumin, inserted into a loop in the albumin structure or any combination thereof. It may or it may not comprise linker sequences separating the various components of the fusion polypeptide.

Teachings relating to fusions of albumin or a fragment thereof are known in the art and the skilled person will appreciate that such teachings can also be applied to the present invention. WO 2001/79271 A and WO 2003/59934 A also contain examples of therapeutic polypeptides that may be fused to albumin or fragments thereof, and these examples apply also to the present invention.

Conjugates

The variants of albumin or fragments thereof according to the invention may be conjugated to a second molecule using techniques known within the art. Said second molecule may comprise a diagnostic moiety, and in this embodiment the conjugate may be useful as a diagnostic tool such as in imaging; or the second molecule may be a therapeutic compound and in this embodiment the conjugate may be used for therapeutic purposes where the conjugate will have the therapeutic properties of the therapeutic compound as well as the long plasma half-life of the albumin. Conjugates of albumin and a therapeutic molecule are known in the art and it has been verified that such conjugates have long plasma half-life compared with the non-conjugated, free therapeutic molecule as such. The conjugates may conveniently be linked via a free thio group present on the surface of HSA (amino acid residue 34 of mature HSA) using well known chemistry.

In one particular preferred aspect the variant albumin or fragment thereof is conjugated to a beneficial therapeutic compound and the conjugate is used for treatment of a condition in a patient in need thereof, which condition is responsive to the particular selected therapeutic compound. Techniques for conjugating such a therapeutically compound to the variant albumin or fragment thereof are known in the art. WO 2009/019314 discloses examples of techniques suitable for conjugating a therapeutically compound to a polypeptide which techniques can also be applied to the present invention. Further WO 2009/019314 discloses examples of compounds and moieties that may be conjugated to substituted transferrin and these examples may also be applied to the present invention. The teaching of WO 2009/019314 is included herein by reference.

HSA contains in its natural form one free thiol group that conveniently may be used for conjugation. As a particular embodiment within this aspect the variant albumin or fragment thereof may comprise further modifications provided to generate additional free thiol groups on the surface. This has the benefit that the payload of the variant albumin or fragment thereof is increased so that more than one molecule of the therapeutic compound can be conjugated to each molecule of variant albumin or fragment thereof, or two or more different therapeutic compounds may be conjugated to each molecule of variant albumin or fragment thereof, e.g., a compound having targeting properties such as an antibody specific for example a tumour; and a cytotoxic drug conjugated to the variant albumin or fragment thereof thereby creating a highly specific drug against a tumour. Teaching of particular residues that may be modified to provide for further free thiol groups on the surface can be found in copending patent application WO 2010/092135, which is incorporated by reference.

Associates

The variants of albumin or fragments thereof may further be used in form of "associates". In this connection the term "associate" is intended to mean a compound comprising a variant of albumin or a fragment thereof and another compound bound or associated to the variant albumin or fragment thereof by non-covalent binding. As an example of such an associate can be mentioned an associate consisting variant albumin and a lipid associated to albumin by a hydrophobic interaction. Such associates are known in the art and they may be prepared using well known techniques. As an example of a preferred associate according to the invention can be mentioned an associate comprising variant albumin and paclitaxel.

Other Uses

The variant albumin or fragments thereof or fusion polypeptides comprising variant albumin or fragments thereof according to the invention have the benefit that their plasma half-life is altered compared to the parent albumin or fragments thereof or fusion polypeptides comprising parent albumin or fragments thereof. This has the advantage that the plasma half-life of conjugates comprising variant albumin or a fragment thereof or fusion polypeptide comprising variant albumin or a fragment thereof, or an associate comprising variant albumin or a fragment thereof according to the invention can be selected in accordance with the particular therapeutic purpose.

For example for a conjugate, associate or fusion polypeptide used for imaging purposes in animals or human beings, where the imaging moiety has an very short half-life and a conjugate or a fusion polypeptide comprising HSA has a plasma half-life that is far longer than needed for the imaging purposes it would be advantageous to use a variant albumin or fragment thereof of the invention having a shorter plasma half-life than the parent albumin or fragment thereof, to provide conjugates of fusion polypeptides having a plasma half-life that is sufficiently long for the imaging purpose but sufficiently short to be cleared form the body of the particular patient on which it is applied.

In another example for a conjugate, an associate or fusion polypeptide comprising a therapeutic compound effective to treat or alleviate a particular condition in a patient in need for such a treatment it would be advantageous to use the variant albumin or fragment thereof having a longer plasma half-life than the parent albumin or fragment thereof, to provide associates or conjugates or fusion polypeptides having longer plasma half-lives which would have the benefit that the administration of the associate or conjugate or fusion polypeptide of the invention would be needed less frequently or reduced dose with less side affects compared to the situation where the parent albumin or associates thereof or fragment thereof was used.

In a further aspect the invention relates to compositions comprising the variant albumin, associates thereof or fragment thereof, variant albumin fragment or associates thereof or fusion polypeptide comprising variant albumin or fragment thereof according to the invention. The compositions are preferably pharmaceutical compositions. The composition may be prepared using techniques known in the area such as disclosed in recognized handbooks within the pharmaceutical field.

In a particular embodiment the compositions comprise a variant albumin or a fragment thereof according to the invention and a compound comprising a pharmaceutically beneficial moiety and an albumin binding domain (ABD). According to the invention ABD means a site, moiety or domain capable of binding to circulating albumin in vivo and thereby conferring transport in the circulation of the ABD and any compound or moiety bound to said ABD. ABD's are known in the art and have been shown to bind very tight to albumin so a compound comprising an ABD bound to albumin will to a certain extent behave as a single molecule. The inventors have realized by using the variant albumin or fragment thereof according to the invention together with a compound comprising a pharmaceutically beneficial moiety and an ABD makes it possible to alter the plasma half-life of the compound comprising a pharmaceutically beneficial moiety and an ABD compared to the situation where said compound were injected as such in a patient having need thereof or administered in a formulation comprising natural albumin or a fragment thereof.

The variant albumin or fragments thereof, conjugates comprising variant albumin or a fragment thereof or fusion polypeptide comprising variant albumin or a fragment thereof, or an associate comprising variant albumin or a fragment thereof according to the invention may also be incorporated into nano- or microparticles using techniques well known within the art. A preferred method for preparing nano- or microparticles that may be applied to the variant albumins or fragments thereof according to the invention is disclosed in WO 2004/071536, which is incorporated herein by reference.

Compositions

The present invention is also directed to the use of a variant of albumin or a fragment thereof or fusion polypeptides comprising variant albumin or fragments thereof, or a conjugate comprising a variant of albumin or a fragment thereof, or an associate comprising a variant of albumin or a fragment thereof for the manufacture of a pharmaceutical composition, where in the variant of albumin or a fragment thereof or fusion polypeptides comprising variant albumin or fragments thereof, or a conjugate comprising a variant of albumin or a fragment thereof, or an associate comprising a variant of albumin or a fragment thereof has an altered plasma half-life compared with HSA or the corresponding fragment thereof or fusion polypeptide comprising HSA or fragment thereof or conjugate comprising HSA.

In this connection the corresponding fragment of HSA is intended to mean a fragment of HSA that aligns with and has same number of amino acids as the fragment of the variant albumin with which it is compared. Similarly the corresponding fusion polypeptide comprising HSA or conjugate comprising HSA is intended to mean molecules having same size and amino acid sequence as the fusion polypeptide of conjugate comprising variant albumin, with which it is compared.

Preferably the variant of albumin or a fragment thereof or fusion polypeptides comprising variant albumin or fragments thereof, fragment thereof, or a conjugate comprising a variant of albumin or a fragment thereof has a plasma half-life that is higher than the plasma half-life of HSA or the corresponding fragment thereof or fusion polypeptide comprising HSA or fragment thereof.

Alternatively, this may be expressed as the variant of albumin or a fragment thereof or fusion polypeptides comprising variant albumin or fragments thereof, fragment thereof, or a conjugate comprising a variant of albumin or a fragment thereof has a KD to FcRn that is lower that the corresponding KD for HSA or the corresponding fragment thereof or fusion polypeptide comprising HSA or fragment thereof. Preferably, is KD for the variant of albumin or a fragment thereof or fusion polypeptides comprising variant albumin or fragments thereof, fragment thereof, or a conjugate comprising a variant of albumin or a fragment thereof less than 0.9×KD for HSA, more preferred less than 0.5×KD for HSA, more preferred less than 0.1×KD for HSA, even more preferred less than 0.05×KD for HSA, even more preferred less than 0.02×KD for HSA and most preferred less than 0.01×KD for HSA.

The variant of albumin or a fragment thereof or fusion polypeptides comprising variant albumin or fragments thereof, fragment thereof, or a conjugate comprising a variant of albumin or a fragment thereof is preferably the variant of albumin or a fragment thereof or fusion polypeptides comprising variant albumin or fragments thereof, fragment thereof, or a conjugate comprising a variant of albumin or a fragment thereof according to the invention.

The present invention is further described by the following examples that should not be construed as limiting the scope of the invention.

EXAMPLES

Materials and Methods

ELISA:

Wells were coated with wild-type HSA or variants diluted in phosphate buffered saline (PBS) to stated concentrations, incubated overnight at 4 C. and then blocked with 4% skimmed milk (Acumedia) for 1 hour at room temperature. The wells were then washed four times with PBS/0.005% TWEEN® 20 brand detergent (PBS/T) pH 6.0 before glutathione-S-transferase (GST)-fused shFcRn (0.5 µg/ml) as described in FEBS J. 2008 August; 275(16):4097-110. pre-incubated with an horseradish peroxidase (HRP)-conjugated polyclonal anti-GST from goat (1:5000; GE Healthcare), diluted in 4% skimmed milk PBS/0.005% TWEEN® 20 brand detergent (PBS/T) pH 6.0 was added to each well and incubated for 1.5 h at room temperature followed by washing four times with PBS/T pH 6.0. One hundred µl of the substrate tetramethylbenzidine (TMB) (Calbiochem) was added to each well and incubated for 45 min before 100 µl of 0.25 M HCl was added. The absorbance was measured at 450 nm using a Sunrise TECAN spectrophotometer (TECAN, Maennedorf, Switzerland).

The same ELISA was repeated with PBS/T pH 7.4.

Surface Plasmon Resonance (SPR):

SPR experiments were carried out using a BIACORE brand 3000 instrument (GE Healthcare). Flow cells of CM5 sensor chips were coupled with shFcRn-GST (~1400-5000 RU) using amine coupling chemistry as described in the protocol provided by the manufacturer. The coupling was performed by injecting 10 µg/ml of the protein in 10 mM sodium acetate pH 5.0 (GE healthcare). Phosphate buffer (67 mM phosphate buffer, 0.15M NaCl, 0.005% TWEEN® 20 brand detergent) at pH 6.0) was used as running buffer and dilution buffer. Regeneration of the surfaces were achieved using injections of HBS-EP buffer (0.01M HEPES, 0.15M NaCl, 3 mM EDTA, 0.005% surfactant P20) at pH 7.4 (Biacore AB). For binding to immobilized shFcRn-GST, 1.0-0.5 µM of each HSA variant was injected over the The same SPR assay was repeated with HBS-EP buffer pH 7.4.

For the Purposes of this Patent Unless Otherwise Stated HSA, WT HSA, rHA Refer to Recombinant human serum albumin commercially available under the registered tradename RECOMBUMIN brand albumin (available from Novozymes Biopharma UK Ltd, Nottingham UK) was used for the examples.

Serum Albumin from Other Species

The albumins were recombinant wheres stated, produced using sequences provided from publicly available databases. Or purchased from commercial suppliers.

FcRn

Expression and purification of soluble Human (shFcRn) and Mouse (smFcRn) FcRn: Methods for the generation of shFcRn and smFcRn expression plasmids, expression and purification of each heterodimer can be found in Berntzen et al. (2005) J. Immunol. Methods 298:93-104). Alternatively shFcRn FcRn heterodimer was produced by GeneArt AG (Germany). Sequences for the two sub units of the heterodimer can be found in SEQ ID NO: 3 and SEQ ID NO: 4. The soluble receptor was expressed in HEK293 cells and purified from culture supernatant using Ni-HiTrap chromatography columns.

Example 1

Preparation of Variants

Preparation of Specific HSA Mutein Expression Plasmids

Methods for the expression of HSA mutant variants and HSA fusion variants were produced using several techniques. Standard molecular biology techniques were employed throughout such as described in Sambrook, J. and D. W. Russell, 2001. Molecular Cloning: a laboratory manual, 3rd ed. Cold Spring Harbor Laboratory Press, Cold Spring Harbor, N.Y.

Method 1. Amino Acid Substitutions in HSA Detailed in Table 1

Figure 1:
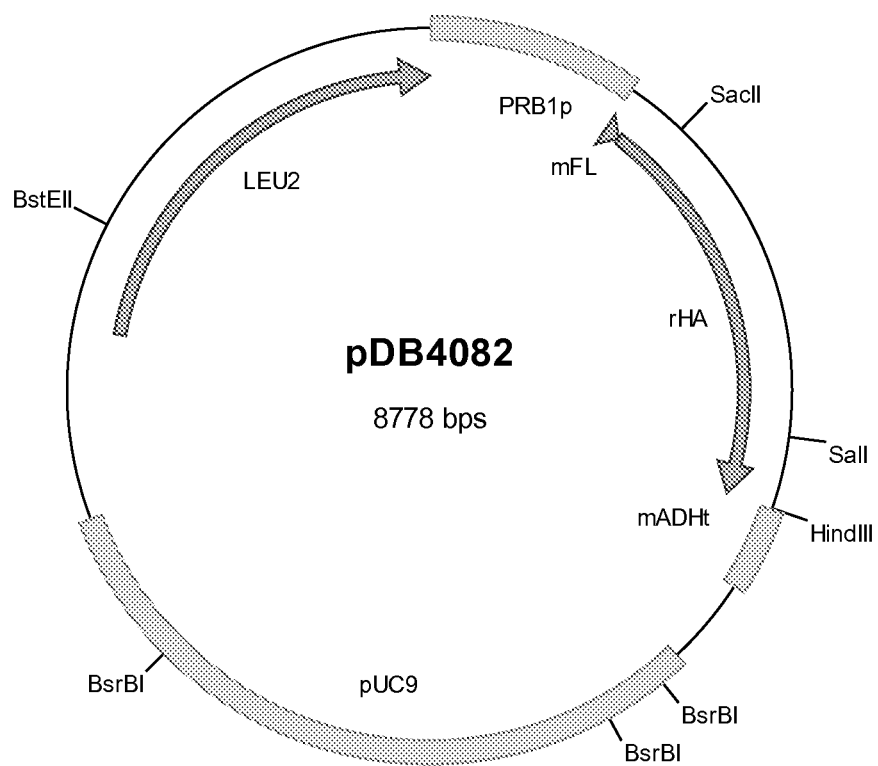
FIG. 1 shows a restriction map of the expression plasmid pDB4082.

Synthetic DNA NcoI/SacI fragments (859 bp) were generated by gene assembly (GeneArt AG, Germany) containing point mutations within the HSA-encoding gene (SEQ ID NO: 1) to introduce the desired amino acid substitution in the translated protein. Table 2 details the codons used to introduce the amino acid substitutions into the HSA-encoding gene. The nucleotide sequence of the synthetic fragment encoding unchanged amino acids (i.e. wild type) was identical to that in pDB2243 (described in WO 00/44772). The synthetic nucleotide fragments were ligated into NcoI/SacI-digested pDB2243 to produce plasmids pDB3876-pDB3886 (Table 1). For the production of expression plasmids, pDB3876-pDB3886 (see Table 1) were each digested with NotI and PvuI, the DNA fragments were separated through a 0.7% (w/v) TAE gel, and 2992 bp fragments ('NotI cassettes' including PRB1 promoter, DNA encoding the fusion leader (FL) sequence (disclosed in WO 2010/092135), nucleotide sequence encoding HSA and ADH1 terminator; see FIG. 1) were purified from the agarose gel using a Qiagen Gel Extraction Kit following the manufacturer's instructions. 'NotI cassettes' were ligated into a NotI/Shrimp Alkaline Phosphatase (Roche)-treated "disintegration" plasmid pSAC35, disclosed in EP-A-286 424 and described by Sleep, D., et al. (1991) Bio/Technology 9, 183-187. Ligation mixtures were used to transform chemically-competent E. coli DH5α. Expression plasmids pDB3887-pDB3897, pSAC35-derivatives containing the "NotI cassettes", were identified using standard techniques. Disintegration plasmids pDB3887-pDB3897 and pDB2244 (For the expression of wild type HSA, described in WO 00/44772) (Table 1) were used to transform S. cerevisiae BXP10cir⁰ (as previously described WO/2001/079480 as described below.

TABLE 1

| Plasmid, amino acid substitution introduced into HSA | |
|---|---|
| Plasmid | Construct |
| pDB2244 | HSA |
| pDB3876 | HSA D494N |

TABLE 1-continued

Plasmid, amino acid substitution introduced into HSA

| Plasmid | Construct |
|---|---|
| pDB3877 | HSA D494A |
| pDB3878 | HSA E495Q |
| pDB3879 | HSA E495A |
| pDB3880 | HSA D494Q |
| pDB3881 | HSA D494N, T496A |
| pDB3882 | HSA T496A |
| pDB3883 | HSA E492G |
| pDB3884 | HSA E492G, V493P |
| pDB3885 | HSA E492P |
| pDB3886 | HSA E492H |
| pDB3887 | HSA D494N |
| pDB3888 | HSA D494A |
| pDB3889 | HSA E495Q |
| pDB3890 | HSA E495A |
| pDB3891 | HSA D494Q |
| pDB3892 | HSA D494N, T496A |
| pDB3893 | HSA T496A |
| pDB3894 | HSA E492G |
| pDB3895 | HSA E492G, V493P |
| pDB3896 | HSA E492P |
| pDB3897 | HSA E492H | n/a = Not applicable.
pDB3876-pDB3886 are sub-cloning plasmids.

TABLE 2

Codons used to introduce amino acid substitutions into HSA

| Amino acid | Codon |
|---|---|
| Gly | GGT |
| Glu | GAA |
| Asp | GAT |
| Val | GTT |
| Ala | GCT |
| Arg | AGA |
| Lys | AAA |
| Asn | AAT |
| Met | ATG |
| Ile | ATT |
| Thr | ACT |
| Trp | TGG |
| Cys | TGT |
| Tyr | TAT |
| Leu | TTG |
| Phe | TTT |
| Ser | TCT |
| Gln | CAA |
| His | CAT |
| Pro | CCA |
| Stop | TAA |

Method 2. Production of HSA Variants D494N+E495Q+T496A and E495Q+T496A

A PCR-based method, using a QuickChange Lightening Kit (Statagene), was employed to introduce point mutations into HSA. Oligonucleotide pairs xAP094 (SEQ ID NO: 5)/xAP095 (SEQ ID NO: 6) and xAP096 (SEQ ID NO: 7)/xAP097 (SEQ ID NO: 8) were used to generate two HSA variants (D494N+E495Q+T496A and E495Q+T496A, respectively). Plasmid pDB3927 (disclosed in WO 2010/092135) was used as template DNA and the methodology recommended by the manufacturer of the kit was followed. The resulting plasmids were named pDB3995 and pDB3996 (contain HSA D494N+E495Q+T496A and E495Q+T496A expression cassettes, respectively). pDB3995 and pDB3996 were digested with BstEII/BsrBI and the linearised DNA molecules were purified using standard techniques. One hundred ng of each BstEII/BsrBI digested DNA, purified using a Qiagen PCR-Purification kit following the manufacturer's instructions, was mixed individually with 100 ng Acc65I/BamHI-digested pDB3936) (disclosed in WO 2010/092135) and used to directly transform S. cerevisiae BXP10cir⁰ using the Sigma Yeast Transformation kit described below.

Method 3. Amino Acid Substitutions in HSA Detailed in Table 3

Plasmid pDB3927 (disclosed in WO 2010/092135) (containing an identical nucleotide sequence encoding HSA as in pDB2243) was manipulated to amino acid substitutions within the mature HSA protein. Synthetic DNA fragments were generated (GeneArt AG, Germany or DNA2.0 Inc, USA) (NcoI/Bsu36I, AvrII/SphI or SacI/SphI fragments), containing point mutations within the HSA-encoding gene to introduce the desired amino acid substitution(s) into the translated protein sequence. Table 2 details the codons used to introduce the amino acid substitutions into the HSA-encoding gene. The nucleotide sequence of the synthetic fragment encoding unchanged amino acids (i.e. wild type) was identical to those in pDB3927. Synthetic DNA fragments were sub-cloned into NcoI/Bsu36I, AvrII/SphI-, SacI/Sph-digested pDB3927 (described in PCT 11527.204-WO) to generate pDB4006-pDB4010, pDB4083-pDB4101 and pDB4103-pDB4111 and pDB4194, pDB4200, pDB4202 (see Table 3).

Similarly, BamHI/SalI fragments containing point mutations in the nucleotide sequence encoding HSA were generated by gene assembly (DNA2.0 Inc, USA) and ligated into BamHI/SalI-digested pDB3964 (described in WO 2010/092135) to produce plasmids pDB3986-pDB3989 (Table 3).

The C-terminal string of amino acids from position 573-585 (KKLVAASQAALGL) (SEQ ID NO: 9) in HSA were mutated to those in macaque (PKFVAASQAALA) (SEQ ID NO: 10), mouse (PNLVTRCKDALA) (SEQ ID NO: 11), rabbit (PKLVESSKATLG) (SEQ ID NO: 12) and sheep (PKLVASTQAALA) (SEQ ID NO: 13) serum albumin. The codons used to introduce each amino acid substitution are given in Table 2. Synthetic DNA fragments (SacI/SphI) were generated (DNA2.0 Inc, USA) by gene assembly (the nucleotide sequence of the synthetic fragment encoding unchanged amino acids (i.e. wild type) was identical to that in pDB3927) and were sub-cloned into SacI/SphI-digested pDB3927 to produce plasmids pDB4114-4117 (Table 3).

Plasmids pDB3883 (Table 1), pDB4094 and pDB4095 (Table 3) were digested with NcoI/SacI and 857 bp fragments from each digest were purified before being ligated into NcoI/SacI-digested pDB4006 or pDB4110 (8.688 kb) (Table 3) to produce pDB4156-pDB4161.

Expression plasmids were generated in vivo (i.e. via homologous recombination in S. cerevisiae; a technique referred to as gap repair or in vivo cloning—see Orr-Weaver & Szostak. 1983. Proc. Natl. Acad. Sci. USA. 80:4417-4421). Modified plasmids listed in Table 3 were digested with BstEII/BsrBI and the linearised DNA molecules were purified using standard techniques. One hundred ng of each BstEII/BsrBI digested DNA, purified using a Qiagen PCR-Purification kit following the manufacturer's instructions, was mixed individually with 100 ng Acc65I/BamHI-digested pDB3936 (disclosed in WO 2010/092135) and used to directly transform S. cerevisiae BXP10cir⁰ using the Sigma Yeast Transformation kit described below.

TABLE 3

| Plasmid | Amino acid substitution in HSA |
|---|---|
| pDB3986 | HSA H440Q |
| pDB3987 | HSA H464Q |
| pDB3988 | HSA H510Q |
| pDB3989 | HSA H535Q |
| pDB4006 | HSA K573A |
| pDB4007 | HSA E492T/N503K/K541A |
| pDB4008 | HSA K541G |
| pDB4009 | HSA K541D |
| pDB4010 | HSA D550N |
| pDB4083 | HSA D494E/Q417H |
| pDB4084 | HSA Q417A |
| pDB4085 | HSA P499A |
| pDB4086 | HSA K500A |
| pDB4087 | HSA K536A |
| pDB4088 | HSA P537A |
| pDB4089 | HSA K538A |
| pDB4090 | HSA E492G/V493P/K538H/K541N/E542D |
| pDB4091 | HSA E492P/N503K/K541G/E542P |
| pDB4092 | HSA N503K |
| pDB4093 | HSA N503H |
| pDB4094 | HSA E492G/N503K |
| pDB4095 | HSA E492G/N503H |
| pDB4096 | HSA E492T |
| pDB4097 | HSA N503D |
| pDB4098 | HSA E492T/N503D |
| pDB4099 | HSA K538H |
| pDB4100 | HSA K541A |
| pDB4101 | HSA K541N |
| pDB4103 | HSA E542D |
| pDB4104 | HSA E542P |
| pDB4105 | HSA D550E |
| pDB4106 | HSA E492H/E501P/N503H/E505D/T506S/T540S/K541E |
| pDB4107 | HSA A490D/E492T/V493L/E501P/N503D/A504E/E505K/T506F/K541D |
| pDB4108 | HSA E501A |
| pDB4109 | HSA E501Q |
| pDB4110 | HSA K573P |
| pDB4111 | HSA E492G/K538H/K541N/E542D |
| pDB4114 | HSA K573P/L575F/G584A |
| pDB4115 | HSA K573P/K574N/A577T/A578R/S579C/Q580K/A581D/G584A |
| pDB4116 | HSA K573P/A577E/A578S/Q580K/A582T |
| pDB4117 | HSA K573P/A578S/S579T/G584A |
| pDB4156 | HSA E492G K573A |
| pDB4157 | HSA E492G N503K K573A |
| pDB4158 | HSA E492G N503H K573A |
| pDB4159 | HSA E492G K573P |
| pDB4160 | HSA E492G N503K K573P |
| pDB4161 | HSA E492G N503H K573P |
| pDB4194 | HSA D550E |
| pDB4200 | HSA K574N |
| pDB4202 | HSA Q580K |

TABLE 4

K500 primers and plasmids

| Original primers | | CODONS USED |
|---|---|---|
| xAP216 CTTTGGAAGTCGACGAAACTTACGTTCCA___GAATTCAACGCTG (SEQ ID NO: 14) | Gly | GGT |
| xAP217 CTTTGGAAGTCGACGAAACTTACGTTCCA___GAATTCAACGCTG (SEQ ID NO: 15) | Glu | GAA |
| xAP218 CTTTGGAAGTCGACGAAACTTACGTTCCA___GAATTCAACGCTG (SEQ ID NO: 16) | Asp | GAC |
| xAP219 CTTTGGAAGTCGACGAAACTTACGTTCCA___GAATTCAACGCTG (SEQ ID NO: 17) | Val | GTT |
| xAP220 CTTTGGAAGTCGACGAAACTTACGTTCCA___GAATTCAACGCTG (SEQ ID NO: 18) | Arg | AGA |
| xAP221 CTTTGGAAGTCGACGAAACTTACGTTCCA___GAATTCAACGCTG (SEQ ID NO: 19) | Asn | AAC |
| xAP222 CTTTGGAAGTCGACGAAACTTACGTTCCA___GAATTCAACGCTG (SEQ ID NO: 20) | Met | ATG |
| xAP223 CTTTGGAAGTCGACGAAACTTACGTTCCA___GAATTCAACGCTG (SEQ ID NO: 21) | Ile | ATT |
| xAP224 CTTTGGAAGTCGACGAAACTTACGTTCCA___GAATTCAACGCTG (SEQ ID NO: 22) | Thr | ACC |
| xAP225 CTTTGGAAGTCGACGAAACTTACGTTCCA___GAATTCAACGCTG (SEQ ID NO: 23) | Trp | TGG |
| xAP226 CTTTGGAAGTCGACGAAACTTACGTTCCA___GAATTCAACGCTG (SEQ ID NO: 24) | Cys | TGT |
| xAP227 CTTTGGAAGTCGACGAAACTTACGTTCCA___GAATTCAACGCTG (SEQ ID NO: 25) | Tyr | TAC |
| xAP228 CTTTGGAAGTCGACGAAACTTACGTTCCA___GAATTCAACGCTG (SEQ ID NO: 26) | Leu | TTG |

TABLE 4-continued

K500 primers and plasmids

| Original primers | | CODONS USED |
|---|---|---|
| xAP229 CTTTGGAAGTCGACGAAACTTACGTTCCA???GAATTCAACGCTG (SEQ ID NO: 27) | Phe | TTC |
| xAP230 CTTTGGAAGTCGACGAAACTTACGTTCCA???GAATTCAACGCTG (SEQ ID NO: 28) | Ser | TCT |
| xAP231 CTTTGGAAGTCGACGAAACTTACGTTCCA???GAATTCAACGCTG (SEQ ID NO: 29) | Gln | CAA |
| xAP232 CTTTGGAAGTCGACGAAACTTACGTTCCA???GAATTCAACGCTG (SEQ ID NO: 30) | His | CAC |
| xAP233 CTTTGGAAGTCGACGAAACTTACGTTCCA???GAATTCAACGCTG (SEQ ID NO: 31) | Pro | CCA |
| xAP234 CTTTGGAAGTCGACGAAACTTACGTTCCA???GAATTCAACGCTG (SEQ ID NO: 32) | STOP | taa |
| xAP235 GAATTAAGCTTATTACAAACCCAAAGCAGCTTGGGAAGC (SEQ ID NO: 33) | | |

TABLE 5

K573 primers and plasmids

| Original primers | | CODONS USED |
|---|---|---|
| xAP187 ATAAGCCTAAGGCAGCTTGACTTGCAGCAACAAGTTT???ACCCTCCTCG (SEQ ID NO: 34) | Gly | GGT |
| xAP188 ATAAGCCTAAGGCAGCTTGACTTGCAGCAACAAGTTT???ACCCTCCTCG (SEQ ID NO: 35) | Glu | GAA |
| xAP189 ATAAGCCTAAGGCAGCTTGACTTGCAGCAACAAGTTT???ACCCTCCTCG (SEQ ID NO: 36) | Asp | GAT |
| xAP190 ATAAGCCTAAGGCAGCTTGACTTGCAGCAACAAGTTT???ACCCTCCTCG (SEQ ID NO: 37) | Val | GTT |
| xAP191 ATAAGCCTAAGGCAGCTTGACTTGCAGCAACAAGTTT???ACCCTCCTCG (SEQ ID NO: 38) | Arg | AGA |
| xAP192 ATAAGCCTAAGGCAGCTTGACTTGCAGCAACAAGTTT???ACCCTCCTCG (SEQ ID NO: 39) | Asn | AAT |
| xAP193 ATAAGCCTAAGGCAGCTTGACTTGCAGCAACAAGTTT???ACCCTCCTCG (SEQ ID NO: 40) | Met | ATG |
| xAP194 ATAAGCCTAAGGCAGCTTGACTTGCAGCAACAAGTTT???ACCCTCCTCG (SEQ ID NO: 41) | Ile | ATT |
| xAP195 ATAAGCCTAAGGCAGCTTGACTTGCAGCAACAAGTTT???ACCCTCCTCG (SEQ ID NO: 42) | Thr | ACT |
| xAP196 ATAAGCCTAAGGCAGCTTGACTTGCAGCAACAAGTTT???ACCCTCCTCG (SEQ ID NO: 43) | Trp | TGG |
| xAP197 ATAAGCCTAAGGCAGCTTGACTTGCAGCAACAAGTTT???ACCCTCCTCG (SEQ ID NO: 44) | Cys | TGT |
| xAP198 ATAAGCCTAAGGCAGCTTGACTTGCAGCAACAAGTTT???ACCCTCCTCG (SEQ ID NO: 45) | Tyr | TAT |
| xAP199 ATAAGCCTAAGGCAGCTTGACTTGCAGCAACAAGTTT???ACCCTCCTCG (SEQ ID NO: 46) | Leu | TTG |
| xAP200 ATAAGCCTAAGGCAGCTTGACTTGCAGCAACAAGTTT???ACCCTCCTCG (SEQ ID NO: 47) | Phe | TTT |
| xAP201 ATAAGCCTAAGGCAGCTTGACTTGCAGCAACAAGTTT???ACCCTCCTCG (SEQ ID NO: 48) | Ser | TCT |

TABLE 5-continued

K573 primers and plasmids

| Original primers | | CODONS USED | |
|---|---|---|---|
| xAP202 | ATAAG<u>CCTAAGG</u>CAGCTTGACTTGCAGCAACAAGTTT░░░ACCCTCCTCG (SEQ ID NO: 49) | Gln | CAA |
| xAP203 | ATAAG<u>CCTAAGG</u>CAGCTTGACTTGCAGCAACAAGTTT░░░ACCCTCCTCG (SEQ ID NO: 50) | His | CAT |
| xAP204 | ATAAG<u>CCTAAGG</u>CAGCTTGACTTGCAGCAACAAGTTT░░░ACCCTCCTCG (SEQ ID NO: 51) | STOP | taa |
| xAP205 | AATGCTG<u>*CCATGG*</u>AGATCTGCTTGAATGTGCTGATG (SEQ ID NO: 52) | | |

Method 4. HSA K500 and K573 Permutation Library

Figure 2:
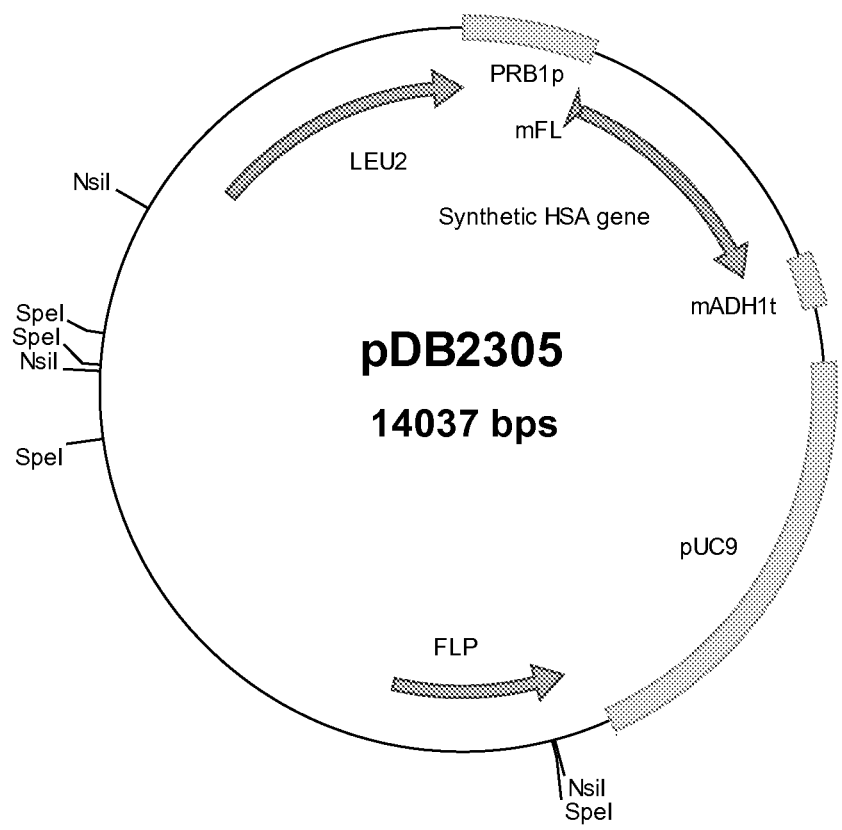
FIG. 2 shows a restriction map of the expression plasmid pDB2305
Figure 3:
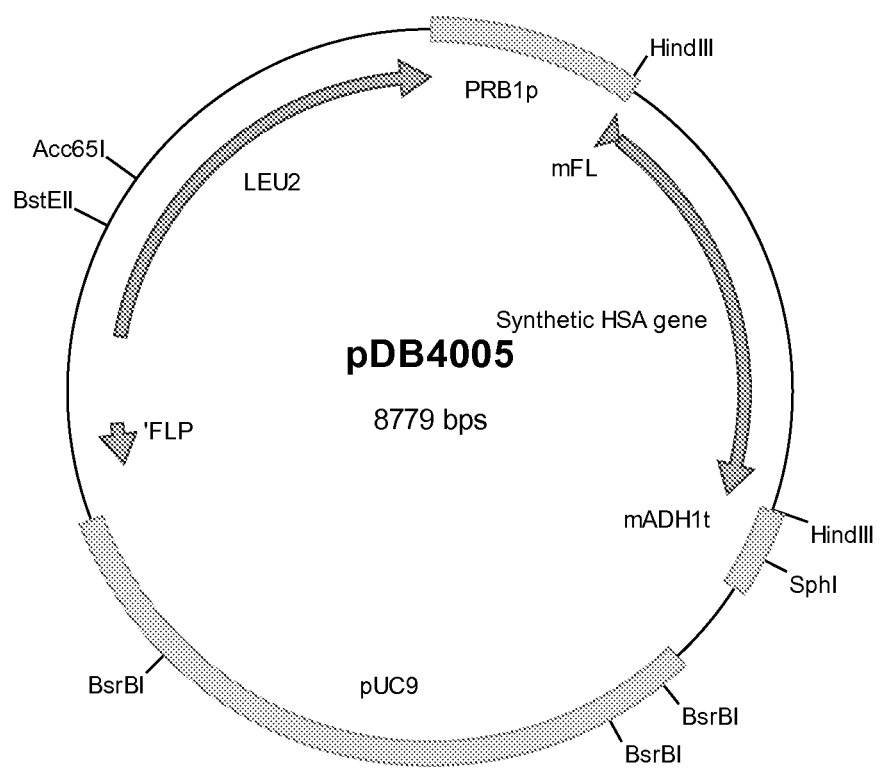
FIG. 3 shows a restriction map of the expression plasmid pDB4005

PCR was used to produce two permutation libraries in which the codons encoding amino acid 500 or 573 of mature HSA were changed (mutated) to alternative non-wild type amino acids and a termination codons (K5XXSTOP). Mutagenic oligonucleotides (Table 4 and Table 5), were designed to amplify HSA-encoding DNA and incorporate the desired changes. That is, for the changes at position 500, pDB4082 (FIG. 1) was used as a template DNA. pDB4082 is a derivative of pDB2305 (disclosed in EP1788084) and was produced as follows. pDB2305 (FIG. 2) was digested with NsiI/SpeI and the yielded 8.779 kb NsiI fragment was self-ligated to produce pDB4005 (FIG. 3). A synthetic DNA fragment (BsaI/SphI) was generated by gene assembly (DNA2.0 Inc, USA) (SEQ ID NO: 1) (containing 3' region of the PRB1 promoter, modified fusion leader sequence, nucleotide sequence encoding HSA and 5' region of the modified ADH1 terminator), and ligated into HindIII/SphI-digested pDB4005 (FIG. 3) to produce pDB4082. Note. The HindIII site in PRB1 promoter site has been removed and a SacII site within the nucleotide sequence encoding HSA has been introduced.

For the permutation library for position 500 of HSA, the nucleotide sequence encoding HSA corresponding to that between the SalI/HindIII sites (see plasmid map pDB4082, FIG. 1) was generated using the New England Biolabs Phusion kit (Table 6) and oligonucleotides listed in Table 4. Table 7 describes the PCR method employed.

The permutation library at amino acid position 573 in HSA was generated using pDB3927 as template DNA and involved amplifying the albumin-encoding DNA corresponding to that between the NcoI and Bsu36I sites using oligonucleotides detailed in Table 5.

TABLE 6

| PCR ingredients | | |
|---|---|---|
| | 500 library | 573 library |
| 20 μl Buffer HF(5×) | | |
| 2 μl dNTP mix (10 mM) | | |
| 2 μl oligonucleotide (10 μM) | xAP235 | xAP205 |
| 2 μl oligonucleotide (10 μM) | xAP216-xAP234 | xAP187-xAP204 |
| 1 μl Phusion polymerase | | |
| 1 μl Template DNA (~5 ng) | pDB4082 | pDB3927 |
| 72 μl dH$_2$O | | |

TABLE 7

| PCR conditions: | |
|---|---|
| 98° C. for 2 min | 1 cycle |
| 98° C. for 10 sec | 35 cycles |
| 57° C. for 30 sec | |
| 72° C. for 20 sec | |
| 72° C. for 5 min | 1 cycle |

For the albumin variants based at positions 500 and 573, each PCR-product was purified using a Qiagen PCR-clean up kit (according to the manufactures instructions), digested with SalI/HindIII (position 500 library) or NcoI/Bsu36I (position 573 library). The digested DNAs were then purified using a Qiagen PCR-clean up kit and ligated into SalI/HindIII- or NcoI/Bsu36I-digested pDB4082 or pDB3927, respectively, replacing the equivalent native sequence. Ligations were transformed into *E. coli* DH5α, subsequent plasmids isolated from transformants using a Qiagen miniprep kit (according to the manufacturer's instructions) and the correct constructs identified by restriction analysis. This produced a collection of plasmids, pDB4204-pDB4222 (position 500 library) pDB4173 to pDB4190 (position 573 library), containing albumin genes which differed only in their sequence corresponding to the codon for the amino acid at position 500 or 573 Table 4 and 5, respectively). The specific changes in each plasmid were confirmed by sequencing.

The resultants plasmids were used to generate expression plasmids and albumin fusion producing yeast by in vivo cloning as described above. That is, *S. cerevisiae* was transformed using the Sigma Yeast Transformation kit (described below), using a mixture of a 100 ng BstEII/BsrBI-digeste HSA variant containing plasmid and 100 ng Acc65I/BamHI digested pDB3936.

Transformation of *S. cerevisiae*

*S. cerevisiae* BXP10cir⁰ (as previously described WO/2001/079480) or Strain A cir⁰ (described in WO/2005/061718) was streaked on to YEPD plates (1% (w/v) yeast extract, 2% (w/v) Bactopeptone, 2% (w/v) glucose), 1.5% agar) and allowed to grow for 4 days at 30° C. prior to transformation. One μg of whole plasmid (i.e. circular plasmids) or, for gap repair, 100 ng BstEII/BsrBI- or NsiI/PvuI-digested HSA variant or HSA variant fusion containing plasmid and 100 ng Acc65I/BamHI digested pDB3936 were used to transform *S. cerevisiae* using a Sigma Yeast Transformation kit using a modified lithium acetate method (Sigma yeast transformation kit, YEAST-1, protocol 2; Ito et al. (1983) *J. Bacteriol.*, 153, 16; Elble, (1992) *Biotechniques*, 13, 18). The protocol was amended slightly by incubating the transformation at room temperature for 4 h prior to heat shock. Following heat shock, the cells were briefly centrifuged before being re-suspended in 200 µl 1M sorbitol then spread over BMMD agar plates, the composition of BMMD is described by Sleep et al., (2001), Yeast, 18, 403. Plates were incubated at 30° C. for 4 days before individual colonies were patched on to fresh BMMD plates. Yeast strain numbers are detailed in Table 1.

Stocks were prepared for each yeast strain as follows: BMMD broth was inoculated with a heavy loop of each yeast patch and grown for 24 h at 30° C. with orbital shaking at 200 rpm. Cells were harvested by centrifugation at 1900×g for 5 min in a Sorval RT600 centrifuge, 15 mL supernatant was removed and replaced by trehalose 40% (w/v). The cells were resuspended and transferred to cyrovials (1 mL) for storage at −80° C.

Shake Flask Growth of S. cerevisiae

BMMD (recipe 0.17% (w/v) yeast nitrogen base without amino acid and ammonium sulphate (Difco), 37.8 mM ammonium sulphate, 29 mM citric acid, 142 mM disodium hydrogen orthophosphate dehydrate pH 6.5, 2% (w/v) glucose) media (10 mL) was inoculated with each yeast strain and grown for 12 h at 30° C. with orbital shaking at 200 rpm. An aliquot of each starter culture (4 mL) was used to inoculate 2×200 mL BMMD media and grown for 36 h at 30° C. with orbital shaking at 200 rpm. Cells were harvested by filtration through 0.2 µm vacuum filter membranes (Stericup, Millipore) including a GF-D prefilter (Whatman) and the supernatant retained for purification.

Primary Concentration

Retained culture supernatant was concentrated using Tangential Flow Filtration using a Pall Filtron LV system fitted with a Omega 10 KD (0.093 sg·m2) filter (LV CENTRAMATE™ brand cassette, Pall Filtron) with a transmembrane pressure of 20 psi and a recirculation rate of 180 mL·min$^{-1}$.

Fermentation

Fed-batch fermentations were carried out in a 10 L Sartorius BIOSTAT C brand fermenter at 30° C.; pH was monitored and adjusted by the addition of ammonia or sulphuric acid as appropriate. The ammonia also provided the nitrogen source for the cultures. The level of dissolved oxygen was monitored and linked to the stirrer speed, to maintain the level at >20% of saturation. Inocula were grown in shake flasks in buffered minimal media (recipe). For the batch-phase the cultures was inoculated into fermenter media (approximately 50% of the fermenter volume) containing 2% (w/v) sucrose. The feed stage was automatically triggered by a sharp rise in the level of dissolved oxygen. Sucrose was kept at growth-limiting concentrations by controlling the rate of feed to a set nominal growth rate. The feed consisted of fermentation media containing 50% (w/v) sucrose, all essentially as described by Collins. (Collins, S. H., (1990) Production of secreted proteins in yeast, in: T. J. R. Harris (Ed.) Protein production by biotechnology, Elsevier, London, pp. 61-77).

GP-HPLC Quantitation

Purified albumin variants, fusions and conjugates were analysed by GP-HPLC and quantification as follows. Injections of 25 µL were made onto a 7.8 mm id×300 mm length TSK G3000SWXL column (Tosoh Bioscience), with a 6.0 mm id×40 mm length TSK SW guard column (Tosoh Bioscience). Samples were chromatographed in 25 mM sodium phosphate, 100 mM sodium sulphate, 0.05% (w/v) sodium azide, pH 7.0 at 1 mL/min, Samples were quantified by UV detection at 280 nm, by peak area, relative to a recombinant human albumin standard of known concentration (10 mg/mL) and corrected for their relative extinction coefficients.

Purification of Albumin Variants from Shake Flask

Albumin variants were purified from shake flask (either culture supernatant or concentrated culture supernatant) using a single chromatographic step using an albumin affinity matrix (ALBUPURE™ brand matrix—ProMetic BioSciences, Inc.). Chromatography was performed at a constant linear velocity of 240 cm/h throughout. Culture supernatant was applied to a 6 cm bed height, 2.0 mL packed bed pre-equilibrated with 50 mM sodium acetate pH 5.3. Following load the column was washed with 10 column volume (CV) of equilibration buffer, then 50 mM ammonium acetate pH 8.0 (10CV). Product was eluted with either 50 mM ammonium acetate 10 mM octanoate pH 8.0, 50 mM Ammonium Acetate 30 mM Sodium Octanoate 200 mM Sodium Chloride pH 7.0 or 200 mM Potassium thiocyanate. The column was cleaned with 0.5M NaOH (3 cv) and 20 mM NaOH (3.5 cv). Eluate fraction from each albumin variant were concentrated and diafiltered against 10 volumes of 50 mM sodium chloride (VIVASPIN®20 brand centrifugal concentrator 10,000 MWCO PES with optional diafiltration cups, Sartorius). Purified albumin variants were quantified by GP-HPLC as described above.

Purification of Albumin-Fusion Variants from Shake Flask

Albumin-fusion variants were purified from shake flask culture supernatant using a single chromatographic step using an albumin affinity matrix (ALBUPURE™ brand matrix—ProMetic BioSciences, Inc.). Chromatography was performed at a constant linear velocity of 240 cm/h throughout. Culture supernatant or concentrated culture supernatant was applied to a 6 cm bed height, 2.0 mL packed bed pre-equilibrated with 50 mM sodium acetate pH 5.3. Following load the column was washed with 10 column volume (cv) equilibration buffer then 50 mM ammonium acetate pH 8.0 (10 cv). Product was eluted with either 50 mM ammonium acetate 10 mM octanoate pH 8.0, 50 mM Ammonium Acetate 30 mM Sodium Octanoate 200 mM Sodium Chloride pH 7.0, 50 mM Ammonium Acetate 100 mM Sodium Octanoate pH 9.0 or 200 mM Potassium thiocyanate. The column was cleaned with 0.5M NaOH (3 cv) and 20 mM NaOH (3.5 cv). Eluate fraction from each albumin variant-fusion were concentrated and diafiltered against 10 volumes of 25 mM Tris, 150 mM NaCl, 2 mM KCl, pH 7.4 (VIVASPIN®20 brand centrifugal concentrator 10,000 MWCO PES with optional diafiltration cups, Sartorius). Purified albumin-fusion variants were quantified by GP-HPLC as described above.

Purification of Albumin Variants from Fermentation

Albumin variants were purified from high cell density fed batch fermentation supernatants after separation by centrifugation, using a Sorvall RC 3C centrifuge (DuPont). Culture supernatant was chromatographed through an 11 cm bed height column 8.6 mL packed bed packed with a custom synthesised albumin affinity matrix (ALBUPURE™ brand affinity matrix—ProMetic BioSciences, Inc.) as described above. Product was eluted using elution buffers describe above at a flow rate of 120 cm/h. The eluate fraction(s) was analysed by GP-HPLC (above) and reducing SDS-PAGE for purity and if required concentrated (VIVASPIN®20 brand centrifugal concentrator 10,000 MWCO PES) and applied to a 2.4×96 cm column packed with Superdex 75 run at a flow rate of 39 cm/h in 25 mM Tris, 150 mM NaCl, 2 mM KCl, pH 7.4. The peak was fractionated, assayed by GP-HPLC and pooled in order to generate the monomeric protein of interest. Pooled fractions were concentrated (VIVASPIN®20 brand centrifugal concentrator 10,000 MWCO PES, Sartorius).

All proteins to be assayed for receptor (FcRn) binding properties and or other analysis were quantified by GP-HPLC as described above corrected for their relative extinction coefficients.

Example 2

Figure 4:
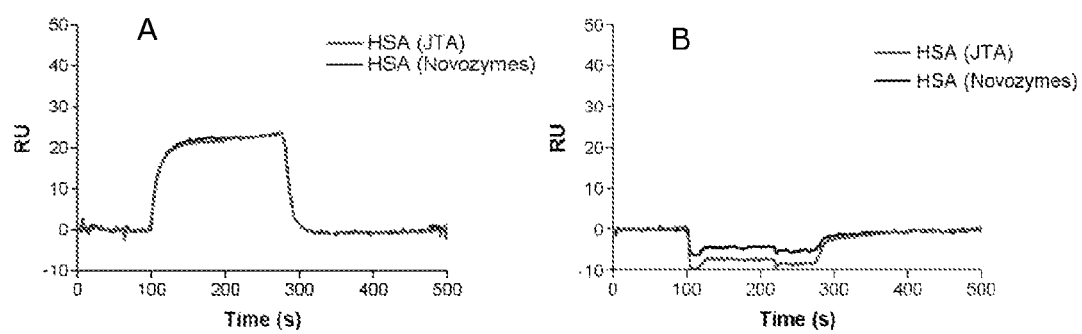
FIG. 4 shows SPR sensorgrams 10 µM albumin injected over shFcRn HSA (JTA)=fatty acid free HSA obtained from Sigma-Aldrich (A3782), HSA (Novozymes)=Commercial Recombinant human serum albumin (RECOMBUMIN brand albumin).

Determination of Receptor (shFcRn) Binding Properties of Blood Derived HSA and Recombinant Human Albumin Essentially fatty acid-free HSA (Sigma-Aldrich) was further purified by size exclusion chromatography as described in Andersen et al (2010). J. Biol. Chem. 285, (7), 4826-4836. Ten µM of monomeric HSA and rHA were analysed using SPR as described above and the data presented in FIG. 4.

Direct comparison of HSA (blood derived) with recombinant human albumin) (RECOMBUMIN brand albumin) at the same concentration (10 µM) (FIGS. 4A and 4B) shows for both samples binding to immobilized shFcRn (pH 6.0, pH 7.4 respectively) was reversible and pH dependent. In addition, comparison of HSA vs recombinant human albumin by Bosse et al (2005). J. Clin. Pharmacol. 45; 57-67, demonstrated equivalent half life in vivo human study.

Example 3

Determination of Receptor (shFcRn) Binding Properties of Albumin Variants

Two established FcRn binding assays were used, ELISA and SPR. There are major differences between the assays: In the ELISA system HSA is coated directly in wells and shFcRn-GST is added in solution whereas in the SPR assay shFcRn-GST is immobilized to a CM5 chip and HSA injected in solution. The pH can be varied in both systems.

Figure 5:
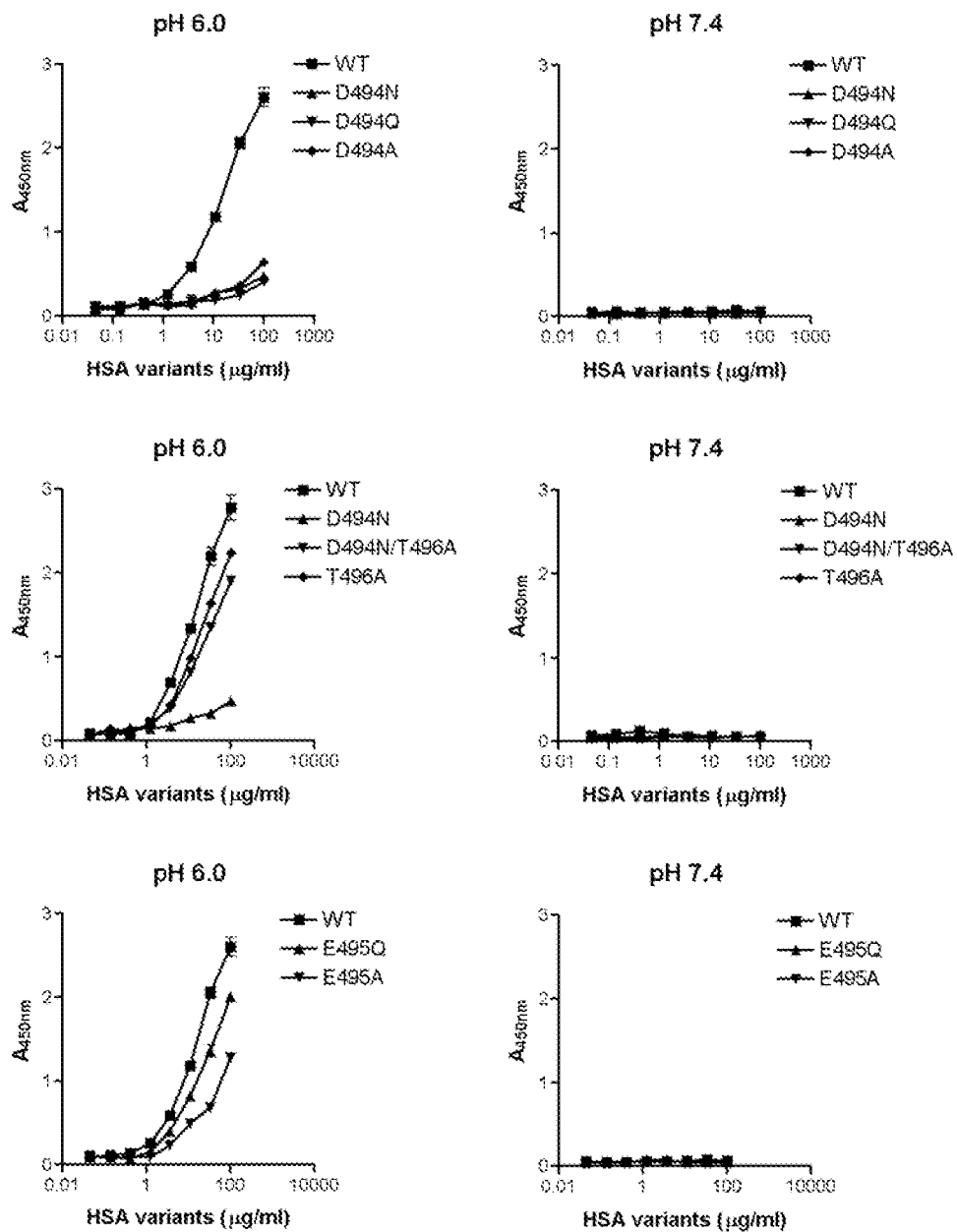
FIG. 5 shows ELISA binding of shFcRn-GST to human serum albumin (HSA) variants (100-0.045 µg/ml). Binding of WT, D494N, D494Q and D494A pH 6.0 and pH 7.4. Binding of WT, D494N, D494N/T496A and T496A at pH 6.0 and pH 7.4. Binding of WT, E495Q and E495A at pH 6.0 and pH 7.4.

The variants were analysed using ELISA at pH 6.0 and pH 7.4. Results are disclosed in FIG. 5. The ELISA values represent the mean of duplicates.

The variants were analysed using SPR analysis at pH 6.0 and pH 7.4. Results are disclosed for a representative number of variants in FIG. 6 using a concentration of the variants of 0.2 µM and in FIG. 7 using a concentration of the variants of 1 µM.

Figure 6:
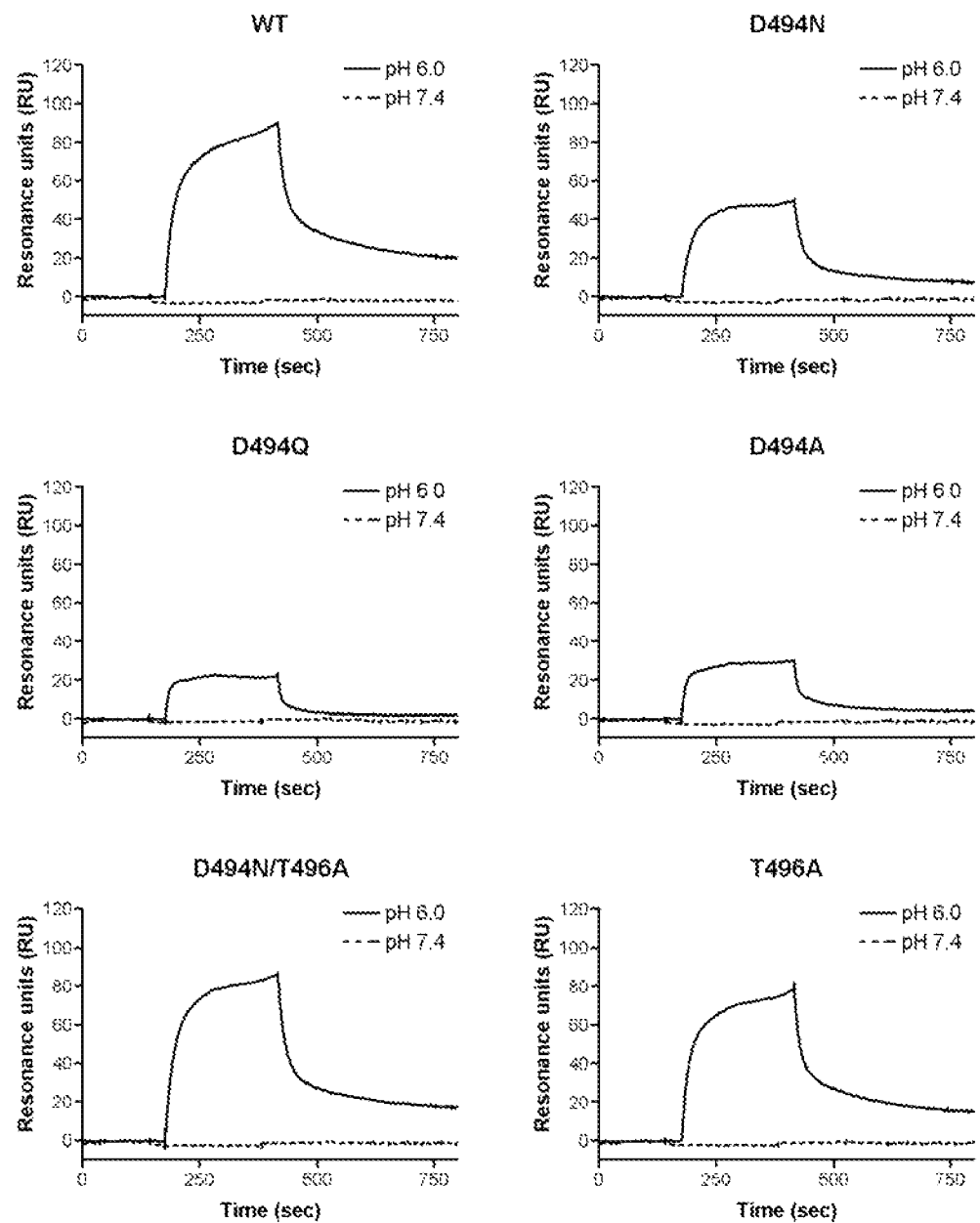
FIG. 6 shows representative sensorgrams of binding of 0.2 µM of HSA variants to immobilized shFcRn (~4600 RU). WT, D494N, D494Q, D494A, D494N/T496A and T496A.
Figure 7:
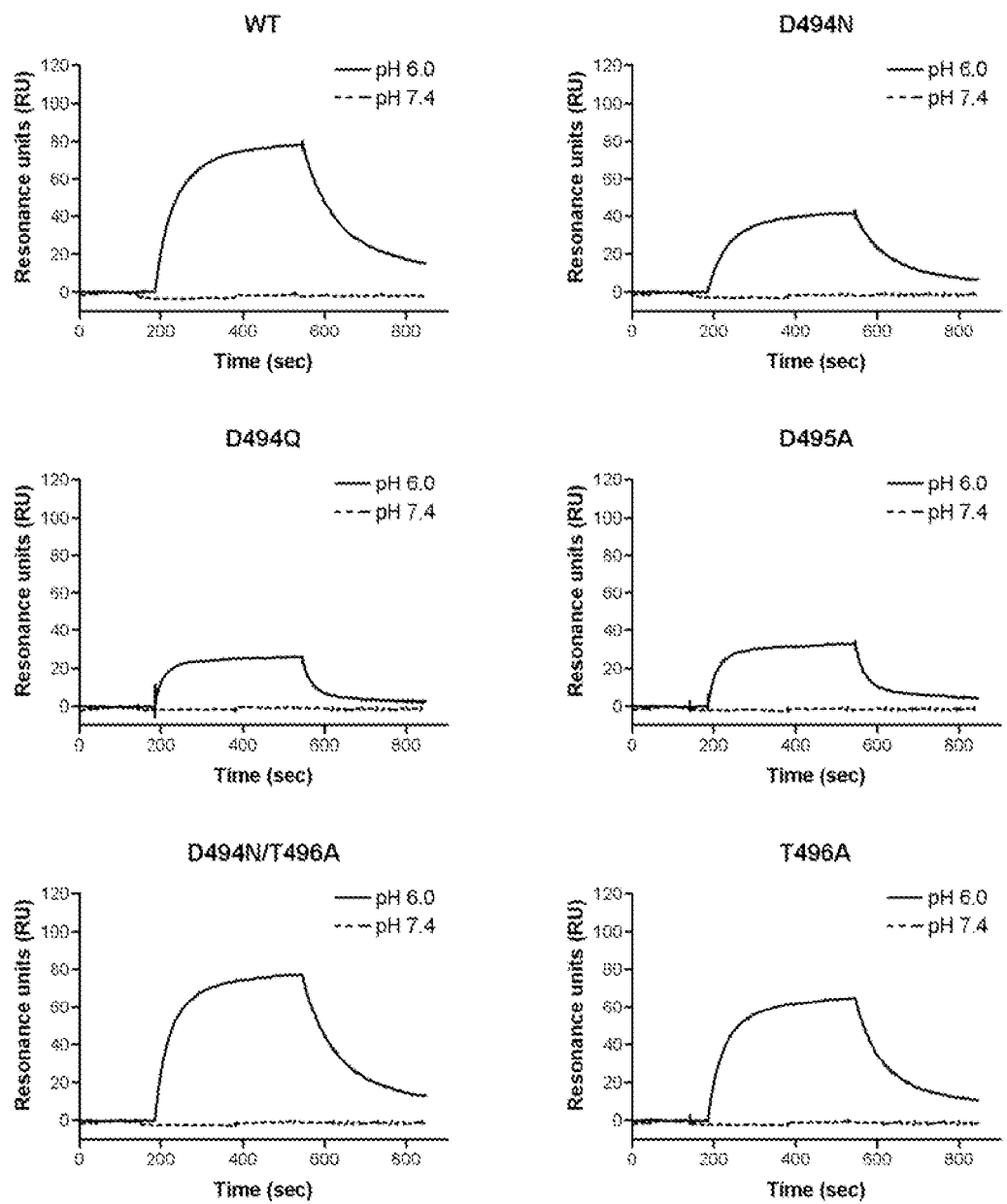
FIG. 7 shows representative sensorgrams of binding of 1 µM of HSA variants to immobilized shFcRn (~1400 RU). WT, D494N, D494Q, D494A, D494N/T496A and T496A.
Figure 8:
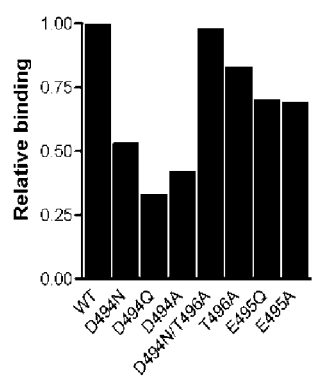
FIG. 8 shows relative binding of the HSA variants compared to WT based on two independent SPR experiments as shown (A) FIG. 6 and (B) FIG. 7.
Figure 8:
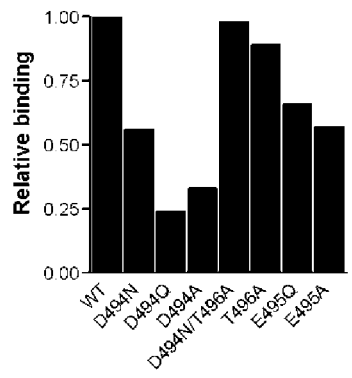

The SPR data disclosed in FIGS. 6 and 7 were normalized and the relative binding of variants at each concentration is shown in FIGS. 8 A and B respectively.

The conclusions of the analysis are that all tested variants have the characteristic binding to the receptor at pH 6.0 but no binding at pH 7.4. The variants D494N,Q,A, E495Q,A, T496A, and D494N+T496A show reduced binding to the receptor compared to HSA.

Example 4

Determination of Receptor (shFcRn/smFcRn) Binding Properties of Albumin Variants Using the SPR analysis method below the association constant Ka, the dissociation constant Kd and the binding constant KD calculated for HSA and mouse serum albumin (MSA) binding to human and mouse FcRn (Table 8).

SPR analyses—SPR analyses were performed on a BIA-CORE brand 3000 instrument (GE Healthcare) using CM5 chips and immobilization of smFcRn-GST and shFcRn-GST variants or smFcRn was performed using the amine coupling kit (GE Healthcare). Protein samples (10 µg/ml) were injected in 10 mM sodium acetate at pH 4.5 (GE Healthcare), all as described by the manufacturer. Unreacted moieties on the surface were blocked with 1M ethanolamine. For all experiments, phosphate buffer (67 mM phosphate buffer, 0.15M NaCl, 0.005% TWEEN® 20 brand detergent) at pH 6.0 or pH 7.4, or HBS-P buffer (0.01M HEPES, 0.15M NaCl, 0.005% surfactant P20) at pH 7.4 were used as running buffer or dilution buffer. Kinetic measurements were performed using a low density immobilized surface (100-200 resonance units (RU)). Serial dilutions of hIgG1 (2000.0-31.2 nM), mIgG1 (1000.0-15.6 nM), MSA (20.0-0.3 µM) and HSA (200.0-3.1 µM) were injected at pH 6.0 or pH 7.4, at a flow rate 50 µl/minute at 25° C. Additive binding was recorded by injecting HSA (10 µM), MSA (5 µM), hIgG1 (100 nM) or mIgG1 (100 nM) alone or two at a time at 25° C. at 20 µl/minute at pH 6.0 over immobilized shFcRn (~600 RU) or smFcRn (~600 RU). Competitive binding was measured by injecting shFcRn (50 nM) or smFcRn (100 nM) alone or together with different amounts of HSA or MSA (10.0-0.05 µM) over immobilized HSA (~2600 RU) or MSA (~2000 RU). In all cases, to correct for nonspecific binding and bulk buffer effects, responses obtained from the control surfaces and blank injections were subtracted from each interaction curve. Kinetic rate values were calculated using predefined models (Langmuir 1:1 ligand model, heterogeneous ligand model and steady state affinity model) provided by the BIAevaluation 4.1 software. The closeness of the fit, described by the statistical value $\chi^2$ that represents the mean square, was lower than 2.0 in all affinity estimations.

TABLE 8

Binding constants of HSA and MSA shFcRn and smFcRn.

| Albumin Species | FcRn Species | Ka ($10^3$/Ms) | Kd ($10^3$/s) | KD (µM) | KD Req. (µM) |
|---|---|---|---|---|---|
| MSA | Mouse | 4.2 ± 0.5 | 39.4 ± 3.1 | 9.3 ± 0.4 | ND[d] |
| MSA | Human | 3.8 ± 0.0 | 3.1 ± 0.1 | 0.8 ± 0.2 | ND |
| HSA | Mouse | NA | NA | NA | 86.2 ± 4.1 |
| HSA | Human | 2.7 ± 1.3 | 12.2 ± 5.9 | 4.5 ± 0.1 | 4.6 ± 0.5 |

The KD's were generated using the B|Aevaluation 4.1 software) A Langmuir 1:1 ligand model was used throughout.
The kinetic values represent the average or triplicates.
ND means: Not determined.
NA means: Not acquired

Example 5

Binding of Albumins from Other Species to Human FcRn

Figure 9:
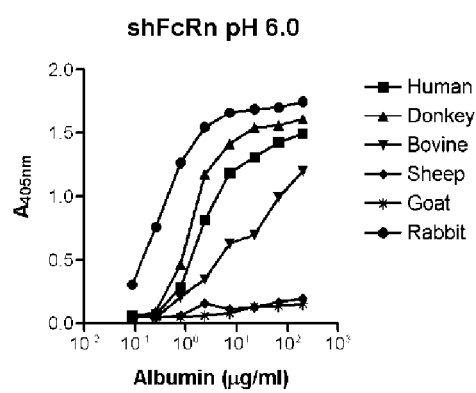
FIG. 9 shows ELISA: (A) binding of shFcRn to albumins from human, donkey, bovine, sheep, goat and rabbit at pH 6.0. (B) binding of shFcRn to albumin from guinea pig, hamster, rat and chicken at pH 6.0. (C) binding of shFcRn to albumin from human, donkey, bovine, sheep, goat and rabbit at pH 7.4. (D) binding of shFcRn to albumin from guinea pig, hamster, rat and chicken at pH 7.4. (E) relative binding of the different albumins. Relative binding of human albumin to shFcRn is defined as 1.0. The ELISA values represent the mean of duplicates.
Figure 9:
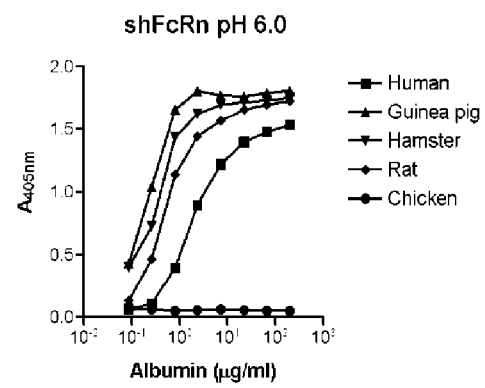
Figure 9:
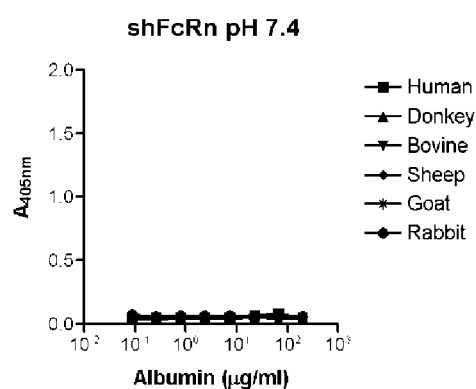
Figure 9:
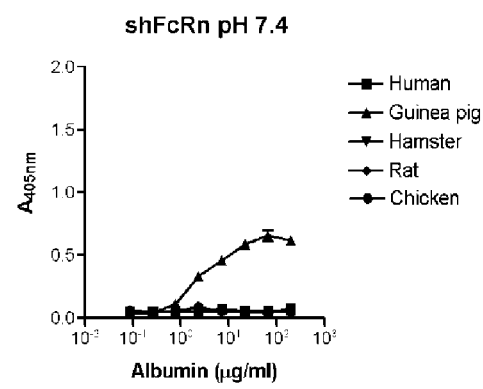
Figure 9:
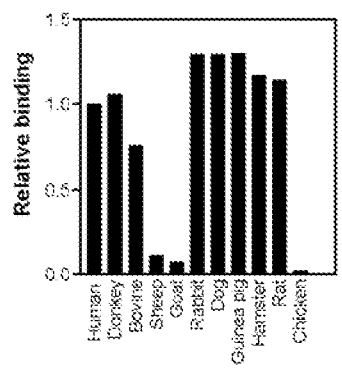

Commercially available animal albumin (either Sigma-Aldrich or Calbiochem) were further purified as described in Andersen et al (2010). J. Biol. Chem. 285, (7), 4826-4836. The binding of donkey serum albumin, bovine serum albumin, goat serum albumin, sheep serum albumin, rabbit serum albumin, dog serum albumin, hamster serum albumin, guinea pig albumin, rat serum albumin and chicken serum albumin to shFcRn was determined using the techniques described in Materials and Methods. The ELISA results are disclosed in FIG. 9 A-D and the relative bindings summarized in FIG. 9 E.

Figure 10:
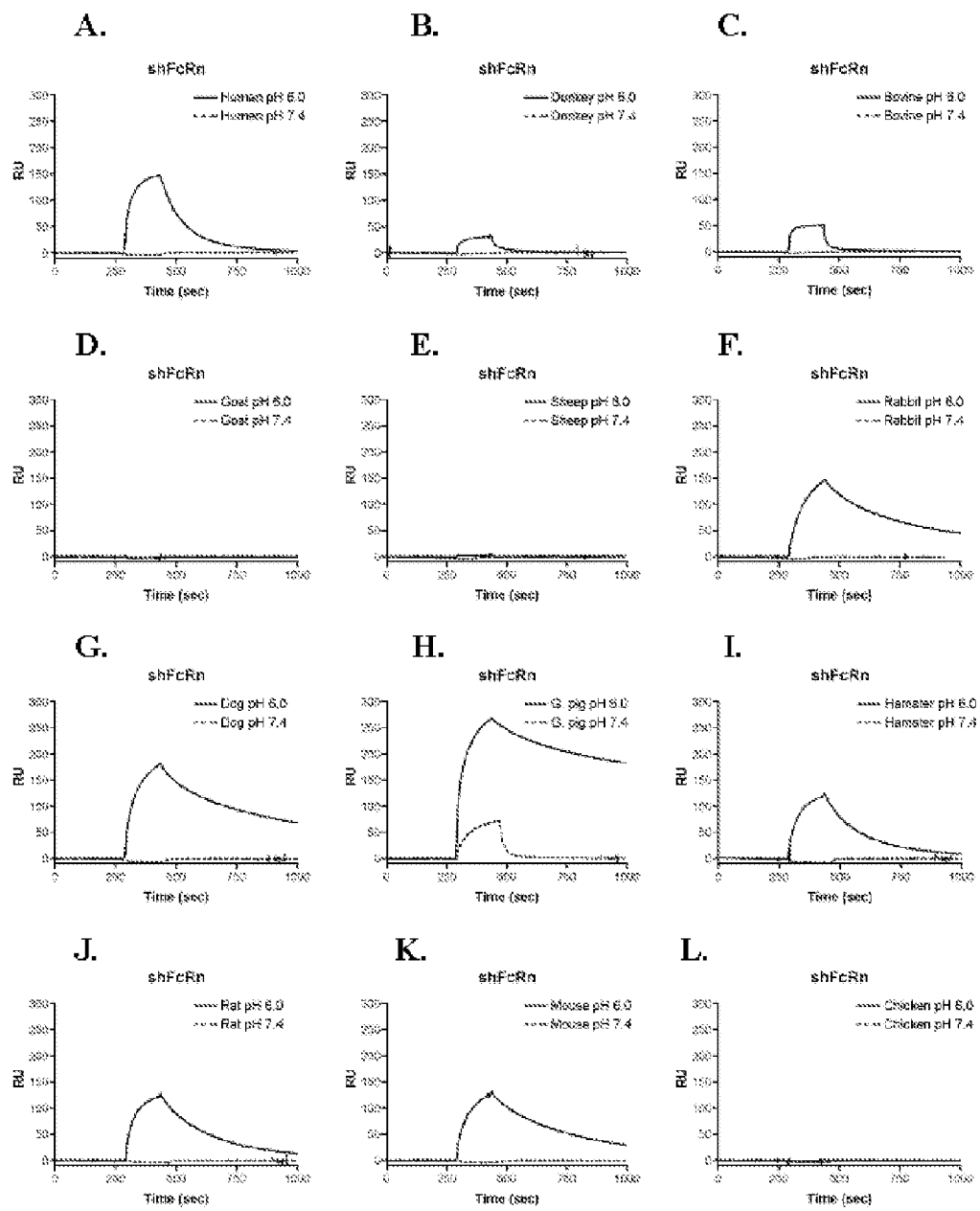
FIG. 10 shows SPR: Binding of shFcRn-GST to albumin from several species at pH 6.0 and pH 7.4. Representative sensorgrams showing binding of 5.0 µM of albumin from different species; (A) human, (B) donkey, (C) bovine, (D) goat, (E) sheep, (F) rabbit, (G) dog, (H) guinea pig, (I) hamster, (J) rat, (K) mouse and (L) chicken. The albumin variants were injected over immobilized GST-tagged shFcRn (~2100 RU). Injections were performed at 25° C. at a rate of 40 µl/min.

The SPR results are shown in FIG. 10, where the binding at pH 6.0 and pH 7.4 for each albumin species are shown. Table 10 shows an overview of the relative binding responses measured using ELISA and SPR:

TABLE 10

Cross-species albumin-FcRn binding

| Albumin | shFcRn | | | |
|---|---|---|---|---|
| | ELISA | | SPR | |
| specie | pH6.0 | pH7.4 | pH6.0 | pH7.4 |
| Human | ++(+) | – | ++(+) | – |
| Donkey | +++ | – | ++ | – |
| Cow | ++ | – | ++ | – |
| Sheep | +/– | – | – | – |
| Goat | +/– | – | – | – |
| Rabbit | ++++ | – | +++ | – |
| Dog | ND[a] | ND | +++ | – |
| G. pig | ++++ | + | ++++ | + |
| Hamster | +++ | – | +++ | – |
| Rat | +++ | – | +++ | – |
| Mouse | +++ | – | +++ | – |
| Chicken | – | – | – | – |

Relative binding responses are categorized from strongest (++++) to weakest (+) and no binding (–).
[a]Not determined (ND).

Example 6

Kinetics of the HSA Variant for shFcRn

The binding constants for variants according to the invention were determined according to the methods described in Materials and Methods.

TABLE 11

Binding constants of HSA variants for shFcRn

| Albumin Variant | Ka (10³/Ms) | kd (10⁻³/s) | KD (μM) | KD Req (μM) |
|---|---|---|---|---|
| WT | 3.2 ± 0.2 | 15.5 ± 2.5 | 4.8 | 5.4 |
| D494N | 1.7 ± 0.0 | 18.6 ± 0.0 | 10.9 | 11.8 |
| D494A | 2.3 ± 0.1 | 53.4 ± 0.3 | 23.2 | 17.0 |
| D494Q | 2.1 ± 0.0 | 58.2 ± 3.8 | 27.7 | ND |
| E495Q | 2.5 ± 0.0 | 24.1 ± 0.2 | 9.6 | 10.9 |
| E495A | 2.1 ± 0.0 | 14.0 ± 0.0 | 7.0 | 8.6 |
| D494N + T496A | 2.5 ± 0.0 | 11.0 ± 0.0 | 4.4 | 5.5 |
| T496A | 2.3 ± 0.0 | 11.7 ± 0.5 | 5.1 | 7.1 |
| E492G | 4.1 ± 0.0 | 11.0 ± 0.0 | 2.7 | ND |

The KD's were generated using the BIAevaluation 4.1 software) A Langmuir 1:1 ligand model was used throughout.
The kinetic values represent the average or triplicates.
ND means: Not determined.

The results correspond with the conclusions made in Example 3 based on SPR and ELISA data but in addition shows that E492G has increased affinity to its receptor, Example 7

Competitive Analysis of the HSA Variants

Competitive analysis of the HSA variants prepared in example 1 and WT HSA was performed using the methods described in example 4. Results are shown in FIG. 15. The results show that the variant E492G, unlike E492H E492P and E492G+V493P, has stronger binding to shFcRn than HSA.

Example 8

Analysis of Q417 Substitutions

Using the method of Example 1 variants of HSA having the substitutions Q417A and D494E+Q417H were constructed. The kinetic properties of these variants were tested using the methods in Materials and Methods and are shown in Table 12.

TABLE 12

Binding constants of HSA variants for shFcRn

| Albumin variant[a] | ka (10³/Ms) | kd (10⁻³/s) | KD[b] (μM) | KD Req[c] (μM) |
|---|---|---|---|---|
| WT | 3.2 ± 0.2 | 15.5 ± 2.5 | 4.8 | 5.4 |
| Q417A | 3.2 ± 0.1 | 26.0 ± 0.0 | 8.1 | ND |
| D494E + Q417H | 3.1 ± 0.1 | 20.5 ± 0.5 | 6.6 | ND |

[a]Dilutions of HSA variants were injected over immobilized shFcRn (~1500 RU).
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of triplicates.
[d]Not determined (ND).

The data show that variants Q417A and D494E+Q417H bind weaker to the receptor than the wild-type HSA.

Example 9

Analysis of HSA Variants in Position 499, 500, 536, 537, 538 and 573

Figure 11:
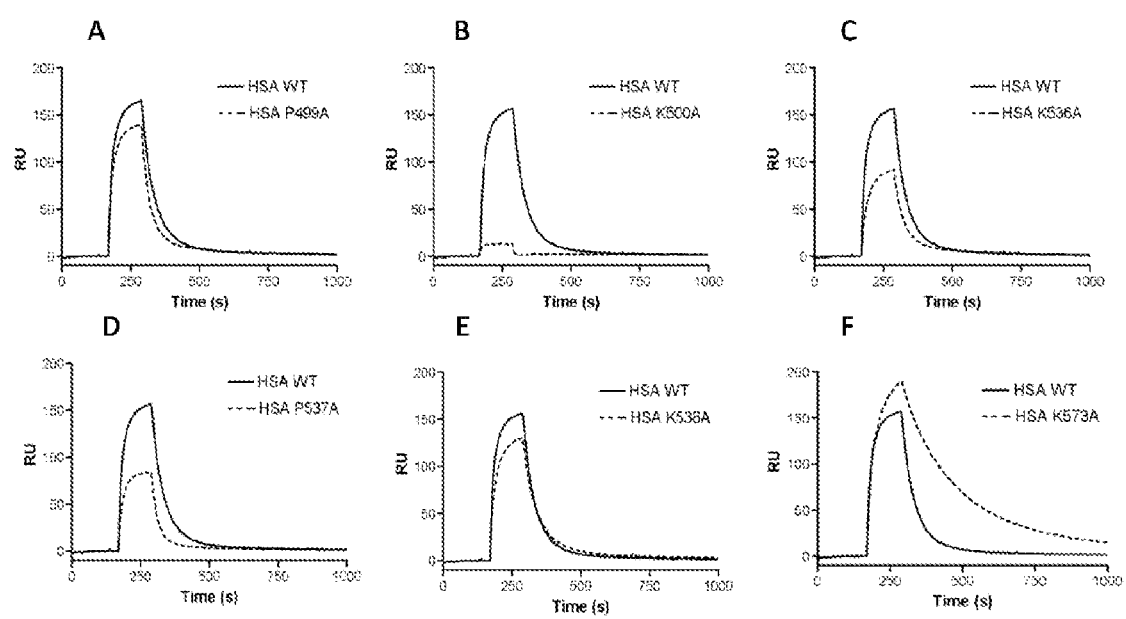
FIG. 11 shows SPR sensorgrams of selected HSA mutants compared with wild-type HSA. 20 µM of (A) WT and P499A (B) WT and K500A, (C) WT and K536A, (D) WT and P537A and (E) WT and K538A and (F) WT and K537A were injected over immobilized shFcRn at pH 6.0 (~1500 RU)

Using the method of Example 1 variants of HSA having the substitutions P499A, K500A, K536A, P537A, K538A and K573A were constructed. The receptor binding properties of these variants were tested as described in Materials and Methods. Results are shown in FIG. 11.

The data demonstrated that variants P499A, K536A, P537A and K538A had a reduced binding affinity to shFcRn relative to HSA. Variant K500A had almost completely lost its ability to bind to shFcRn and K573A had an increased binding affinity to shFcRn both relative to HSA.

Example 10

Analysis of Variants in Position 501 of HSA

Using the method of Example 1 variants of HSA having the substitutions E501A and E501Q were constructed. The kinetic properties of these variants were tested as described in Materials and Methods.

TABLE 13

Binding constants of HSA variants for shFcR

| Albumin variant[a] | ka (10³/Ms) | kd (10⁻³/s) | KD[b] (μM) | KD Req[c] (μM) |
|---|---|---|---|---|
| WT | 3.2 ± 0.2 | 15.5 ± 2.5 | 4.8 | 5.4 |
| E501A | 3.3 ± 0.0 | 26.0 ± 0.0 | 7.8 | ND |
| E501Q | 2.7 ± 0.1 | 15.5 ± 0.5 | 5.7 | ND |

[a]Dilutions of HSA variants were injected over immobilized shFcRn (~1500 RU).
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of triplicates
[d]Not determined (ND).

The data shows that variants E501A and E501Q have a slightly decreased binding affinity to shFcRn relative to HSA.

Example 11

Analysis of HSA Variants in Position 573

Figure 12:
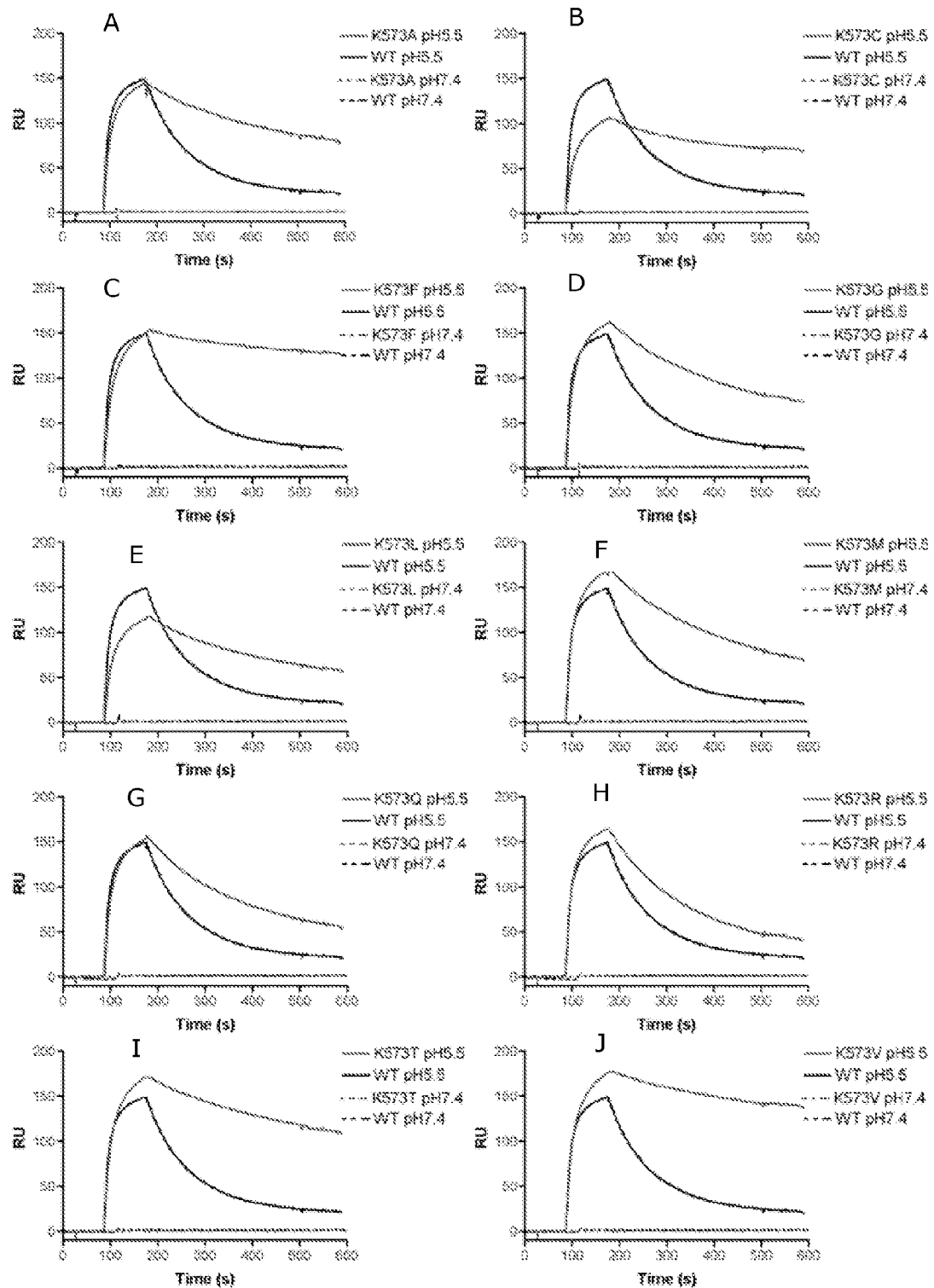
FIG. 12 shows SPR sensorgrams of HSA mutants compared with WT HSA. 10 µM of (A) WT and K573A (B) WT and K573C, (C) WT and K573F, (D) WT and K573G and (E) WT and K573L and (F) WT and K573M, (G) WT and K573Q, (H) WT and K573R and (I) WT and K573T and (J) WT and K573V injected over immobilized shFcRn at pH 5.5 and pH7.4. Injections were performed at 25° C. at a flow rate of 80 µl/min.
Figure 13:
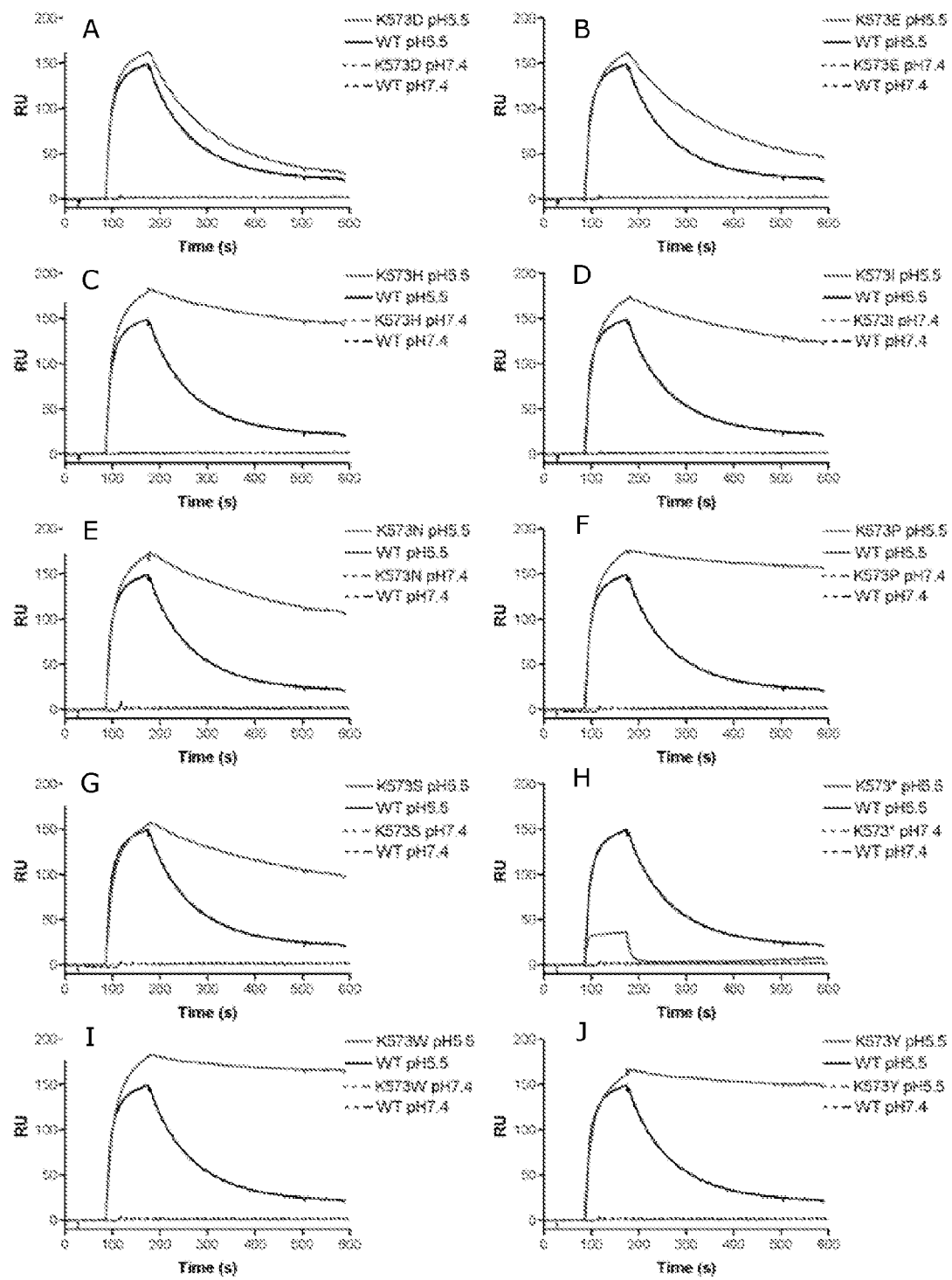
FIG. 13 shows SPR sensorgrams of HSA mutants compared with wild-type HSA. 10 µM of (A) WT and K573D (B)

Using the method of Example 1 variants of HSA having a substitution at position 573 were constructed. All variants at position 573 were generated and the receptor binding properties of these variants were tested as described in Materials and Methods but with SPR analysis performed at pH 5.5. Results are shown in the table 14 below and FIGS. 12 and 13.

TABLE 14

Kinetics of HSA K573 single point mutants.

| Albumin variant[a] | ka (10³/Ms) | kd (10⁻³/s) | KD[b] (nM) |
|---|---|---|---|
| WT | 9.0 ± 0.0 | 6.9 ± 0.1 | 766 |
| K573A | 7.4 ± 0.0 | 2.2 ± 0.0 | 297 |
| K573C | 4.2 ± 0.0 | 1.1 ± 0.2 | 262 |
| K573D | 7.9 ± 0.2 | 4.1 ± 0.3 | 518 |
| K573E | 9.0 ± 0.0 | 2.9 ± 0.0 | 322 |
| K573F | 7.8 ± 0.1 | 0.5 ± 0.1 | 74 |
| K573G | 8.5 ± 0.0 | 1.8 ± 0.1 | 212 |
| K573H | 12.0 ± 0.2 | 0.8 ± 0.0 | 68 |
| K573I | 8.6 ± 0.0 | 0.8 ± 0.2 | 99 |
| K573L | 5.1 ± 0.2 | 2.3 ± 0.1 | 451 |
| K573M | 8.6 ± 0.0 | 1.9 ± 0.0 | 221 |
| K573N | 7.3 ± 0.2 | 1.1 ± 0.3 | 151 |
| K573P | 9.8 ± 0.0 | 0.6 ± 0.1 | 61 |
| K573Q | 7.7 ± 0.2 | 2.6 ± 0.0 | 338 |
| K573R | 8.5 ± 0.0 | 3.0 ± 0.2 | 353 |
| K573S | 7.9 ± 0.2 | 1.2 ± 0.2 | 152 |
| K573T | 8.7 ± 0.2 | 1.1 ± 0.1 | 126 |
| K573V | 8.1 ± 0.0 | 0.6 ± 0.2 | 80 |
| K573W | 15.0 ± 0.2 | 0.4 ± 0.3 | 29 |
| K573Y | 22.0 ± 0.1 | 0.5 ± 0.1 | 23 |
| K573STOP | ND | ND | 141000 |

[a]Dilutions of HSA variants were injected over immobilized shFcRn (~1500 RU).
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of duplicates.
[d]Not determined (ND).

The results show that all variants having substitution in position 573 have improved binding to shFcRn compared with WT HSA. In particular the variants K573F, K573H, K573P, K573W and K573Y have more than 10 fold lower KD to shFcRn than the parent HSA. The variant K573STOP is a truncated albumin having a stop codon in position 573. The sensorgram for the K573STOP variant show significantly reduced binding compare to the WT HSA and generated a high KD. The increased affinity that we have shown for the variant K573E, a natural variant characterized by Otagiri (2009). Biol. Pharm. Bull. 32(4) 527-534, is predicted to have increased half-life in vivo.

Example 12

Analysis of Further HSA Variants

Using the method of Example 1 variants of HSA having the substitutions E492G, E492G+N503H, N503H, D550E, E492G+N503K, E542P, H440Q, K541G, K541D, D550N E492G+K538H+K541N+E542D, E492T+N503K+K541A, E492P+N503K+K541G+E542P, E492H+E501P+N503H+E505D+T506S+T540S+K541E, A490D+E492T+V493L+E501P+N503D+A504E+E505K+T506F+K541D, E492G+V493P+K538H+K541N+E542D were constructed. The receptor binding properties of these variants were tested as described in Materials and Methods, and the results are shown in Table 15 and FIG. 14.

TABLE 15

Binding constants of HSA variants for shFcR

| Albumin variant[a] | Ka (10³/Ms) | kd (10⁻³/s) | KD[b] (μM) | KD Req[c] (μM) |
|---|---|---|---|---|
| WT | 3.2 ± 0.2 | 15.5 ± 2.5 | 4.8 | 5.4 |
| E492G | 4.1 ± 0.0 | 11.0 ± 0.0 | 2.7 | ND |
| E492G/N503H | 6.9 ± 0.1 | 14.5 ± 0.5 | 2.1 | ND |
| N503H | 5.4 ± 0.0 | 24.0 ± 0.1 | 4.4 | ND |
| D550E | 3.2 ± 0.4 | 11.8 ± 0.0 | 3.6 | ND |
| E492G/N503K | 5.9 ± 0.1 | 16.0 ± 0.0 | 2.7 | ND |
| E542P | 3.4 ± 0.0 | 15.7 ± 0.2 | 4.7 | ND |
| H440Q | 3.2 ± 0.1 | 20.8 ± 0.0 | 6.5 | ND |
| K541G | 3.2 ± 0.0 | 23.0 ± 0.0 | 7.1 | ND |
| K541D | 2.6 ± 0.0 | 24.0 ± 0.0 | 9.2 | ND |
| D550N | 2.5 ± 0.0 | 30.0 ± 0.0 | 12.0 | ND |

[a]Dilutions of HSA variants were injected over immobilized shFcRn (~1500 RU).
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of triplicates.
[d]Not determined (ND).

The results show that for position 550, a substitution to E results in an increased affinity whilst a substitution to N resulted in reduced affinity for shFcRn at pH6.0. When this analysis was repeated for the D550E substitution at pH5.5 however no observable increase in affinity was seen. The substituted for an acid amino acid (E) maintains and improves the binding. However the substitution for an uncharged amide amino acid reduces binding at pH6.0. Based on this observation, we would predict for this position that substitutions to basic amino acids (H, K and R) would result in further reductions in binding.

Example 13

Mutations in His Residues

The following variants were generated using the methods described in Example 1: H440Q, H464Q, H510Q and H535Q. FIG. 15 shows SPR sensorgrams of these variants interacting with shFcRn as described in Materials and Methods.

It was found that the variant H440Q bound with comparable affinity as HSA. In contrast H464Q, H510Q and H535Q had significantly reduced affinity to shFcRn. This supports the previously published observations that mutagenesis of these Histidine residues significantly reduced HSA binding to shFcRn (Wu et al (2010). PEDS, 23(10)789-798). Wu et al show a reduced half-life for a diabody fusion proteins (scFv-DIII)2 in mice with an order of removal from slowest to fastest: Db-DIII WT>H535A>H510A>H464A>Db. Based on affinity to shFcRn and when compared to smFcRn (example 5) we would predict the clearance order in humans to be (for glutamine (Q) substitutions) WT>H440Q>H510Q>H464Q>H535Q.

Example 14

Further Variants

The following variants were generated using the methods described in Example 1: K574N and Q580K in HSA. Binding of the variants to FcRn was tested using the SPR assay as described in Materials and Methods and the results are shown in Table 16.

The results show that variants K574N and Q580K bound stronger to shFcRn.

TABLE 16

Following kinetic data was found for these variants:

| Albumin variant | ka ($10^3$/Ms) | kd ($10^{-3}$/s) | KD (μM) |
|---|---|---|---|
| WT | 9.7 ± 0.0 | 30.0 ± 0.1 | 3.1 |
| K574N | 4.9 ± 01 | 8.4 ± 0.1 | 1.7 |
| Q580K | 6.0 ± 0.0 | 9.3 ± 0.0 | 1.5 |

Example 15

Analysis of HSA Variants in Position 500

Using the method of Example 1 variants of HSA having a substitution at position 500 were constructed. All variants at position 500 were generated and the receptor binding properties of these variants were tested. BIACORE X, BIACORE X100 and Sensor Chip CM5 were used for all analyses, both supplied by G E Healthcare. shFcRn produced by GeneArt AG (Germany) (diluted to 10 μg/mL in 10 mM sodium acetate pH 5.0 (G E Healthcare)) was immobilised on flow cell 2 (FC2) to levels between 1600-2200 response units (RU) via standard amine coupling as per manufacturers instructions (G E Healthcare). A blank immobilisation was performed on flow cell 1 (FC1) for it to serve as a reference cell. To stabilise the assay, 3-5 start up cycles were run first, with running buffer (67 mM phosphate buffer, 0.15M NaCl, 0.005% TWEEN 20 brand detergent at pH 5.75±0.25) only, followed by regeneration. WT rHA and K500 library variants were injected at various concentrations (1 μM-150 μM) for 90 s at a constant flow rate of (30 μl/min) at 25° C. followed by regeneration of the surface using HBS-EP buffer pH 7.4 (G E Healthcare) until approximate initial baseline RU was restored (usually 12 s pulse would suffice).

Results are shown in the Table 17 and FIG. 16

TABLE 17

Kinetics of HSA K500 single point mutants.

| Albumin variant | ka ($10^3$/Ms) | kd ($10^{-3}$/s) | KD[b] (μM) | KD Req[c] (μM) |
|---|---|---|---|---|
| K500R | 4.42 | 7.21 | 1.63 | |
| K500I | 5.18 | 10.9 | 2.1 | |
| WT | 4.24 | 9.2 | 2.2[a] | |
| K500L | 3.73 | 11.9 | 3.2 | |
| K500Q | 1.07 | 3.4 | 3.2 | |
| K500V | 3.29 | 11.0 | 3.3 | |
| K500Y | 3.97 | 14.6 | 3.7 | |
| K500M | 2.48 | 21.5 | 8.7 | |
| K500T | 1.2 | 13.4 | 11.2 | |
| K500W | 0.5 | 5.4 | 11.7 | |
| K500N | 1.3 | 18.2 | 14 | |
| K500F | 5.17 | 73.7 | 14.3 | |
| K500H | 4 | 63.8 | 16 | |
| K500P | ND | ND | ND | 51* |
| K500C | 2.38 | 124 | 52 | |

TABLE 17-continued

Kinetics of HSA K500 single point mutants.

| Albumin variant | ka ($10^3$/Ms) | kd ($10^{-3}$/s) | KD[b] (μM) | KD Req[c] (μM) |
|---|---|---|---|---|
| K500S | ND | ND- | ND | 70.2* |
| K500A | 2.61 | 208 | 79.9 | |
| K500D | ND | ND | ND | 83.3* |
| K500G | ND | ND | ND | 95.4* |
| K500E | KD not calculable see FIG. 16 | | | |
| K500 STOP | Null binder | | | |

[a]Mean of 4 values.
[b]The kinetic rate constants were obtained using a simple first-order (1:1) bimolecular interaction model.
[c]The steady state affinity constant was obtained using an equilibrium (Req) binding model supplied by the BIAevaluation 4.1 software.

The results show for variants K500R and K500I have increased and comparable affinity for shFcRn compared to WT HSA respectively. Variant K500E bound tightly to immobilised shFcRn but still demonstrated the characteristic pH-dependency of the FcRn interaction. This complex was very stable, such that kinetic analysis was not possible (FIG. 16). All other variants have reduced binding to shFcRn than wt rHA.

All variants bound to shFcRn (to some extent) at pH 5.5. No binding of K500 library variants to shFcRn was detectable at pH 7.4.

Example 16

Fusion Polypeptides

The generation of albumin fusions containing albumin muteins

Plasmids containing expression cassettes for the production of scFv (vHvL) genetically-fused to HSA, at either the N- or C-terminus or both, (described in, Evans et al., 2010. Protein Expression and Purification. 73, 113-124) were modified to allow the production of albumin fusions using in vivo cloning (describe above). That is, pDB3017 (FIG. 17), pDB3021 (FIG. 18), pDB3056 (FIG. 19) were digested with NsiI/SpeI and NsiI fragments corresponding 9.511 kb, 9.569 kb and 8.795 kb, respectively, were purified using standard techniques. Purified NsiI fragments were self-ligated and used to transform chemically competent E. coli DH5α to produce pDB4168, pDB4169 and pDB4170, respectively (Table 18).

Similarly, pDB3165 (containing the bivalent fusion) (FIG. 20) was digested with NotI and the expression cassette (4.506 kb fragment) was purified before being ligated into NotI-digested pDB3927 to produce pDB4172 (FIG. 21, Table 18).

Synthetic SalI/Bsu36I DNA fragments (269 bp), which contain point mutations within the albumin encoding nucleotide sequence to introduce amino acid substitutions corresponding to K500A, or D550N or K573P into the translated albumin protein sequence, were generated by gene assembly (GeneArt AG, Germany). The SalI/Bsu36I fragments were individually ligated into SalI/Bsu36I-digested pDB4168-pDB4170 and pDB4172 and used to transform chemically competent E. coli DH5α using standard techniques to generate plasmids pDB4265-pDB4276 (Table 18).

TABLE 18

Albumin variant fusions

| Plasmid | Construct |
| --- | --- |
| pDB3017 | scFv (anti-FITC) - HSA - FLAG |
| pDB3021 | HSA - GS linker - scFv (anti-FITC) - FLAG |
| pDB3056 | HSA - FLAG |
| pDB3165 | scFv (anti-FITC) - HSA - GS linker - scFv (anti-FITC) - FLAG |
| pDB4168 | scFv (anti-FITC) - HSA - FLAG |
| pDB4169 | HSA - GS linker - scFv (anti-FITC) - FLAG |
| pDB4170 | HSA - FLAG |
| pDB4172 | scFv (anti-FITC) - HSA - GS linker - scFv (anti-FITC) - FLAG |
| pDB4265 | scFv (anti-FITC) - HSA K500A - FLAG |
| pDB4266 | scFv (anti-FITC) - HSA D550N - FLAG |
| pDB4267 | scFv (anti-FITC) - HSA K573P - FLAG |
| pDB4268 | HSA K500A - GS linker - scFv (anti-FITC) - FLAG |
| pDB4269 | HSA D550N - GS linker - scFv (anti-FITC) - FLAG |
| pDB4270 | HSA K573P - GS linker - scFv (anti-FITC) - FLAG |
| pDB4271 | HSA K500A - FLAG |
| pDB4272 | HSA D550N - FLAG |
| pDB4273 | HSA K573P - FLAG |
| pDB4274 | scFv (anti-FITC) - HSA K500A - GS linker - scFv (anti-FITC) - FLAG |
| pDB4275 | scFv (anti-FITC) - HSA D550N - GS linker - scFv (anti-FITC) - FLAG |
| pDB4276 | scFv (anti-FITC)-HSA K573P-GS linker-scFv (anti-FITC) - FLAG |
| pDB4277 | scFv (anti-FITC) - HSA K573A - FLAG |
| pDB4278 | HSA K573A - GS linker - scFv (anti-FITC) - FLAG |
| pDB4279 | HSA K573A-FLAG |
| pDB4280 | scFv (anti-FITC) - HSA K573A - GS linker - scFv (anti-FITC) - FLAG |
| pDB4281 | HSA K500A - GS linker - scFv (anti-FITC) |
| pDB4282 | HSA D550N-GS linker-scFv (anti-FITC) |
| pDB4283 | HSA K573P-GS linker-scFv (anti-FITC) |
| pDB4284 | HSA - GS linker - scFv (anti-FITC) |
| pDB2613 | HSA- GS linker-IL1RA (N84Q) |
| pDB4285 | HSA K573A- GS linker -IL1RA (N84Q) |
| pDB4286 | HSA D550N- GS linker -IL1RA (N84Q) |
| pDB4287 | HSA K500A- GS linker -IL1RA (N84Q) |
| pDB4288 | HSA K573P- GS linker -IL1RA (N84Q) |

Similarly, a DNA fragment was generated by PCR (using standard techniques), to introduce a K573A substitution in the translated albumin protein sequence. PCR was performed using the New England Biolabs Phusion kit using pDB4267 (FIG. 22) as template DNA and oligonucleotides xAP238 (SEQ ID NO: 53) and xAP239 (SEQ ID NO: 54):

Table 19 describes PCR cycling.

TABLE 19

| PCR cycling | |
| --- | --- |
| 98° C. for 2 min | 1 cycle |
| 98° C. for 10 sec | 35 cycles |
| 57° C. for 30 sec | |
| 72° C. for 10 sec | |
| 72° C. for 5 min | 1 cycle |

The PCR-product was purified, digested with SalI/Bsu36I, and the fragment (269 bp) isolated was ligated into SalI/Bsu36I-digested pDB4168-pDB4170 and pDB4172 and used to transform chemically competent *E. coli* DH5α. Resulting plasmids (pDB4277-pDB4280) are listed in Table 18.

The nucleotide sequence encoding the FLAG tag was removed from plasmids pDB4168 and pDB4268-4270 (plasmids for the expression of scFv N-terminally fused to HSA and HSA muteins K500A, D550N and K573P, respectively. pDB4168 and pDB4268-4270 (Table 18) were digested with Bsu36I/SphI to remove a 231 bp product comprising 3' region of HSA-encoding gene, nucleotide sequence encoding FLAG tag and 5' region of ADH1 terminator. A Bsu36I/SphI fragment (207 bp), comprising 3' region of HSA-encoding gene and 5' region of mADH1 terminator (SEQ ID1) from pDB4181 was ligated into Bsu36I/SphI-digested pDB4168 and pDB4268-pDB4270 using standard techniques. Ligation mixtures were used to transform chemically competent *E. coli* DH5α using standard techniques to generate plasmids pDB4281-pDB4284 (Table 18)

pDB4265-pDB4284 were digested with BstEII/BsrBI and the linearised DNA molecules were purified using standard techniques. One hundred ng BstEII/BsrBI DNA samples were mixed with 100 ng Acc65I/BamHI-digested pDB3936 and used to transform *S. cerevisiae* BXP10cir⁰ using the Sigma Yeast Transformation kit described below. In each case the expression plasmid was generated in the yeast by homologous recombination (in vivo cloning) between the albumin-fusion containing plasmid (pDB4265-pDB4280) (Table 18) and pDB3936.

Plasmids pDB3017, pDB3021, pDB3056 and pDB3165 (wild type HSA fusions, described by Evans et al., 2010. Protein Expression and Purification. 73, 113-124) were used to transform *S. cerevisiae* Strain Acir⁰ (described in WO/2005/061718) using the Sigma Yeast Transformation kit described below.

The nucleotide sequence encoding human IL-1RA (interleukin-1 receptor antagonist) (accession number: CAA59087) could be synthetically generated by gene assembly. The nucleotide sequence of the 708 bp synthetic fragment (Bsu36I/SphI fragment) is given in SEQ ID NO: 55 and includes the 3' region of the gene encoding HSA, the nucleotide sequence encoding a GS linker, the nucleotide sequence encoding human IL-1RA (N84Q to abolish the N-linked glycosylation motif) and the 5' region of the ADH1 terminator. The synthetic DNA fragment could be ligated into Bsu36I/SphI-digested pDB3927 to produce pDB2588.

Plasmids containing the expression cassettes for the production of IL-1RA genetically fused to the C-terminus of HSA and the HSA variants K500A, D550N, K573A and K573P were prepared as follows. pDB2588 was digested with Bsu36I/SphI and a 705 bp fragment containing the '3 region of the HSA encoding gene, nucleotide sequence encoding a GS linker, nucleotide sequence encoding human IL1-RA (N84Q) and the 5' region of a modified *S. cerevisiae* ADH1 terminator (SEQ ID3) was purified using standard techniques then ligated into Bsu36I/SphI-digested pDB4006 (containing HSA K573A expression cassette), pDB4010 (containing HSA D550N expression cassette), pDB4086 (containing HSA K500A expression cassette), pDB4110 (containing HSA K573P expression cassette) to generate pDB4287, pDB4286, pDB4285 and pDB4288, respectively (for an example, see FIG. 23). pDB4285-pDB4288 were digested with NsiI/PvuI and the linearised DNA molecules were purified using standard techniques. One hundred ng NsiI/PvuI-digested DNA samples were mixed with 100 ng Acc65I/BamHI-digested pDB3936 (9721 bp) (i.e. in vivo cloning) and used to transform *S. cerevisiae* (i.e. by in vivo cloning) using the Sigma Yeast Transformation kit described below.

Preparation of an *S. cerevisiae* strain expressing wild type HSA genetically fused to a GS linker and IL1-RA (N84Q) (see Table 18) could also be generated following the methods described above.

The fusion polypeptides were analysed for their binding to FcRn using the SPR method described above and following results were obtained:

TABLE 20

Kinetics of HSA fusion variants.

| Albumin variant[a] | ka (10³/Ms) | kd (10⁻³/s) | KD[b] (μM) |
|---|---|---|---|
| HSAWT | 9.7 ± 0.0 | 30.0 ± 0.1 | 3.1 |
| K574N | 4.9 ± 01 | 8.4 ± 0.1 | 1.7 |
| Q580K | 6.0 ± 0.0 | 9.3 ± 0.0 | 1.5 |
| K573P | 2.8 ± 0.0 | 0.4 ± 0.0 | 0.1 |
| HSA-WT-FLAG | 8.2 ± 0.2 | 24.0 ± 0.2 | 2.9 |
| HSA-D550N-FLAG | 5.9 ± 0.0 | 49.0 ± 0.1 | 8.3 |
| HSA-K500A-FLAG | ND[c] | ND | ND |
| HSA-K573A-FLAG | 6.1 ± 0.1 | 7.1 ± 0.1 | 1.1 |
| HSA-K573P-FLAG | 6.2 ± 0.1 | 1.2 ± 0.1 | 0.2 |
| HSA-WT-IL1RA | 6.2 ± 0.0 | 25.0 ± 0.2 | 4.0 |
| HSA-K500A-IL1RA | ND | ND | ND |
| HSA-D550N-IL1RA | 7.3 ± 0.2 | 38.0 ± 0.0 | 5.2 |
| HSA-K573A-IL1RA | 6.1 ± 0.0 | 7.1 ± 0.1 | 1.1 |
| HSA-K573P-IL1RA | 6.2 ± 0.1 | 1.3 ± 0.1 | 0.2 |
| scFv-HSA-K500A-FLAG | ND | ND | ND |
| scFv-HSA-D550N-FLAG | 6.2 ± 0.0 | 18.0 ± 0.0 | 2.9 |
| scFv-HSA-K573A-FLAG | 6.4 ± 0.1 | 5.7 ± 0.2 | 0.9 |
| scFv-HSA-K573P-FLAG | 5.8 ± 0.0 | 1.1 ± 0.1 | 0.2 |
| scFv-HSA-WT-scFv-FLAG | 7.5 ± 0.0 | 15.0 ± 0.2 | 2.0 |
| scFv-HSA-K500A-scFv-FLAG | ND | ND | ND |
| scFv-HSA-D550N-scFv-FLAG | 4.1 ± 0.1 | 27.0 ± 0.2 | 6.6 |
| scFv-HSA-K573P-scFv-FLAG | 6.0 ± 0.2 | 0.7 ± 0.1 | 0.1 |
| HSA-K500A-scFv-FLAG | ND | ND | ND |
| HSA-D550N-scFv-FLAG | 7.3 ± 0.1 | 42.0 ± 0.3 | 5.8 |
| HSA-K573A-scFv-FLAG | 6.4 ± 0.1 | 5.7 ± 0.1 | 0.9 |
| HSA-K573P-scFv-FLAG | 4.7 ± 0.1 | 0.7 ± 0.1 | 0.1 |
| scFv-HSA-K500A | ND | ND | ND |
| scFv-HSA-D550N | 7.5 ± 0.1 | 19.0 ± 0.2 | 2.5 |
| scFv-HSA-K573P | 7.4 ± 0.1 | 0.8 ± 0.1 | 0.1 |

[a]Dilutions of HSA variants were injected over immobilized shFcRn (~1500 RU).
[b]The kinetic rate constants were obtained using a simple first-order (1:1) bimolecular interaction model. The kinetic values represent the average of duplicates.
[c]Not determined due to weak binding (ND).

In example 8 it was shown that the K500A variant did not significantly bind shFcRn, in Example 10 it was shown that the K573P and K573A variants bind shFcRn stronger than HSA and in Example 11 it was shown that the D550N variant binds FcRn weaker than HSA.

In the present example it is shown that these observed difference in binding properties also are reflected in fusion polypeptides in different configurations: C-terminal fusions with a small moiety (HSA-FLAG), C-terminal fusions with a larger polypeptide (HSA-IL1RA); N-terminal fusions with polypeptide (scFv-HSA); N- and C-terminal fusions (scFv-HSA-FLAG and scFv-HSA-scFv-FLAG).

Example 17

Conjugation of Horseradish Peroxidase Protein to Albumin and the K573P Variant For conjugation analysis, commercially available recombinant albumin (RECOMBUMIN™ brand albumin) was used as a control molecule. For this example, a final 200 mg/mL albumin K573P variant of the invention was purified from a fed batch fermentation by means described in Material and Methods. A two-step purification was carried out;

The first step used a column (bed volume approximately 400 mL, bed height 11 cm) packed with ALBUPURE™ brand matrix (ProMetic). This was equilibrated with 50 mM sodium acetate, pH 5.3 and loaded with neat culture supernatant, at approximately pH 5.5-6.5, to approximately 20 mg/mL matrix. The column was then washed with approximately 5 column volumes each of 50 mM sodium acetate, pH 5.3, 50 mM sodium phosphate, pH 6.0, 50 mM sodium phosphate, pH 7.0 and 50 mM ammonium acetate, pH 8.0, respectively. Bound protein was eluted using approximately two column volumes of 50 mM ammonium acetate, 10 mM octanoate, pH 7.0. The flow rate for the entire purification was 154 mL/min.

For the second step, the eluate from the first step was diluted approximately two fold with water to give a conductivity of 2.5±0.5 mS/cm after adjustment to pH 5.5±0.3 with acetic acid. This was loaded onto a DEAE-Sepharose Fast Flow (GE Healthcare) column (bed volume approximately 400 mL, bed height 11 cm), equilibrated with 80 mM sodium acetate, 5 mM octanoate, pH 5.5. Loading was approximately 30 mg protein/mL matrix. The column was washed with approximately 5 column volumes of 80 mM sodium acetate, 5 mM octanoate, pH 5.5. Followed by approximately 10 column volumes of 15.7 mM potassium tetraborate, pH 9.2. The bound protein was eluted using two column volumes of 110 mM potassium tetraborate, 200 nM sodium chloride, approximately pH 9.0. The flow rate was 183 mL/min during the load and wash steps, and 169 mL/min during the elution step.

The eluate was concentrated and diafiltered against 145 mM NaCl, using a Pall CENTRAMATE brand Omega 10,000 Nominal MWCO membrane, to give a final protein concentration of approximately 200 mg/mL.

Both 200 mg/mL stock solutions of the rHA and K573P variant albumin were diluted down to 5 mg/mL, using phosphate buffer saline (PBS), pH adjusted to pH 6.5-6.7. This ensured a favorable pH environment for the maleimide reactive group of the EZ-Link® Maleimide Activated Horseradish Peroxidase (Thermo Scientific) to react with the free sulphydryl, to form a stable thioester bond. 2 mg of the EZ-Link® Maleimide Activated Horseradish Peroxidase (HRP) was mixed with either 1 mL of the 5 mg/ML rHA or K573P variant albumin. This mixture ensured an approximate 2 fold molar excess of the albumin, or K573P variant albumin. This mixture was minimally incubated at 4° C., for 24 hours. The reaction mixtures were then checked for conjugation, using GP-HPLC.

To separate unconjugated species (rHA, or Albumin variant K573P and unreacted HRP) from the corresponding conjugated species the samples were first concentrated (VIVASPIN®20 brand centrifugal concentrator 10,000 MWCO PES, Sartorius), and then individually applied to a Tricorn SUPERDEX™ 200 brand column, 10/300 GL brand column (GE Healthcare), run at a flow rate of 45 cm/hr in PBS. The elution peak was fractionated and GP-HPLC analysed. Fractions containing the conjugated species were pooled, concentrated and diafiltered against 50 mM NaCl and analysed by GP-HPLC to demonstrate (See FIG. 24(a) and FIG. 24(b).) concentrated and diafiltered against 50 mM NaCl and analysed by GP-HPLC to demonstrate (FIG. 24)

These samples were then assayed using the method described herein (Table 21). This example demonstrates that the K573P maintains its increased affinity for shFcRn compared the WT HSA.

Example 18

Conjugation of Fluorescein to Albumin and the K573P Variant

The two same albumin samples used in Example 17, were also the start materials for this example. I.e. Approximately 200 mg/mL rHA or the K573P albumin variant.

Fluorescein-5-Maleimide, Thermo Scientific (F5M) was dissolved in dimethylformamide, to give a final concentration of 25 mg/mL. This was then further diluted into 18 mls of PBS, pH adjusted to approximately pH 6.5. To this solution either 1 ml of 200 mg/mL rHA or 1 mL of 200 mg/mL K573P variant was added. This gave an approximate 20 fold final molar excess of F5M. These samples were incubated and allowed to conjugate overnight at 4° C., in the dark, to allow the maleimide groups on the F5M to react with predominantly the free sulfhydryl, present in both albumin species.

Following overnight incubation aliquots of the reaction mixtures were extensively diafiltered against 50 mM NaCl to remove unconjugated F5M, (VIVASPIN®20 brand centrifugal concentrator 10,000 MWCO PES, Sartorius). Conjugation was confirmed by ultraviolet visualization of conjugated Fluorescein::Albumins Following standard SDS-PAGE (FIG. 25).

These diafiltered samples were then assayed using the method described herein (Table 21). This example demonstrates that the conjugation of a small molecule to either rHA or a variant, e.g. K573P does not affect the trend in binding affinities to shFcRn.

TABLE 21

Representative Biacore assay KD values of conjugated rHA or a variant (K573P) when binding to immobilized shFcRn.

| Analyte | KD (μM) |
|---|---|
| rHA::HRP | 3.6 |
| K573P::HRP | 0.02 |
| rHA::F5M | 7.3 |
| K573P::F5M | 2.5 |

Example 19

Further Albumin Variants

The following variants were generated using the methods described in Example 1E492T, N503D, E492T+N503D, K538H, E542D, D494N+E495Q+T496A, E495Q+T496A, N403K, K541A and K541N. SPR analysis was carried out as described in Example 15 and the results presented in FIG. 26 and FIG. 27.

FIGS. 30A and 30B shows the effect on shFcRn binding for the albumin variants.

Substitutions N503D, D494N+E495Q+T496A E492T+N503D, E495Q+T496A within HSA had a negative impact on binding to shFcRn at pH5.5.

Example 20

Variants of Albumin at the C-Termini

The following variants were generated using the methods described in Example 1. Binding to the shFcRn was determined as described in Materials and Methods and the results are presented in Table 22.

TABLE 22

Kinetics of the HSA C-terminal swapped variant interactions with shFcRn.

| Albumin variant[a] | ka (10³/Ms) | kd (10⁻³/s) | KD[b] (μM) |
|---|---|---|---|
| HSA | 4.4 ± 0.0 | 24.0 ± 0.1 | 5.4 |
| MacSA | 3.1 ± 0.1 | 8.6 ± 0.1 | 2.7 |
| HSA-MacC | 4.1 ± 0.1 | 5.6 ± 0.0 | 1.3 |
| MouseSA[c] | 3.8 ± 0.0 | 3.1 ± 0.1 | 0.8 |
| HSA-MouseC | 3.7 ± 0.1 | 1.3 ± 0.0 | 0.3 |
| RabbitSA[d] | 1.9 ± 0.3 | 1.7 ± 0.1 | 0.9 |
| HSA-RabC | 3.5 ± 0.0 | 1.6 ± 0.0 | 0.4 |
| SheepSA | ND | ND | ND |
| HSA-SheepC | 3.3 ± 0.0 | 2.1 ± 0.0 | 0.6 |

[a]Dilutions of HSA variants were injected over immobilized shFcRn (~1500 RU).
[b]The kinetic rate constants were obtained using a simple first-order (1:1) bimolecular interaction model.
[c]Data from Table 2
[d]Data from Table 3
Not determined due to weak binding (ND)

This example demonstrates that for all C-terminal swaps to human albumin tested an increase in binding over the donor albumin was observed. All donor sequences contain the K573P substitution shown to significantly increase binding but less that the K573P alone (Table 20).

Example 21

Competitive Binding Analysis of Variant Albumin Fusions

Competitive binding studies, using variant albumin fusions and a selection of variant albumins prepared as described in Example 1, were performed as described in Example 4. Results are presented in FIGS. 28-31.

The competitive binding hierarchy was identical for the variants fusions of HSA-FLAG and, N+C-terminal scFv HSA-FLAG to the hierarchy of the individual HSA variants (unfused and fused) affinity data. For the IL1Ra variants K573P, K573A, and the K500A were as predicted, however the D550N appears to inhibit more efficiently than the WT fusion.

Example 22

Further HSA Variants

The following variants were generated using methods described in Example 1: HSA E492G+K573A, HSA E492G+N503K+K573A, HSA E492G+N503H+K573A, HSA E492G+K573P, HSA E492G+N503K+K573P, HSA E492G+N503H+K573P. SPR analysis was performed as described in Materials and Methods. Results (FIG. 32) showed that all HSA variants bound more strongly to shFcRn compared to wild type HSA at pH 5.5. No binding was observed at pH 7.4.

HSA E492G+K573A, HSA E492G+N503K+K573A, unlike HSA E492G+N503H+K573A, had marginally improved binding beyond that of HSA K573A. The combination variants containing K573P did not show improved binding over the K573P single variant.

The invention claimed is:

1. A variant of albumin comprising a substitution in a position corresponding to position 573 in the amino acid sequence of SEQ ID NO:2, wherein the substitution is selected from the group consisting of K573A,C,D,F,G,H,I,L,M,N,P,Q,R,S,V,W, and Y, and wherein the variant has at least 98% sequence identity to the amino acid sequence of SEQ ID NO:2.

2. The variant of claim 1, wherein the variant has at least 99% sequence identity to the amino acid sequence of SEQ ID NO:2.

3. The variant of claim 1, wherein the variant consists of the amino acid sequence of SEQ ID NO:2 with a substitution at position 573.

4. The variant of claim 1, wherein the substitution is K573A.

5. The variant of claim 1, wherein the substitution is K573C.

6. The variant of claim 1, wherein the substitution is K573D.

7. The variant of claim 1, wherein the substitution is K573F.

8. The variant of claim 1, wherein the substitution is K573G.

9. The variant of claim 1, wherein the substitution is K573H.

10. The variant of claim 1, wherein the substitution is K573I.

11. The variant of claim 1, wherein the substitution is K573L.

12. The variant of claim 1, wherein the substitution is K573M.

13. The variant of claim 1, wherein the substitution is K573N.

14. The variant of claim 1, wherein the substitution is K573P.

15. The variant of claim 1, wherein the substitution is K573Q.

16. The variant of claim 1, wherein the substitution is K573R.

17. The variant of claim 1, wherein the substitution is K573S.

18. The variant of claim 1, wherein the substitution is K573V.

19. The variant of claim 1, wherein the substitution is K573W.

20. The variant of claim 1, wherein the substitution is K573Y.

* * * * *